United States Patent
Garbaccio et al.

(10) Patent No.: US 10,869,929 B2
(45) Date of Patent: Dec. 22, 2020

(54) PHOSPHONATE LINKERS AND THEIR USE TO FACILITATE CELLULAR RETENTION OF COMPOUNDS

(71) Applicant: Merck Sharp & Dohme Corp., Rahway, NJ (US)

(72) Inventors: Robert M. Garbaccio, Lansdale, PA (US); Jeffrey C. Kern, Gilbertsville, PA (US); James J. Mulhearn, Elkins Park, PA (US); Philip E. Brandish, Needham, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/072,347

(22) PCT Filed: Jan. 24, 2017

(86) PCT No.: PCT/US2017/014644
§ 371 (c)(1),
(2) Date: Jul. 25, 2018

(87) PCT Pub. No.: WO2017/132103
PCT Pub. Date: Aug. 3, 2017

(65) Prior Publication Data
US 2019/0030171 A1 Jan. 31, 2019

Related U.S. Application Data

(60) Provisional application No. 62/288,492, filed on Jan. 29, 2016.

(51) Int. Cl.
| | |
|---|---|
| *A61K 47/54* | (2017.01) |
| *A61K 47/68* | (2017.01) |
| *C07F 9/38* | (2006.01) |
| *C07F 9/40* | (2006.01) |
| *A61P 29/00* | (2006.01) |
| *A61P 35/00* | (2006.01) |

(52) U.S. Cl.
CPC ........ *A61K 47/548* (2017.08); *A61K 47/6803* (2017.08); *A61K 47/6849* (2017.08); *A61K 47/6889* (2017.08); *C07F 9/3839* (2013.01); *C07F 9/40* (2013.01); *A61P 29/00* (2018.01); *A61P 35/00* (2018.01)

(58) Field of Classification Search
None
See application file for complete search history.

(56) References Cited

U.S. PATENT DOCUMENTS

| | | |
|---|---|---|
| 5,094,848 A | 3/1992 | Brixner et al. |
| 5,621,002 A | 4/1997 | Bosslet et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,677,435 B2 | 1/2004 | Barbas, III et al. |
| 6,759,509 B1 | 7/2004 | King et al. |
| 6,835,807 B1 | 12/2004 | Susaki et al. |
| 7,229,618 B2 | 6/2007 | Johnson et al. |
| 10,550,190 B2 | 2/2020 | Garbaccio |
| 2002/0042539 A1 | 4/2002 | Arstad et al. |
| 2002/0102590 A1 | 8/2002 | Taing et al. |
| 2003/0096743 A1 | 5/2003 | Senter et al. |
| 2003/0130189 A1 | 7/2003 | Senter et al. |
| 2004/0018194 A1 | 1/2004 | Francisco et al. |
| 2004/0052793 A1 | 3/2004 | Carter et al. |
| 2004/0121940 A1 | 6/2004 | De Groot et al. |
| 2004/0219203 A1 | 11/2004 | Griffiths et al. |
| 2006/0122143 A1 | 6/2006 | Boyer et al. |
| 2007/0048773 A1 | 3/2007 | Lee et al. |
| 2010/0249072 A1 | 9/2010 | Borch et al. |
| 2012/0058473 A1 | 3/2012 | Yue et al. |
| 2015/0065393 A1 | 3/2015 | Jacobson |
| 2017/0182181 A1 | 6/2017 | Garbaccio |
| 2019/0071483 A1 | 3/2019 | Carrington |

FOREIGN PATENT DOCUMENTS

| | | |
|---|---|---|
| WO | WO199813059 A1 | 4/1998 |
| WO | WO2004032828 A2 | 4/2004 |
| WO | 2009058734 A1 | 5/2009 |
| WO | WO2010096142 A1 | 8/2010 |
| WO | WO2014153164 A1 | 8/2010 |
| WO | WO2011116387 A1 | 9/2011 |
| WO | 2014073845 A1 | 5/2014 |
| WO | 2015006736 A2 | 1/2015 |
| WO | 2015153401 | 10/2015 |
| WO | WO2017062271 A3 | 6/2017 |

OTHER PUBLICATIONS

Kern et al. Discovery of pyrophosphate diesters as tunable, soluble and bioorthogonal linkers for site-specific antibody-drug conjugates. J. Am. Chem. 2015, 138, 1430-1445.*
International Search Report PCTUS1714644 (International Filing date: Jan. 24, 2017), dated May 2, 2018.
Alley et al., Contribution of Linker Stability to the Activity of Anticancer Immunoconjugates, Bioconjugate Chem., 2008, pp. 759-765, 19.
Austin et al., Oxidizing Potential of Endosomes and Lysosomes Limits Intracellular Cleavage of Disulfide Based Antibody Drug Conjugates, Proc. Natl. Acad. Sci., USA, 2005, pp. 17987-17992, 102.
Blattler et al., New Heterobifunctional Protein Cross-linking Reagent that forms an Acid Labile Link, Biochem., 1985, pp. 1517-1524, 24.
Carl et al., A Novel Connector Linkage Applicable in Prodrug Design, J. Med. Chem., 1981, pp. 479-480, 24.

(Continued)

*Primary Examiner* — Samantha L Shterengarts
(74) *Attorney, Agent, or Firm* — David Van Goor, Esq.; Anna L. Cocuzzo, Esq.

(57) ABSTRACT

Phosphonate linkers and their use for delivering compounds with passive cell permeability into a cell wherein the phosphonate group facilitates cellular retention of the compound are described.

5 Claims, No Drawings
Specification includes a Sequence Listing.

(56) References Cited

OTHER PUBLICATIONS

Chabenne, J. et al., A Glucagon Analog Chemically Stabilized for Immediate Treatment of Life-threatening hypoglycemia, Molecular Metabolism, 2014, No. 3, pp. 293-300, 3.

Chakravarty et al., Plasmin-activated Prodrugs for Cancer Chemotherapy, J. Med. Chem., 1983, pp. 638-644, 26.

Chari et al., Targeted Delivery of Chemotherapeutics: Tumoractivated Prodrug Therapy, Adv. Drug Delivery Rev., 1998, pp. 89-104, 31.

De Groot et al., Design, Synthesis, and Biological Evaluation of a Dual Tumor Specific Motive, Molecular Cancer Therapeutics, 2002, pp. 901-911, 1.

De Groot et al., Elongated Multiple Electronic Cascade and Cyclization Spacer Systems in Activatible Anticancer Prodrugs for Enhanced Drug Release, Journal of Organic Chemistry, 2001, pp. 8815-8830, 66.

De Groot et al., Synthesis and Biological Evaluation of Novel Prodrugs of Anthracyclines for Selective Activation by the Tumor-Associated Protease Plasmin, J. Med. Chem., 1999, pp. 5277-5283, 42.

Doronina et al., Enhanced Activity of Monomethylauristatin F through Monoclonal Antibody Delivery, Bioconj. Chem., 2006, pp. 114-124, 17.

Erickson et al., Antibody-Maytansinoid Conjugates are Activated in Targeted Cancer Cells by Lysomomal Degradation, Cancer Research, 2006, pp. 4426-4433, 66.

Graversen, JH, Targeting the Hemoglobin Scavenger receptor CD163 in Macrophages Highly Increases the Anti-inflammatory Potency of Dexamethasone, The Journal of the American Society of Gene Therapy, 2012, 1550-1558, vol. 20, No. 8.

Hamann et al., An Anti-MUC1 Antibody Calicheamicin Conjugate for Treatment of Solid Tumors, Bioconj. Chem., 2005, pp. 346-353, 16.

Hashimoto et al., Significance of Cathepsin B Accumulation in Synovial luid of Rheumatoid Arthritis, Biochem Biophys. Res. Commun., 2001, pp. 334-339, 288.

Hong et al., Nucleoside Conjugates as Potential Antitumor Agents, Journal of Medicinal Chemistry, 1979, No. 11, pp. 1428-1432, 22.

King et al., Monoclonal Antibody Conjugates of Doxorubicin Prepared with Branched Peptide Linkers, J. Med. Chem., 2002, pp. 4336-4343, 45.

Lewis et al., Targeting HER2-Positive Brease Cancer with Trastuzumab-DM1, An Antibody-Cytotoxic Drug Conjugate, Cancer Research, 2008, pp. 9280-9290, 68.

Na, Pub Chem Compound Summary, CID21125146, 2007, pp. 1 and 2, NA.

Ostrovskis et al., Application of Metal Free Click Chemistry in Biological Studies, Current Organic Chemistry, 2013, pp. 610-640, 17.

Sinha et al., Plasma Membrane Association of Cathepsin B in Human Prostate Cancer, Prostate, 2001, pp. 172-184, 49.

Widdison et al., Semisynthetic Maytansine Analogues for the Targeted Treatment of Cancer, J. Med. Chem., 2006, pp. 4392-4408, 49.

Co-pending U.S. Appl. No. 15/765,515, filed Apr. 3, 2018, Philip E. Brandish et al.

Hallam, Trevor J. et al., Antibody Conjugates with Unnatural Amino Acids, Molecular Pharmaceutics, 2015, 1848-1862, 12.

\* cited by examiner

SEQUENCE LISTING

<160> NUMBER OF SEQ ID NOS: 68

<210> SEQ ID NO 1
<211> LENGTH: 12
<212> TYPE: PRT
<213> ORGANISM: Artificial Sequence
<220> FEATURE:
<223> OTHER INFORMATION: CDR sequence

<400> SEQUENCE: 1

Arg Ala Ser Gln Ser Val Ser Ser Ser Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CDR sequence

<400> SEQUENCE: 2

Gly Ala Ser Ser Arg Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CDR sequence

<400> SEQUENCE: 3

Gln Gln Tyr Ser Ser Ser Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: CDR sequence

<400> SEQUENCE: 4

Arg Tyr Ile Ile Asn
1               5

<210> SEQ ID NO 5
<211> LENGTH: 17
<212> TYPE: PRT
<213> ORGANISM: Artificial Sequence
<220> FEATURE:
<223> OTHER INFORMATION: CDR sequence

<400> SEQUENCE: 5

Arg Ile Ile Pro Ile Leu Gly Val Glu Asn Tyr Ala Gln Lys Phe Gln
1               5                   10                  15

Gly

<210> SEQ ID NO 6
<211> LENGTH: 6
<212> TYPE: PRT
<213> ORGANISM: Artificial Sequence
<220> FEATURE:
<223> OTHER INFORMATION: CDR sequence

<400> SEQUENCE: 6

Lys Asp Trp Phe Asp Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: CDR sequence

<400> SEQUENCE: 7

Arg Tyr Pro Ile Asn
1               5

<210> SEQ ID NO 8
<211> LENGTH: 17
<212> TYPE: PRT
<213> ORGANISM: Artificial Sequence
<220> FEATURE:
<223> OTHER INFORMATION: CDR sequence

<400> SEQUENCE: 8

Arg Ile Ile Pro Ile Leu Gly Ile Ala Asp Tyr Ala Gln Arg Phe Gln
1               5                   10                  15

Gly

<210> SEQ ID NO 9
<211> LENGTH: 6
<212> TYPE: PRT
<213> ORGANISM: Artificial Sequence
<220> FEATURE:
<223> OTHER INFORMATION: CDR sequence

<400> SEQUENCE: 9

Arg Asp Trp Gly Asp Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: CDR sequence

<400> SEQUENCE: 10

Gln Gln Tyr Gly Ser Ser Pro Ile Thr
1               5

<210> SEQ ID NO 11
<211> LENGTH: 5
<212> TYPE: PRT
<213> ORGANISM: Artificial Sequence
<220> FEATURE:
<223> OTHER INFORMATION: CDR sequence

<400> SEQUENCE: 11

Arg Tyr Ala Ile Asn
1               5

<210> SEQ ID NO 12
<211> LENGTH: 17
<212> TYPE: PRT
<213> ORGANISM: Artificial Sequence
<220> FEATURE:
<223> OTHER INFORMATION: CDR sequence

<400> SEQUENCE: 12

Arg Ile Ile Pro Ile Leu Asp Ile Ala Asp Tyr Ala Gln Lys Phe Gln
1               5                   10                  15

Asp

<210> SEQ ID NO 13
<211> LENGTH: 6
<212> TYPE: PRT
<213> ORGANISM: Artificial Sequence
<220> FEATURE:
<223> OTHER INFORMATION: CDR sequence

<400> SEQUENCE: 13

Lys Asp Trp Phe Asp Pro
1               5

<210> SEQ ID NO 14
<211> LENGTH: 5
<212> TYPE: PRT
<213> ORGANISM: Artificial Sequence
<220> FEATURE:
<223> OTHER INFORMATION: CDR sequence

<400> SEQUENCE: 14

Arg Tyr Pro Ile Asn
1               5

<210> SEQ ID NO 15
<211> LENGTH: 11
<212> TYPE: PRT
<213> ORGANISM: Artificial Sequence
<220> FEATURE:
<223> OTHER INFORMATION: CDR sequence

<400> SEQUENCE: 15

Arg Ala Ser Gln Ser Val Ser Ser Tyr Leu Ala
1               5                   10

<210> SEQ ID NO 16
<211> LENGTH: 8
<212> TYPE: PRT
<213> ORGANISM: Artificial Sequence
<220> FEATURE:
<223> OTHER INFORMATION: CDR sequence

<400> SEQUENCE: 16

Tyr Asp Ala Ser Asn Arg Ala Thr
1               5

<210> SEQ ID NO 17
<211> LENGTH: 9
<212> TYPE: PRT
<213> ORGANISM: Artificial Sequence
<220> FEATURE:
<223> OTHER INFORMATION: CDR sequence

<400> SEQUENCE: 17

Gln Gln Arg Thr Asn Trp Pro Leu Thr
1               5

<210> SEQ ID NO 18
<211> LENGTH: 5
<212> TYPE: PRT
<213> ORGANISM: Artificial Sequence
<220> FEATURE:
<223> OTHER INFORMATION: CDR sequence

<400> SEQUENCE: 18

Ser Tyr Ile Met His
1               5

<210> SEQ ID NO 19
<211> LENGTH: 16
<212> TYPE: PRT
<213> ORGANISM: Artificial Sequence
<220> FEATURE:
<223> OTHER INFORMATION: CDR sequence

<400> SEQUENCE: 19

Val Ile Ser Tyr Asp Gly Arg Asn Lys Tyr Tyr Ala Asp Ser Val Lys
1               5                   10                  15

<210> SEQ ID NO 20
<211> LENGTH: 9
<212> TYPE: PRT
<213> ORGANISM: Artificial Sequence
<220> FEATURE:
<223> OTHER INFORMATION: CDR sequence

<400> SEQUENCE: 20

Asp Thr Asp Gly Tyr Asp Phe Asp Tyr
1               5

<210> SEQ ID NO 21
<211> LENGTH: 11
<212> TYPE: PRT
<213> ORGANISM: Artificial Sequence
<220> FEATURE:
<223> OTHER INFORMATION: CDR sequence

<400> SEQUENCE: 21

Arg Ala Ser Gln Gly Ile Ser Ser Ala Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: CDR sequence

<400> SEQUENCE: 22

Asp Ala Ser Ser Leu Glu Ser
1               5

<210> SEQ ID NO 23
<211> LENGTH: 9
<212> TYPE: PRT
<213> ORGANISM: Artificial Sequence
<220> FEATURE:
<223> OTHER INFORMATION: CDR sequence

<400> SEQUENCE: 23

Gln Gln Phe Asn Ser Tyr Pro Phe Thr
1               5

<210> SEQ ID NO 24
<211> LENGTH: 5
<212> TYPE: PRT
<213> ORGANISM: Artificial Sequence
<220> FEATURE:
<223> OTHER INFORMATION: CDR sequence

<400> SEQUENCE: 24

Tyr Tyr Ala Met His
1               5

<210> SEQ ID NO 25
<211> LENGTH: 16
<212> TYPE: PRT
<213> ORGANISM: Artificial Sequence
<220> FEATURE:
<223> OTHER INFORMATION: CDR sequence

<400> SEQUENCE: 25

Val Ile Ser Tyr Asp Gly Ser Ile Lys Tyr Tyr Ala Asp Ser Val Lys
1               5                   10                  15

<210> SEQ ID NO 26
<211> LENGTH: 10
<212> TYPE: PRT
<213> ORGANISM: Artificial Sequence
<220> FEATURE:
<223> OTHER INFORMATION: CDR sequence

<400> SEQUENCE: 26

Glu Gly Pro Tyr Ser Asn Tyr Leu Asp Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: CDR sequence

<400> SEQUENCE: 27

Arg Ala Ser Gln Gly Ile Ser Ser Trp Leu Ala

<210> SEQ ID NO 28
<211> LENGTH: 7
<212> TYPE: PRT
<213> ORGANISM: Artificial Sequence
<220> FEATURE:
<223> OTHER INFORMATION: CDR sequence

<400> SEQUENCE: 28

Ala Ala Ser Ser Leu Gln Ser
1               5

<210> SEQ ID NO 29
<211> LENGTH: 9
<212> TYPE: PRT
<213> ORGANISM: Artificial Sequence
<220> FEATURE:
<223> OTHER INFORMATION: CDR sequence

<400> SEQUENCE: 29

Gln Gln Tyr Asn Ser Tyr Pro Leu Thr
1               5

<210> SEQ ID NO 30
<211> LENGTH: 5
<212> TYPE: PRT
<213> ORGANISM: Artificial Sequence
<220> FEATURE:
<223> OTHER INFORMATION: CDR sequence

<400> SEQUENCE: 30

Asp Tyr Gly Met His
1               5

<210> SEQ ID NO 31
<211> LENGTH: 16
<212> TYPE: PRT
<213> ORGANISM: Artificial Sequence
<220> FEATURE:
<223> OTHER INFORMATION: CDR sequence

<400> SEQUENCE: 31

Val Ile Trp Tyr Asp Gly Ser Asn Lys Tyr Tyr Ala Asp Ser Val Lys
1               5                   10                  15

<210> SEQ ID NO 32
<211> LENGTH: 10
<212> TYPE: PRT
<213> ORGANISM: Artificial Sequence
<220> FEATURE:
<223> OTHER INFORMATION: CDR sequence

<400> SEQUENCE: 32

Asp Ser Ile Val Met Val Arg Gly Asp Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: CDR sequence

<400> SEQUENCE: 33

Arg Ala Ser Gln Gly Ile Ser Ser Trp Leu Ala
1               5                   10

```
<210> SEQ ID NO 34
<211> LENGTH: 7
<212> TYPE: PRT
<213> ORGANISM: Artificial Sequence
<220> FEATURE:
<223> OTHER INFORMATION: CDR sequence

<400> SEQUENCE: 34

Ala Ala Ser Ser Leu Gln Ser
1               5

<210> SEQ ID NO 35
<211> LENGTH: 9
<212> TYPE: PRT
<213> ORGANISM: Artificial Sequence
<220> FEATURE:
<223> OTHER INFORMATION: CDR sequence

<400> SEQUENCE: 35

Gln Gln Tyr Asn Ser Tyr Pro Leu Thr
1               5

<210> SEQ ID NO 36
<211> LENGTH: 5
<212> TYPE: PRT
<213> ORGANISM: Artificial Sequence
<220> FEATURE:
<223> OTHER INFORMATION: CDR sequence

<400> SEQUENCE: 36

Asp His Gly Met His
1               5

<210> SEQ ID NO 37
<211> LENGTH: 16
<212> TYPE: PRT
<213> ORGANISM: Artificial Sequence
<220> FEATURE:
<223> OTHER INFORMATION: CDR sequence

<400> SEQUENCE: 37

Val Ile Trp Tyr Asp Gly Ser Asn Lys Tyr Tyr Ala Asp Ser Val Lys
1               5                   10                  15

<210> SEQ ID NO 38
<211> LENGTH: 9
<212> TYPE: PRT
<213> ORGANISM: Artificial Sequence
<220> FEATURE:
<223> OTHER INFORMATION: CDR sequence

<400> SEQUENCE: 38

Asp Ser Ile Met Val Arg Gly Asp Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: CDR sequence

<400> SEQUENCE: 39

Asp Ala Ser Asn Arg Ala Thr
1               5
```

```
<210> SEQ ID NO 40
<211> LENGTH: 9
<212> TYPE: PRT
<213> ORGANISM: Artificial Sequence
<220> FEATURE:
<223> OTHER INFORMATION: CDR sequence

<400> SEQUENCE: 40

Gln Gln Arg Ser Asn Trp Pro Leu Thr
1               5

<210> SEQ ID NO 41
<211> LENGTH: 7
<212> TYPE: PRT
<213> ORGANISM: Artificial Sequence
<220> FEATURE:
<223> OTHER INFORMATION: CDR sequence

<400> SEQUENCE: 41

Ser Asp Tyr Tyr Tyr Trp Ser
1               5

<210> SEQ ID NO 42
<211> LENGTH: 16
<212> TYPE: PRT
<213> ORGANISM: Artificial Sequence
<220> FEATURE:
<223> OTHER INFORMATION: CDR sequence

<400> SEQUENCE: 42

Tyr Ile Tyr Tyr Ser Gly Ser Thr Asn Tyr Asp Pro Ser Leu Lys Ser
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: CDR sequence

<400> SEQUENCE: 43

Gly Asp Gly Asp Tyr Gly Gly Asn Cys Phe Asp Tyr
1               5                   10

<210> SEQ ID NO 44
<211> LENGTH: 16
<212> TYPE: PRT
<213> ORGANISM: Artificial Sequence
<220> FEATURE:
<223> OTHER INFORMATION: CDR sequence

<400> SEQUENCE: 44

Arg Ser Ser Gln Ser Leu Val His Arg Asn Gly Asn Thr Tyr Leu His
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: CDR sequence

<400> SEQUENCE: 45

Thr Val Ser Asn Arg Phe Ser
1               5
```

<210> SEQ ID NO 46
<211> LENGTH: 9
<212> TYPE: PRT
<213> ORGANISM: Artificial Sequence
<220> FEATURE:
<223> OTHER INFORMATION: CDR sequence

<400> SEQUENCE: 46

Ser Gln Ser Ser His Val Pro Pro Thr
1               5

<210> SEQ ID NO 47
<211> LENGTH: 5
<212> TYPE: PRT
<213> ORGANISM: Artificial Sequence
<220> FEATURE:
<223> OTHER INFORMATION: CDR sequence

<400> SEQUENCE: 47

Asn Tyr Gly Val Asn
1               5

<210> SEQ ID NO 48
<211> LENGTH: 17
<212> TYPE: PRT
<213> ORGANISM: Artificial Sequence
<220> FEATURE:
<223> OTHER INFORMATION: CDR sequence

<400> SEQUENCE: 48

Trp Ile Asn Pro Asn Thr Gly Glu Pro Thr Phe Asp Asp Asp Phe Lys
1               5                   10                  15

Gly

<210> SEQ ID NO 49
<211> LENGTH: 11
<212> TYPE: PRT
<213> ORGANISM: Artificial Sequence
<220> FEATURE:
<223> OTHER INFORMATION: CDR sequence

<400> SEQUENCE: 49

Ser Arg Gly Lys Asn Glu Ala Trp Phe Ala Tyr
1               5                   10

<210> SEQ ID NO 50
<211> LENGTH: 6
<212> TYPE: PRT
<213> ORGANISM: Artificial Sequence
<220> FEATURE:
<223> OTHER INFORMATION: CDR sequence

<400> SEQUENCE: 50

Gln Gly Ile Ser Ser Trp
1               5

<210> SEQ ID NO 51
<211> LENGTH: 9
<212> TYPE: PRT
<213> ORGANISM: Artificial Sequence
<220> FEATURE:
<223> OTHER INFORMATION: CDR sequence

<400> SEQUENCE: 51

Gln Gln Tyr Asn Ser Tyr Pro Leu Thr
1               5

```
<210> SEQ ID NO 52
<211> LENGTH: 8
<212> TYPE: PRT
<213> ORGANISM: Artificial Sequence
<220> FEATURE:
<223> OTHER INFORMATION: CDR sequence

<400> SEQUENCE: 52

Gly Phe Thr Phe Ser Ser Tyr Ala
1               5

<210> SEQ ID NO 53
<211> LENGTH: 8
<212> TYPE: PRT
<213> ORGANISM: Artificial Sequence
<220> FEATURE:
<223> OTHER INFORMATION: CDR sequence

<400> SEQUENCE: 53

Ile Ser Tyr Asp Gly Ser Asn Lys
1               5

<210> SEQ ID NO 54
<211> LENGTH: 16
<212> TYPE: PRT
<213> ORGANISM: Artificial Sequence
<220> FEATURE:
<223> OTHER INFORMATION: CDR sequence

<400> SEQUENCE: 54

Ala Ser Gly Arg Tyr Tyr Gly Ser Gly Ser Tyr Ser Ser Tyr Phe Asp
1               5                   10                  15

<210> SEQ ID NO 55
<211> LENGTH: 8
<212> TYPE: PRT
<213> ORGANISM: Artificial Sequence
<220> FEATURE:
<223> OTHER INFORMATION: CDR sequence

<400> SEQUENCE: 55

Ile Ser Tyr Asp Gly Ser Ile Lys
1               5

<210> SEQ ID NO 56
<211> LENGTH: 16
<212> TYPE: PRT
<213> ORGANISM: Artificial Sequence
<220> FEATURE:
<223> OTHER INFORMATION: CDR sequence

<400> SEQUENCE: 56

Ala Arg Gly Arg Glu Tyr Thr Ser Gln Asn Ile Val Ile Leu Leu Asp
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: CDR sequence

<400> SEQUENCE: 57

Ala Arg Gly Arg Glu Ile Thr Ser Gln Asn Ile Val Ile Leu Leu Asp
1               5                   10                  15
```

```
<210> SEQ ID NO 58
<211> LENGTH: 8
<212> TYPE: PRT
<213> ORGANISM: Artificial Sequence
<220> FEATURE:
<223> OTHER INFORMATION: CDR sequence

<400> SEQUENCE: 58

Ile Trp Tyr Asp Gly Ser Asn Lys
1               5

<210> SEQ ID NO 59
<211> LENGTH: 16
<212> TYPE: PRT
<213> ORGANISM: Artificial Sequence
<220> FEATURE:
<223> OTHER INFORMATION: CDR sequence

<400> SEQUENCE: 59

Ala Arg Gly Gly Thr Leu Val Arg Gly Ala Met Tyr Gly Thr Asp Val
1               5                   10                  15

<210> SEQ ID NO 60
<211> LENGTH: 9
<212> TYPE: PRT
<213> ORGANISM: Artificial Sequence
<220> FEATURE:
<223> OTHER INFORMATION: CDR sequence

<400> SEQUENCE: 60

Ala Ser Gln Ser Val Ser Ser Asp Val
1               5

<210> SEQ ID NO 61
<211> LENGTH: 8
<212> TYPE: PRT
<213> ORGANISM: Artificial Sequence
<220> FEATURE:
<223> OTHER INFORMATION: CDR sequence

<400> SEQUENCE: 61

Gln Asp Tyr Thr Ser Pro Arg Thr
1               5

<210> SEQ ID NO 62
<211> LENGTH: 8
<212> TYPE: PRT
<213> ORGANISM: Artificial Sequence
<220> FEATURE:
<223> OTHER INFORMATION: CDR sequence

<400> SEQUENCE: 62

Gly Tyr Ser Ile Thr Ser Asp Tyr
1               5

<210> SEQ ID NO 63
<211> LENGTH: 12
<212> TYPE: PRT
<213> ORGANISM: Artificial Sequence
<220> FEATURE:
<223> OTHER INFORMATION: CDR sequence

<400> SEQUENCE: 63

Cys Val Ser Gly Thr Tyr Tyr Phe Asp Tyr Trp Gly
1               5                   10

<210> SEQ ID NO 64
```

```
<211> LENGTH: 9
<212> TYPE: PRT
<213> ORGANISM: Artificial Sequence
<220> FEATURE:
<223> OTHER INFORMATION: CDR sequence

<400> SEQUENCE: 64

Ala Ser Gln Ser Val Ser His Asp Val
1               5

<210> SEQ ID NO 65
<211> LENGTH: 8
<212> TYPE: PRT
<213> ORGANISM: Artificial Sequence
<220> FEATURE:
<223> OTHER INFORMATION: CDR sequence

<400> SEQUENCE: 65

Gln Asp Tyr Ser Ser Pro Arg Thr
1               5

<210> SEQ ID NO 66
<211> LENGTH: 4
<212> TYPE: PRT
<213> ORGANISM: Artificial Sequence
<220> FEATURE:
<223> OTHER INFORMATION: Glycosylation site atN297 of IgG1

<400> SEQUENCE: 66

Gln Tyr Asn Ser
1

<210> SEQ ID NO 67
<211> LENGTH: 4
<212> TYPE: PRT
<213> ORGANISM: Artificial Sequence
<220> FEATURE:
<223> OTHER INFORMATION: Glycosylation site atN297 of IgG4

<400> SEQUENCE: 67

Gln Phe Asn Ser
1

<210> SEQ ID NO 68
<211> LENGTH: 4
<212> TYPE: PRT
<213> ORGANISM: Artificial Sequence
<220> FEATURE:
<223> OTHER INFORMATION: Mutated glycosylation site of IgG1 or IgG4

<400> SEQUENCE: 68

Gln Ala Gln Ser
1
```

PHOSPHONATE LINKERS AND THEIR USE TO FACILITATE CELLULAR RETENTION OF COMPOUNDS

CROSS REFERENCE TO RELATED APPLICATIONS

This application is a National Stage Application of International Patent Application of PCT/US2017/014644 filed Jan. 24, 2017, and which claims benefit of U.S. Provisional Application 62/288,492 filed Jan. 29, 2016, both of which are incorporated herein in their entirety.

BACKGROUND OF THE INVENTION

(1) Field of the Invention

The present invention relates to phosphonate linkers and their use to facilitate intracellular retention of compounds with passive cell permeability.

(2) Description of Related Art

Antibody drug conjugates (ADC) are targeted chemotherapeutic molecules combining the ideal properties of both antibodies and cytotoxic drugs by targeting potent cytotoxic drugs to the antigen-expressing tumor cells, internalizing the ADC, and releasing the drug from the ADC, thereby enhancing the drug's anti-tumor activity. This strategy has met limited success in part because many cytotoxic drugs tend to be inactive or less active when conjugated to large antibodies or protein receptor ligands. Promising advancements with immunoconjugates has seen cytotoxic drugs linked to antibodies through a linker that is cleaved at the tumor site or inside tumor cells.

The successful ADC development for a given target antigen depends on optimization of antibody selection, linker design and stability, drug potency and mode of drug and linker conjugation to the antibody. Linker properties of pH and redox sensitivities and protease susceptibility influence circulatory stability and release of the drug moiety. The intracellular cleavage of disulfide containing linkers of an ADC is limited by the oxidizing potential of endosomes and lysosomes and are probably not released by reductive cleavage within the endocytic pathway (Austin et al., Proc. Natl. Acad. Sci. USA 102: 17987-17992 (2005)). Reductive cleavage may occur at the cell membrane and impart a bystander killing effect of tumor and susceptible normal cells by free drug. Inappropriate release of drug likely contributes to toxicity. Once internalized, ADC efficacy is dependent on proteolytic cleavage for drug activity. Linker stability plays an important role in both the efficacy and toxicity of ADC (Alley et al., Bioconjugate Chem. 19:759-765 (2008)). Stable linkers such as mcc are more efficacious and safer than unstable, disulfide linkers, widening the therapeutic window. However, while mcc linkers are more stable than disulfides, they can only be used for drugs that can tolerate residual linker on it and still be potent. Thus, self-immolative linkers are needed for drugs that do not have this flexible structure activity relationship (SAR).

A chemical solution to targeted delivery of cytotoxic or cytostatic drugs conjugated to cell-specific ligands is the "self-immolative linker", PABC or PAB (para-aminobenzyloxycarbonyl) linker, attaching the drug moiety to the ligand in the conjugate (Carl et al., J. Med. Chem. 24: 479-480 (1981); Chakravarty et al., J. Med. Chem. 26: 638-644 (1983)). The PAB linker unit is also referred to as an electronic cascade spacer. The amide bond linking the carboxy terminus of a peptide unit and the para-aminobenzyl of PAB may be a substrate and cleavable by certain proteases. The aromatic amine becomes electron-donating and initiates an electronic cascade that leads to the expulsion of the leaving group, which releases the free drug after elimination of carbon dioxide (de Groot, et al. Journal of Organic Chemistry 66: 8815-8830 (2001)). Cathepsin B is a ubiquitous cysteine protease with increasing activity within low pH environments (i.e. lysosomes). It is an intracellular enzyme, except in pathological conditions, such as metastatic tumors (Sinha et al., Prostate 49: 172-184 (2001)) or rheumatoid arthritis (Hashimoto et al., Biochem. Biophys. Res. Commun. 283: 334-339 (2001)). Therefore, conjugates produced with cathepsin B-cleavable linkers are likely to be stable in circulation. Upon cleavage of a peptide bond adjacent to the PABC, i.e. by an intracellular enzyme, the drug is released from the ligand whereby no remaining portion of the linker is bound (de Groot et al., Molecular Cancer Therapeutics 1: 901-911 (2002); de Groot et al., J. Med. Chem. 42: 5277-5283 (1999)).

Linkers containing the para-aminobenzyloxycarbonyl (PAB or PABC) unit, in conjunction with a peptide unit, have been developed with a "self-immolating" or "self-immolative" mechanism of 1,6 elimination and fragmentation under enzymatic, hydrolytic, or other metabolic conditions to release a drug moiety from a targeting ligand, such as an antibody (U.S. Pat. Nos. 6,214,345; 6,677,435 5,621,002; 6,218,519; 6,835,807; 6,268,488; and 6,759,509; US Pat. Pub. Nos. 20030130189; 20030096743; 20040052793; 20040018194; 20040052793; and 20040121940; PCT Pub. Nos. WO 98/13059 and WO2004/032828).

Limitations of the PAB type self-immolating linkers are the propensity to cause poor solubility and aggregation of the conjugates. In addition, some PAB-containing conjugates may not be suitable substrates for certain cleaving enzymes or cleave too slowly to achieve efficacy. While the PAB/PABC linkers have been exemplified for amine-terminus payloads that form stable carbamate bonds, for payloads that do not contain a linkable amine, the carbonate that is formed may not be stable and so there is a need for self-immolative linkers that can handle payloads with an oxygen terminus, for example, dexamethasone.

WO2015153401 discloses phosphate-based linkers comprising a payload linked to the oxygen atom of a phosphate or phosphonate group and a linker arm comprising a tuning element, an optional spacer element, and a reactive functional group capable of conjugating to a reactive group of a targeting ligand. These phosphate-based linkers have a differentiated and tunable stability in blood vs. an intracellular environment (e.g. lysosomal compartment). Intracellularly, the phosphate or phosphonate group is cleaved to release the payload from the phosphate or phosphonate group.

BRIEF SUMMARY OF THE INVENTION

The present invention provides phosphonate-based linkers comprising a monophosphonate, diphosphonate, triphosphonate, or tetraphosphonate group ("phosphonate group") having the general formula

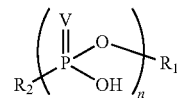

wherein $R_1$ is a first linker arm comprising a tuning element, an optional spacer element, and a reactive functional group capable of reacting with a group on a ligand or targeting moiety in which the tuning element is linked to the O group of the phosphonate group; $R_2$ is a second linker arm comprising a payload linked to the P atom of the phosphonate group via a linker, wherein V is O or S and n=1, 2, 3, or 4. Interspersed between the tuning element and the reactive functional group of the linker arm may be an optional spacer element.

When the phosphonate-based linker is conjugated to a ligand or targeting moiety, a conjugate is provided which may be administered to an individual subcutaneously or intravenously. When the conjugate is administered to an individual, the phosphonate group is stable. However, when the conjugate is subsequently internalized or taken up by a cell, the phosphonate group is labile and is cleaved, the cleavage rate being dependent on the structure of the tuning element comprising the first linker arm. Upon cleavage, a monophosphonate group remains linked to the second linker arm linked to the payload. The monophosphonate group renders the payload polar, which facilitates intracellular retention of the payload. The scheme below illustrates the intracellular cleavage wherein n=1, 2, 3, or 4.

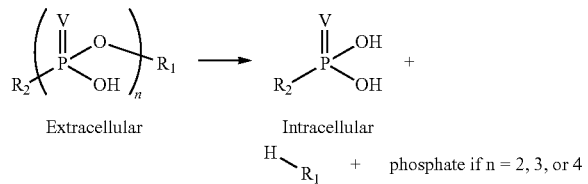

The present invention provides a payload-phosphonate-based linker compound comprising formula (I)

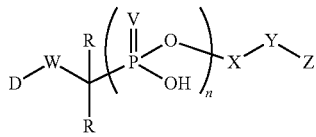

wherein V is selected from O and S; W is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In a further embodiment, the reactive functional group at the proximal end of the payload-phosphoate-based linker may be covalently linked to a ligand or targeting moiety to provide a conjugate wherein in particular embodiments, the ligand is capable of targeting the conjugate to a particular cellular target when administered to a subject in need of the payload to provide a compound having formula (II)

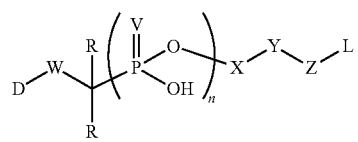

wherein V is selected from O and S; W is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4.

In particular embodiments, the payload is a therapeutic agent, a detectable label, radionuclide, or protecting group. The therapeutic agent may be any molecule that alters, inhibits, activates, or otherwise affects a biological event. Examples of a therapeutic agent include but are not limited to, cytotoxic agent, an anti-inflammatory agent, peptide, a nucleic acid or nucleic acid analog, a small molecule, and a biomolecule.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues of the duocarmycins and CC-1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogs.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, or mometasone.

In particular embodiments, the targeting ligand is an antibody or monoclonal antibody (e.g., chimeric, humanized, or human), ligand for a receptor, lectin, saccharide, poly(ethylene glycol), polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides a composition comprising a compound having formula (II)

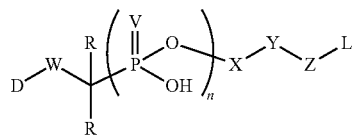

wherein V is selected from O and S; W is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4; and a pharmaceutically acceptable salt or carrier. In particular aspects, the composition is aqueous or lyophilized.

In particular embodiments, the payload is a therapeutic agent, a detectable label, radionuclide, or protecting group. The therapeutic agent may be cytotoxic agent, an anti-inflammatory agent, peptide, or nucleic acid or nucleic acid analog.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues of the duocarmycins and CC-1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogs.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, or mometasone.

In particular embodiments, the targeting ligand is an antibody or monoclonal antibody (e.g., chimeric, humanized, or human) or fragment thereof, ligand for a receptor, lectin; saccharide, poly(ethylene glycol); polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides a method for treating a disease or disorder by providing to a subject having the disease or disorder a composition comprising a compound having formula (II)

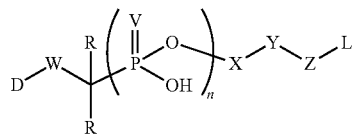

wherein V is selected from O and S; W is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4; and a pharmaceutically acceptable salt or carrier.

In particular aspects, the disease or disorder is an inflammatory disease or cancer.

In particular embodiments, the payload is a therapeutic agent, which may be a cytotoxic agent, an anti-inflammatory agent, peptide, or nucleic acid or nucleic acid analog.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues of the duocarmycins and CC-1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogs.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, or mometasone.

In particular embodiments, the targeting ligand is an antibody or monoclonal antibody (e.g., chimeric, humanized, or human) or fragment thereof, ligand for a receptor, lectin, saccharide, poly(ethylene glycol), polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides for the use of composition comprising a compound having formula (II)

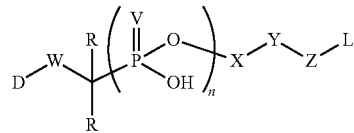

wherein V is selected from O and S; W is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4; and a pharmaceutically acceptable salt or carrier for the treatment of a disease or disorder.

In particular aspects, the disease or disorder is an inflammatory disease or cancer.

In particular embodiments, the payload is a therapeutic agent such as a cytotoxic agent, an anti-inflammatory agent, peptide, or nucleic acid or nucleic acid analog.

In particular embodiments, the cytotoxic agent selected from duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues of the duocarmycins and CC-1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogues.

In particular embodiments, the anti-inflammatory agent is a glucocorticoid receptor agonist. In a further aspect, the anti-inflammatory agent is a glucocorticoid, for example, Cortisol, cortisone acetate, beclometasone, prednisone, prednisolone, methylprednisolone, betamethasone, trimcinolone, budesonide, dexamethasone, fluticasone, or mometasone.

In particular embodiments, the targeting ligand is an antibody or monoclonal antibody (e.g., chimeric, humanized, or human), ligand for a receptor, lectin, saccharide, poly(ethylene glycol), polysaccharide, or polyamino acid.

In particular embodiments, the chimeric, humanized, or human antibody or monoclonal antibody is an anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides an anti-inflammatory compound comprising the formula

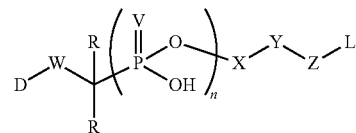

wherein

V is selected from O and S;

W is is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

X is selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group;

Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

D is an anti-inflammatory agent;

Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on the cell-specific targeting ligand (L);

Each occurrence of R is independently hydrogen, a suitable protecting group, an acyl moiety, arylalkyl moiety, aliphatic moiety, aryl moiety, heteroaryl moiety, or heteroaliphatic moiety;

L is a cell-specific targeting ligand; and n is 1, 2, 3, or 4.

In further aspects, the anti-inflammatory agent is a glucocorticoid receptor agonist.

In further aspects, the anti-inflammatory agent is Cortisol, cortisone acetate, beclometasone, prednisone, prednisolone, methylprednisolone, betamethasone, trimcinolone, budesonide, dexamethasone, fluticasone, or mometasone.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides an anti-cancer compound comprising the formula

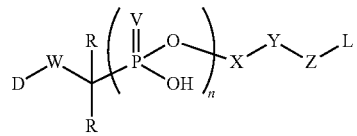

wherein
V is selected from O and S;
W is a bivalent, straight or branched, saturated or unsaturated, optionally substituted C1-30 hydrocarbon chain wherein one or more methylene units are optionally replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

X is selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group;

Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

D is a cytotoxic agent;
Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on the cell-specific targeting ligand (L);

Each occurrence of R is independently hydrogen, a suitable protecting group, an acyl moiety, arylalkyl moiety, aliphatic moiety, aryl moiety, heteroaryl moiety, or heteroaliphatic moiety;
L is a cell-specific targeting ligand; and
n is 1, 2, 3, or 4.

In further aspects, wherein the cytotoxic agent is selected from duocarmycins and CC-1065;

In further aspects, wherein the cytotoxic agent is selected from a CBI (1,2,9,9a-tetrahydrocyclopropa[c]benz[e]indol-4-one)-based analogues, MCBI (7-methoxy-1,2,9,9a-tetrahydrocyclopropa[c]benz[e]indol-4-one)-based analogues and CCBI (7-cyano-1,2,9,9a-tetra-hydrocyclo-propa[c]benz[e]-indol-4-one)-based analogue of the duocarmycins and CC-1065.

In further aspects, the cytotoxic agent is selected from doxorubicin and doxorubicin conjugates such as morpholino-doxorubicin and cyanomorpholino-doxorubicin.

In further aspects, the cytotoxic agent is selected from dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and analogs thereof.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides a method for making an antibody-drug conjugate that has reduced propensity for forming aggregates comprising:
(a) providing a compound comprising the formula

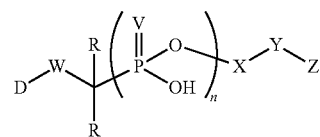

wherein
V is selected from O and S;
W is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

X is selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group;

Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)

C(O)—, —C(O)N(R)—, —S(O)—, —S(O)2-, —N(R) SO2-, SO2N(R)—, a heterocyclic group, an aryl group, or a heteroaryl group;

Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S;

D is a payload;

Each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4; and (b) conjugating the compound to an antibody to make the antibody-drug conjugate that has reduced propensity for forming aggregates.

In further aspects, the payload is a therapeutic agent, a detectable label, radionuclide, or protecting group.

In further aspects, the therapeutic agent is a cytotoxic agent, an anti-inflammatory agent, peptide, or nucleic acid or nucleic acid analog.

In further aspects, the anti-inflammatory agent is a glucocorticoid receptor agonist.

In further aspects, the anti-inflammatory agent is Cortisol, cortisone acetate, beclometasone, prednisone, prednisolone, methylprednisolone, betamethasone, trimcinolone, budesonide, dexamethasone, fluticasone, or mometasone.

In further aspects, the cytotoxic agent is selected from duocarmycins and CC-1065.

In further aspects, the cytotoxic agent is selected from a CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogue of the duocarmycins and CC-1065.

In further aspects, the cytotoxic agent is selected from doxorubicin and doxorubicin conjugates such as morpholino-doxorubicin and cyanomorpholino-doxorubicin.

In further aspects, the cytotoxic agent is selected from dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and analogs thereof.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

The present invention further provides a method for making a composition of antibody-drug conjugates in which the propensity of the antibody-drug conjugates in the composition to form aggregates is reduced comprising:

(a) providing a multiplicity of compounds comprising the formula

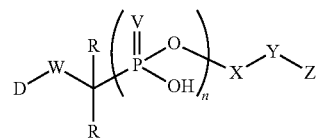

wherein

V is selected from O and S;

W is a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

X is selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group;

Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)2-, —N(R)SO2-, SO2N(R)—, a heterocyclic group, an aryl group, or a heteroaryl group;

Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S;

D is a payload;

each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4; and (b) conjugating the compounds to a multiplicity of antibodies to make the composition in which the propensity of the antibody-drug conjugates therein to form aggregates is reduced.

In further aspects, the payload is a therapeutic agent, a detectable label, radionuclide, or protecting group.

In further aspects, the therapeutic agent is a cytotoxic agent, an anti-inflammatory agent, peptide, or nucleic acid or nucleic acid analog.

In further aspects, the anti-inflammatory agent is a glucocorticoid receptor agonist.

In further aspects, the anti-inflammatory agent is Cortisol, cortisone acetate, beclometasone, prednisone, prednisolone, methylprednisolone, betamethasone, trimcinolone, budesonide, dexamethasone, fluticasone, or mometasone.

In further aspects, the cytotoxic agent is selected from duocarmycins and CC-1065.

In further aspects, the cytotoxic agent is selected from a CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogue of the duocarmycins and CC-1065.

In further aspects, the cytotoxic agent is selected from doxorubicin and doxorubicin conjugates such as morpholino-doxorubicin and cyanomorpholino-doxorubicin.

In further aspects, the cytotoxic agent is selected from dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and analogs thereof.

In further aspects, the percent of aggregated antibody-drug-conjugate in the composition is 2% or less, 1.5% or less, 1.0% or less, 5% or less, 1% or less, or undetectable.

In further aspects, at least 90%, 95%, 96%, 97% 98%, 99%, 99.5%, 99.4%, 99.3%, or 99.2% of the antibody-drug conjugates in the composition is not aggregated.

In further aspects, the targeting ligand is an antibody or monoclonal antibody (e.g., chimeric, humanized, or human), ligand for a receptor, lectin, saccharide, poly(ethylene glycol), polysaccharide, or polyamino acid.

In further aspects, the targeting ligand is a chimeric, humanized, or human anti-Her2 antibody, anti-CD4 antibody, anti-CD20 antibody, anti-EGFR antibody, anti-CD22 antibody, anti-CD23 antibody, anti-CD25 antibody, anti-CD52 antibody, anti-CD30 antibody, anti-CD33 antibody, anti-CD40L antibody, anti-CD70 antibody, anti-CD74 antibody, anti-CD80 antibody, anti-CD163 antibody, anti-Mucl8 antibody, anti-integrin antibody, anti-PSMA antibody, anti-CEA antibody, anti-CD1 Ia antibody, anti-CTLA4 antibody, or anti-BLys antibody.

Definitions

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

Acyl—As used herein, the term "acyl," refers to a group having the general formula —C(=O)R$^{X1}$, —C(=O)OR$^{X1}$, —C(=O)—OC(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., —$(CH_2)_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; O(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; (CH$_2$)$_{0-4}$O(CH$_2$)$_{0-1}$Ph which may be substituted with R°; CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S) NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; (CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$, —OP(O)R°$_2$; —OP(O)(OR°)$_2$; SiR°$_3$; —(C$_{1-4}$ straight or branched)alkylene)O—N(R°$_2$; or —(C$_{1-4}$ straight or branched)alkylene)C(O) ON—(R°$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, NO$_2$, SiR$^\bullet_3$, OSiR$^\bullet_3$, C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable hydroxyl protecting groups include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Antibody—As used herein the term "antibody" includes monoclonal antibodies, polyclonal antibodies, monospecific antibodies, and multispecific antibodies (e.g., bispecific antibodies) and the term "antibody" is used interchangeably with the terms "immunoglobulin," "immunoglobulins" and "immunoglobulin molecule". Each antibody molecule has a unique structure that allows it to bind its specific antigen, but all antibodies have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD and IgE, respectively. Thus, an antibody as defined herein can be of any type or class (e.g., IgG, IgE, IgM, IgD, and IgA) or subclass (e.g., IgG1, IgG2, IgG3, IgG4, IgA1 and IgA2).

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3 and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multi specific antibodies (for example, bispecific antibodies), and antibody fragments so long as they contain or are modified to contain at least the portion of the $C_H2$ domain of the heavy chain immunoglobulin constant region which comprises an N-linked glycosylation site of the $C_H2$ domain, or a variant thereof. Included within the terms are molecules comprising at least the Fab region.

The term "antibodies" further includes chemical analogues and derivatives of antibodies and antibody fragments, provided that the antibody or antibody fragment maintains its ability to bind specifically to its target antigen. Thus, for example, chemical modifications are possible (e.g., glycosylation, acetylation, PEGylation and other modifications without limitation) provided specific binding ability of the antibody is retained. An antibody may be, for example, human, humanized, or chimeric A "monoclonal antibody" is an antibody obtained from a population of substantially homogeneous antibodies, i.e., individual antibodies comprising the population are identical except for possible naturally-occurring mutations that may be present in minor amounts. Monoclonal antibodies (mAbs) are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be synthesized by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567 to Cabilly et al.).

Monoclonal antibodies further include chimeric antibodies in which a portion of the heavy and/or light chain is identical to or homologous with the corresponding s of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one that comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains such as human native sequence constant domains or amino acid sequence variants thereof. An intact antibody may or may not have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, camelids, or an epitope-binding fragments of any of the above which immunospecifically bind to a target antigen (e.g., a cancer cell antigen).

"Humanized" forms of non-human (e.g., rodent) antibodies are chimeric antibodies that contain minimal sequence derived from non-human immunoglobulin.

The term "capable of specific binding" refers to protein or peptide (e.g., antibody) binding to a predetermined target substance (e.g., an antigen and/or groups of antigens), e.g. a target substance that is expressed on the surface of a cell; thus the term "binding to a target cell" or "binding to a cancer cell" is to be understand as referring to protein or peptide (e.g., antibody) binding to a predetermined target substance (e.g. antigen or antigens) that is expressed on such a cell.

Typically, the protein or peptide (e.g., antibody) binds with an affinity of at least about $1\times10^7 M^1$, and/or binds to the predetermined target substance (e.g., antigen, antigens or cell) with an affinity that is at least two-fold greater than its affinity for binding to a non-specific control substance (e.g., BSA, casein, non-cancer cells) other than the predetermined target substance or a closely-related target substance.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, glucocorticoids and analogs thereof, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes, cancer, inflammatory disease), a symptom or symptoms of a condition (e.g., hyperglycemia), or the predisposition toward a condition.

DETAILED DESCRIPTION OF THE INVENTION

The present invention provides phosphonate-based linkers comprising a monophosphonate, diphosphonate, triphosphonate, or tetraphosphonate group having the general formula

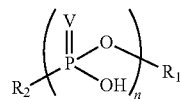

Wherein R1 is a first linker arm comprising a tuning element, an optional spacer element, and a reactive functional group capable of reacting with a group on a ligand or targeting moiety in which the tuning element is linked to the O group of the phosphonate group; and, R2 is a second linker arm comprising a payload linked to the P atom of the phosphonate group via a linker, V is selected from O or S, and wherein n=1, 2, 3, or 4. Interspersed between the tuning element and the reactive functional group of the linker arm may be an optional spacer element.

In general, the phosphonate-based linker comprises a compound that has the following formula (I)

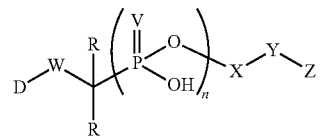

Wherein V is selected from O and S; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadiene, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In a further embodiment, the reactive functional group at the proximal end of the payload-phosphonate-based linker may be covalently linked to a ligand or targeting moiety to provide a conjugate wherein in particular embodiments, the ligand is capable of targeting the conjugate to a particular cellular target when administered to a subject in need of the payload. Such a compound comprises formula (II)

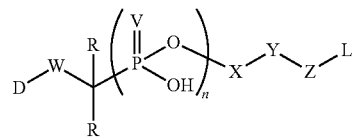

Wherein V is selected from O and S; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin K sensitive group, or glycosidase sensitive group; Y is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4.

In particular embodiments, the payload-ligand conjugate compound comprising a cell-specific targeting ligand conjugated to a drug moiety comprises the formula (III)

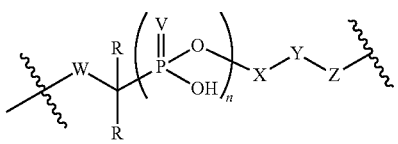

where the wavy lines indicate the covalent attachment sites to the cell-specific targeting ligand and the payload and wherein V is selected from O and S; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on the cell-specific targeting ligand; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In particular embodiments, the phosphonate-based linker comprises a compound that has the following formula (IV)

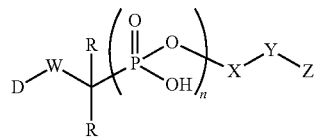

Wherein W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In a further embodiment, the reactive functional group at the proximal end of the payload-phosphonate-based linker may be covalently linked to a ligand or targeting moiety to provide a conjugate wherein in particular embodiments, the ligand is capable of targeting the conjugate to a particular cellular target when administered to a subject in need of the payload. Such a compound comprises formula (V)

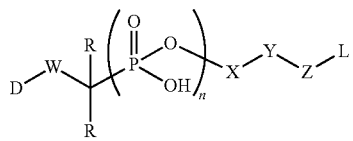

Wherein; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin K sensitive group, or glycosidase sensitive group; Y is selected from a covalent bond or a bivalent, straight or branched, saturated or unsaturated, optionally substituted C$_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4.

In particular embodiments, the payload-ligand conjugate compound comprising a cell-specific targeting ligand conjugated to a drug moiety comprises the formula (VI)

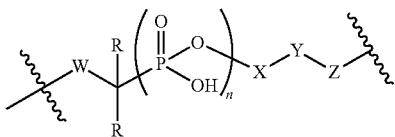

where the wavy lines indicate the covalent attachment sites to the cell-specific targeting ligand and the payload; W is selected from a bivalent, straight or branched, saturated or unsaturated, optionally substituted C$_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted C$_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on the cell-specific targeting ligand; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In particular embodiments, the phosphonate-based linker comprises a compound that has the following formula (VII)

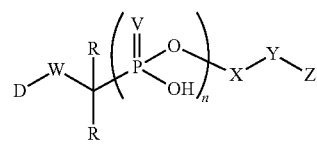

Wherein W is selected from a bivalent, straight or branched, saturated or unsaturated, optionally substituted C$_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted C$_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In a further embodiment, the reactive functional group at the proximal end of the payload-phosphonate-based linker may be covalently linked to a ligand or targeting moiety to provide a conjugate wherein in particular embodiments, the ligand is capable of targeting the conjugate to a particular cellular target when administered to a subject in need of the payload. Such a compound comprises formula (VIII)

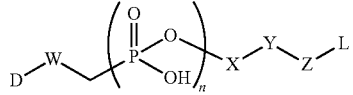

Wherein; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin K sensitive group, or glycosidase sensitive group; Y is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4.

In particular embodiments, the payload-ligand conjugate compound comprising a cell-specific targeting ligand conjugated to a drug moiety comprises the formula (IX)

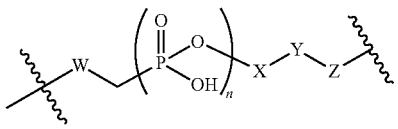

where the wavy lines indicate the covalent attachment sites to the cell-specific targeting ligand and the payload; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on the cell-specific targeting ligand; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In particular embodiments, the phosphonate-based linker is a compound that has the following formula (X)

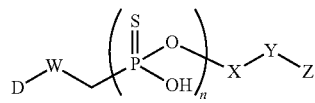

Wherein W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In a further embodiment, the reactive functional group at the proximal end of the payload-phosphonate-based linker may be covalently linked to a ligand or targeting moiety to provide a conjugate wherein in particular embodiments, the ligand is capable of targeting the conjugate to a particular cellular target when administered to a subject in need of the payload. Such a compound comprises formula (XI)

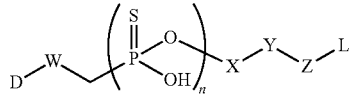

Wherein; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin K sensitive group, or glycosidase sensitive group; Y is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; D is a payload; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and n is 1, 2, 3, or 4.

In particular embodiments, the payload-ligand conjugate compound comprising a cell-specific targeting ligand conjugated to a drug moiety comprises the formula (XII)

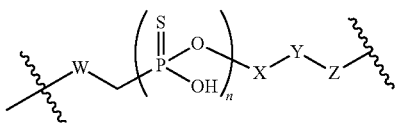

where the wavy lines indicate the covalent attachment sites to the cell-specific targeting ligand and the payload; W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on the cell-specific targeting ligand; each occurrence of R is independently hydrogen, a suitable protecting group, an acyl moiety, arylalkyl moiety, aliphatic moiety, aryl moiety, heteroaryl moiety, or heteroaliphatic moiety; and n is 1, 2, 3, or 4.

In particular embodiments, the phosphonate-based linker comprises a compound that has a formula selected from

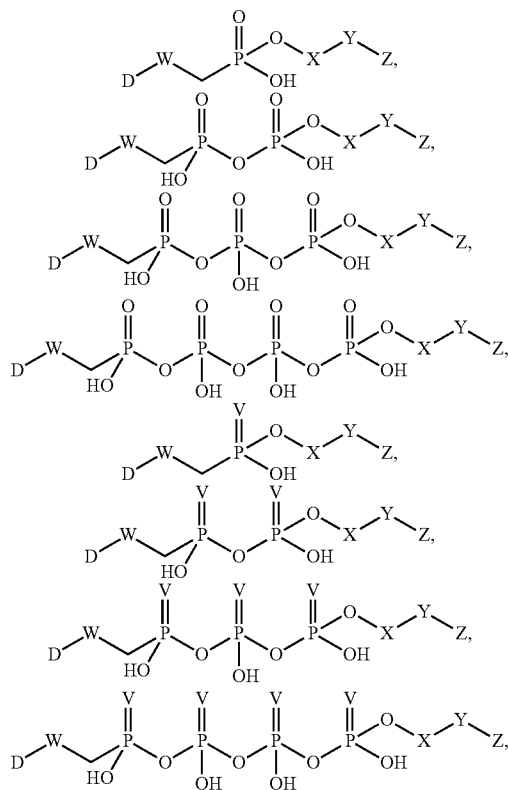

wherein W is selected from a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted $C_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S; D is a payload; each occurrence of R is independently hydrogen, a suitable protecting group, an acyl moiety, arylalkyl moiety, aliphatic moiety, aryl moiety, heteroaryl moiety, or heteroaliphatic moiety; and each V is independently O or S.

In particular embodiments, the phosphonate-based linker comprises a compound that has a formula selected from

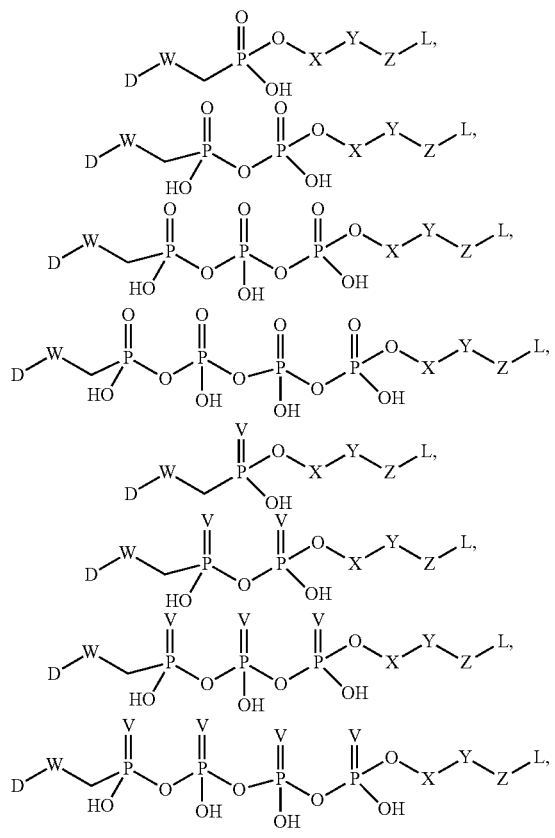

wherein W is selected from a bivalent, straight or branched, saturated or unsaturated, optionally substituted C$_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; X is a tuning element selected from a covalent bond; a carbon atom; a heteroatom; an optionally substituted group selected from the group consisting of acyl, aliphatic, heteroaliphatic, aryl, heteroaryl, and heterocyclic; nucleoside, protease sensitive group, cathepsin B sensitive group, or glycosidase sensitive group; Y is optional but when present is selected from a covalent bond or a bivalent, straight or branched, saturated or unsaturated, optionally substituted C$_{1-30}$ hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group; Z is a linkage formed between (i) a reactive functional group selected from the group consisting of N-hydroxysuccinimide, para-nitrophenyl carbonate, para-nitrophenyl carbamate, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S, and (ii) an S, NR, or O group on L; each occurrence of R is independently hydrogen, a suitable protecting group, an acyl moiety, arylalkyl moiety, aliphatic moiety, aryl moiety, heteroaryl moiety, or heteroaliphatic moiety; L is a cell-specific targeting ligand; and each V is independently O or S.

In particular aspects of the above wherein Z is a reactive group, Z may have the structure

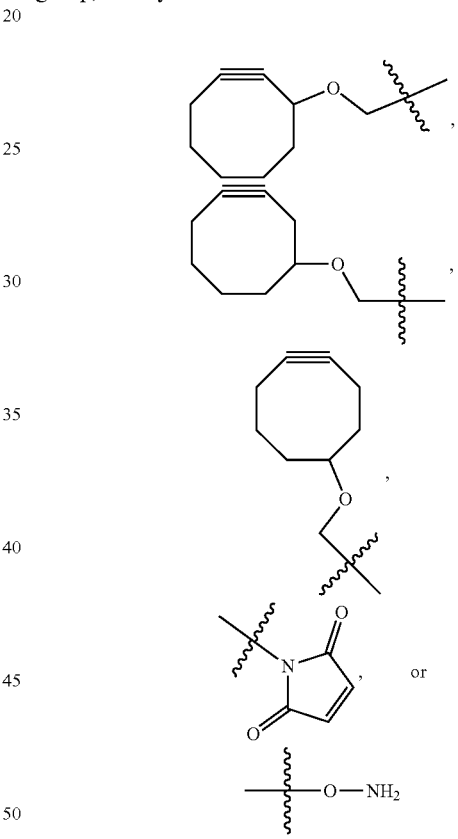

wherein the wavy line marks the covalent bond between Z and Y, or X when Y is a covalent bond.

In particular aspects, the linkage Z when conjugated to a cell-specific targeting ligand L, Z may have the structure

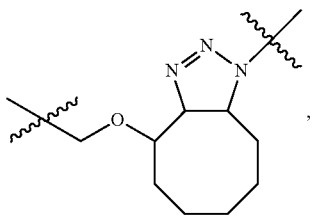

-continued

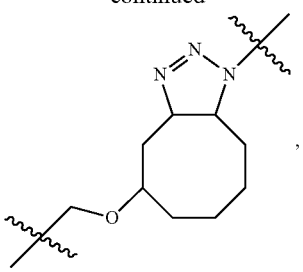,

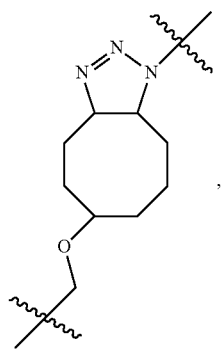,

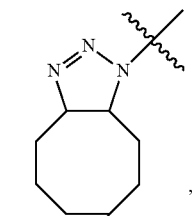,

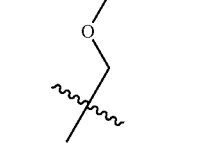,

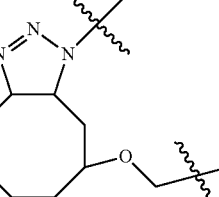,

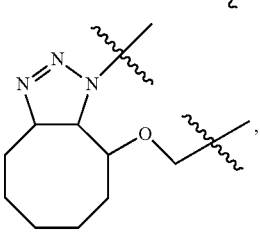,

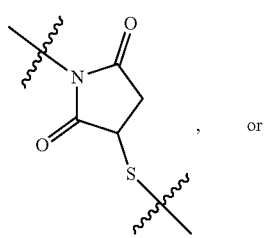 or

-continued

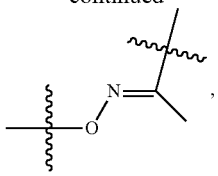, wherein the wavy lines mark the covalent bond between Z and Y, or X when Y is a covalent bond on the left and Z and L on the right.

The O—X linkage of the phosphonate group is stabile extracellularly and labile intracellularly, for example, when present in the lysosomal compartment of the target cell the O—X linkage is cleaved. However, the phosphonate-W-payload linkage is stable both intracellularly and extracellularly. When the phosphonate group is cleaved intracellularly, the payload-W is released with the W attached to a monophosphonate group, which renders the payload charged or polar and facilitates retention of the payload within the cell. This is illustrated schematically below wherein n=1, 2, 3, or 4 and the other constituents are as above.

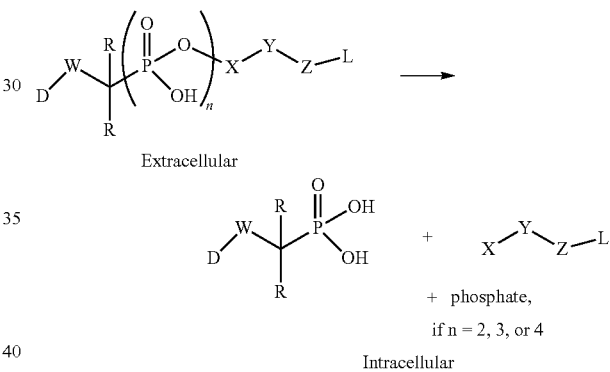

It should be noted that even in the case where the conjugate comprises a diphosphonate, triphosphonate, or tetraphosphonate, upon intracellular cleavage, the payload-W is released with the W linked to a monphosphonate.

The tuning element provides a tunable stability to the phosphonate linkage when the conjugate is within the lysosomal compartment of the target cell. The intracellular stability of the phosphonate group or rate of intracellular release of the payload from the conjugate may be adjusted or tuned by the particular tuning element adjacent to the phosphonate group and/or by adjusting the number of the phosphonate groups. The conjugates disclosed herein are particularly useful in embodiments in which the ligand is an antibody or antibody fragment and the payload is a therapeutic agent, for example, a cytotoxin or a glucocorticoid receptor agonist, which herein is referred to as an "antibody drug conjugate" or "ADC".

The link between the antibody and the drug moiety plays an important role in an antibody drug conjugate (ADC), as the type and structure of the linker may significantly affect the potency, selectivity, and the pharmacokinetics of the resulting conjugate (Widdeson et al, J. Med. Chem. 49: 4392-4408 (2006); Doronina et al., Bioconj. Chem. 17: 114-124 (2006); Hamann et al., Bioconj. Chem. 16: 346-353 (2005); King et al., J. Med. Chem. 45: 4336-4343 (2002);

Alley et al., Bioconj. 19: 759-765 (2008); Blattler et al., Biochem. 24: 1517-1524 (1985). ADC delivery of a drug moiety to its intracellular target occurs via a multistep sequence of events: binding to the cell surface, endocytosis, trafficking (within an endosome) to a lysosome, proteolytic degradation of the conjugate, and diffusion of the released drug moiety across the lysosomal or endosomal membrane toward its intracellular target and its interaction with the target. Therefore, the linker should be sufficiently stable while in circulation to allow delivery of the intact ADC to the target cell but, on the other hand, sufficiently labile to allow release of the drug moiety from the ADC once inside the targeted cell. In general, four types of linkers have been used for preparation of ADCs that have currently entered the clinic: (a) acid-labile linkers, exploiting the acidic endosomal and lysosomal intracellular microenvironment (Hamann et al., op. cit.; Blattler et al., op. cit.); (b) linkers cleavable by lysosomal proteases (Dronina et al. op. cit.; King et al. op. cit.); (c) chemically stable thioether linkers that release a lysyl adduct after proteolytic degradation of the antibody inside the cell; (Lewis et al Cancer Res. 68: 9280-9290 (2008); Erickson et al., Cancer Res. 66: 4426-4433 (2006) and (d) disulfide containing linkers (Chari, Adv. Drug Delivery Rev. 31: 89-104 (1998); Widdeson et al., op. cit.), which are cleaved upon exposure to an intracellular thiol. While U.S. Pat. No. 5,094,848 discloses conjugates comprising a diphosphate or amidated diposphate group and a linker arm wherein the linker arm may preferably be an oligopeptide having preferably 2-10 amino acids, in particular embodiments the tuning element of the phosphate-based linkers disclosed herein may include a di-peptide.

The payload-linker conjugates of the present invention wherein the payload is covalently linked to a tuning element of the linker via a monophosphonate, diphosphonate, triphosphonate, or tetraphosphonate linkage have a differentiated and tunable stability of the phosphonate linkage in blood vs. an intracellular environment (e.g. lysosomal compartment). Due to location of enzymes that recognize the phosphonate linkage, conjugates that have a phosphonate group linking a payload to a tuning element of the linker are stable in circulation (plasma or blood) but reactive in intracellular compartments (e.g., lysosomes) making them suitable for intracellular delivery of payload conjugates where it desired to render the poayload charged to facilitate intracellular retention. The exemplary payload-phosphonate-based linker conjugates in the Examples show that the payload-phosphonate-based linker conjugates of the present invention are stable in blood, which is advantageous for extending the half-life and to prevent premature release of payload from the conjugates but when cleaved intracellularly provides a payload comprising the phosphonate group, which facilitates intracellular retention.

Importantly, the inventors have discovered that by modifying the tuning element and/or V and/or W, and/or the number of phosphonate groups, the ability to tune reactivity or cleavage of the phosphonate linkage in a lysosomal environment so as to release the payload-phosphonate from the conjugate. In general, the rate of release of the payload conjugated to a phosphonate group is dependent on the proximal substitution of the tuning element. The ability to cleave the linkage between the phosphonate and the tuning element efficiently in a lysosome is advantageous for the release of the payload from the conjugate once it has been delivered to a cell and internalized through an endosomal pathway. In addition, the excellent solubility of the payload-phosphonate-based linker facilitates conjugation to a ligand or cell-targeting moiety and minimizes aggregation of the conjugates. In addition, the phosphonate contributes to retention of the payload to the conjugate within cell and limits permeability of conjugates containing the payload from entering non-target cells.

The phosphonate-based linkers provide greater solubility relative to disulfide linkers, cathepsin B-cleavable linkers, esters and acid-sensitive linkers such as hydrazones. They enable the release of the payload conjugated to a phosphonate unlike some of the alternative linkers, and may offer an improved blood/lysosome stability profile.

Specifically, these phosphonate-based linkers will provide superior blood stability relative to esters and disuflides. Phosphonate-based linkers, following lysosomal cleavage will release a phosphonate-containing payload. The enzymatic hydrolysis of the phosphonate may be more rapid than the acid-hydrolysis of hyrdazones. The phosphonate-based linkers disclosed herein minimize the propensity for conjugates comprising particular payloads to aggregate. For example, antibody-drug conjugates comprising duocarmycin are known to have a propensity to aggregate. However, antibodies conjugated to duocarmycin via a phosphonate-based linker disclosed herein did not produce detectable aggregates. Thus, the phosphonate-based linkers disclosed herein are particularly useful for conjugating payloads that are prone to forming aggregates to a cell-specific targeting ligand to provide a conjugate with a reduced or no detectable propensity for aggregation.

Thus, the phosphonate-based linkers disclosed herein provide an ideal design for antibody-drug conjugates and the like.

Phosphonate Group

The phosphonate group comprising the phosphonate-based linkers disclosed herein may comprise 1, 2, 3, or 4 phosphate atoms. In particular embodiments, the phosphonate group may be a phosphonate

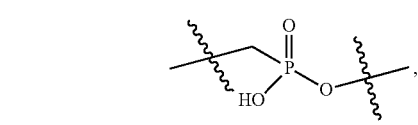 [SMILES: *CP(=O)(O)O*]

a diposphonate

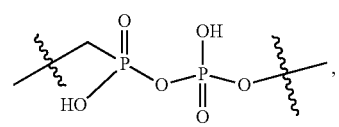 [SMILES: *CP(=O)(O)OP(=O)(O)O*]

a triphosphonate

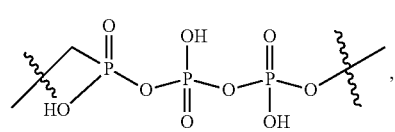 [SMILES: *CP(=O)(O)OP(=O)(O)OP(=O)(O)O*]

tetraphosphonate

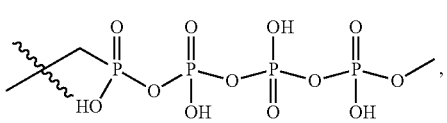 [SMILES: *CP(=O)(O)OP(=O)(O)OP(=O)(O)OP(=O)(O)OC]

a phosphorthionate

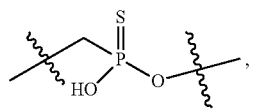 [SMILES: *CP(O)(=S)O*]

or a diphosphorthionate

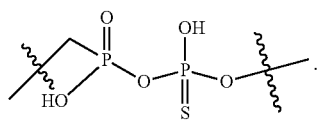 [SMILES: *CP(=O)(O)OP(O)(=S)O*]

The wavy lines shown indicate the bond between the P and a linker W connected to a payload (left) and the bond between the O and the tuning element on the proximal end (right).

Payload

Payloads, depicted as "D" herein, are provided in the current invention as part of a payload-ligand conjugate where the payload is linked to a ligand via a phosphonate-based linker comprising reactive functional group selected from the group consisting of N-hydroxysuccinimidyl ester, para-nitrophenyl carbonate, para-nitrophenyl carbamate, azide, hydrazine, pentafluorophenyl, haloacetamide, maleimide, hydroxylamine, strained cycloalkyne, and heterocycloalkyne, alkyne, diene, azadiene, and heterocyclic azadience, wherein halo is iodine (I), bromine (Br), fluorine (F), or chlorine (Cl) and hetero is N, O, or S. The payload must possess a desired biological activity and contain a reactive functional group capable of forming a covalent linkage to the linker that attached to the phosphonate group. The desired biological activity includes the diagnosis, cure, mitigation, treatment, or prevention of disease in an animal such as a human. Thus, so long as it has the needed reactive functional group, the term "payload" refers to chemicals recognized as drugs in the official United States Pharmacopeia, official Homeopathic Pharmacopeia of the United States, or official National Formulary, or any supplement thereof. Exemplary drugs are set forth in the Physician's Desk Reference (PDR) and in the Orange Book maintained by the U.S. Food and Drug Administration (FDA). New drugs are being continually being discovered and developed, and the present invention provides that these new drugs may also be incorporated into the payload-ligand complex of the current invention. In particular embodiments, the functional groups on the drug include primary or secondary amines, hydroxyls, sulfhydryls, carboxyls, aldehydes, and ketones. The drug must have at least one, but may have 2, 3, 4, 5, 6 or more reactive functional groups. The payload may also be a biomolecule such as a peptide, polypeptide, or protein; a nucleic acid molecule or analog thereof, a carbohydrate, polysaccharide, a saccharide, or any other therapeutic agent that has a biological effect.

The payload-ligand conjugate is effective for the usual purposes for which the corresponding drugs are effective, but have superior efficacy because of the ability, inherent in the ligand, to transport the drug to the desired cell where it is of particular benefit. Exemplary drugs include proteins, peptides, and small molecule drugs containing a functional group for linkage to the phosphonate moiety of the linker. More specifically, these drugs include, for example, the enzyme inhibitors such as dihydrofolate reductase inhibitors, and thymidylate synthase inhibitors, DNA intercalators, glutocorticoid receptor agonists, nuclear recemptor agonists, antinflammatory agents, DNA cleavers, topoisomerase inhibitors, the anthracycline family of drugs, the vinca drugs, the mitomycins, the bleomycins, the cytotoxic nucleosides, the pteridine family of drags, diynenes, the podophyllotoxins, differentiation inducers, and taxols.

In one embodiment, the drugs of the current invention include cytotoxic drugs useful in cancer therapy and other small molecules, proteins or polypeptides with desired biological activity, such as a toxin. The drug may be selected to be activated at a tumor cells by conjugation to a tumor-specific ligand. These tumor specific drug-ligand conjugates have tumor specificity arising from the specificity of the ligand. Examples of this are drug-ligand conjugates that are highly selective substrates for tumor specific enzymes, where these enzymes are present in the proximity of the tumor in sufficient amounts to generate cytotoxic levels of free drug in the vicinity of the tumor.

Cytotoxic drugs useful in the current invention include, for example, duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclopropa[c]benz[e]-indol-4-one)-based analogues of the duocarmycins and CC-1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-I, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloro methotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, carminomycin, aminopterin, tallysomycin, podophyllotoxin and podophyllotoxin derivatives such as etoposide or etoposide phosphate, vincristine, taxol, taxotere retinoic acid, butyric acid, N-acetyl spermidine, camptothecin, and their analogues.

Anti-inflammatory agents, such as glucocorticoid receptor agonists include glucocorticoids such as Cortisol, cortisone acetate, beclometasone, prednisone, prednisolone, methylprednisolone, betamethasone, trimcinolone, budesonide, dexamethasone, fluticasone, fluticasone propionate, fluticasone furoate, or mometasone.

Linker Arms

The phosphonate-based linkers disclosed herein comprise a first arm comprising a tuning element having a distal end and a proximal end wherein the distal end is covalently linked to an oxygen atom of the phosphonate group and the proximal end is covalently linked to a functional reactive group capable of covalent linkage to a cell-targeting ligand and a second arm comprising a linker having a distal end and a proximal end wherein the distal end is covalently linked to a payload or drug and a proximal end covalently linked to a phosphorus atom of the phosphonate group. Optionally, the linker arm may further include a spacer element interposed between the tuning element and the reactive functional group.

Examples of tuning elements comprising the first arm include but are not limited to

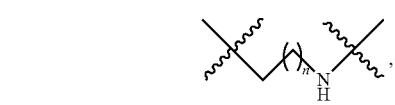
n = 0 - 5
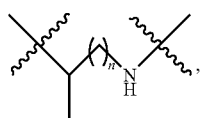
n = 0 - 5
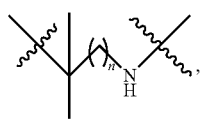
n = 0 - 5
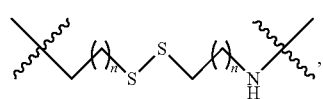
n = 0 - 5
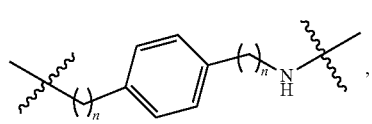
n = 0 - 5
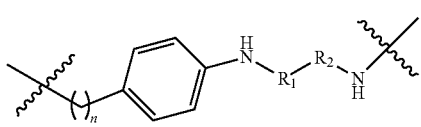
n = 0 - 5
$R_1$ and $R_2$ each independently any amino acid
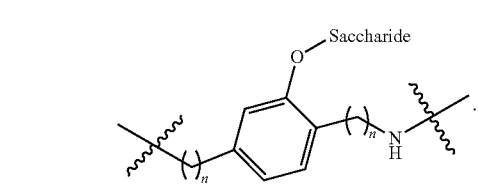
n = 0 - 5
The wavy lines indicate the covalent attachment sites to an oxygen atom of the phosphonate group at the distal end (left) and the functional reactive group on the proximal end (right), or optionally, a spacer element.
Further examples of tuning elements include but are not limited to
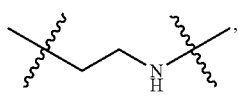
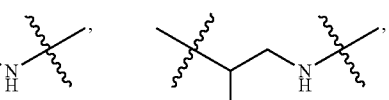
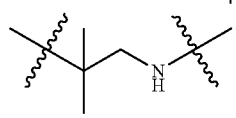
-continued
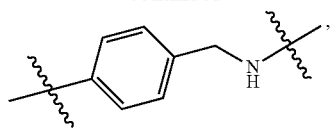
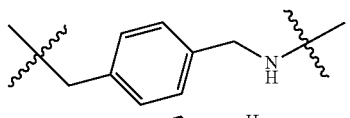
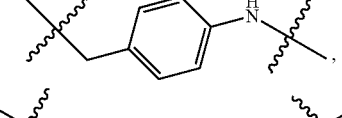
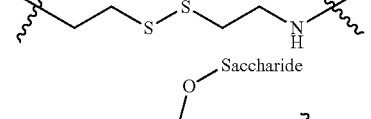
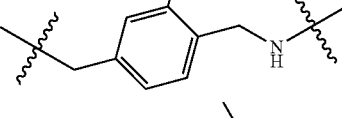
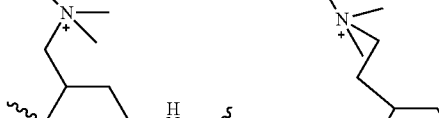
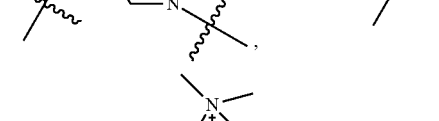
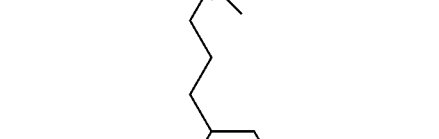
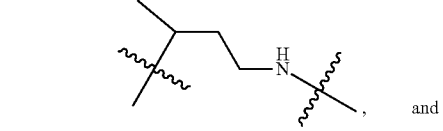
and

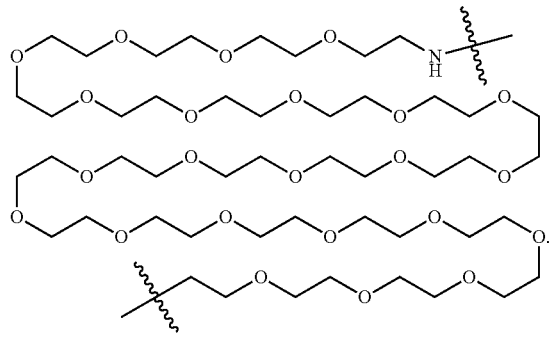

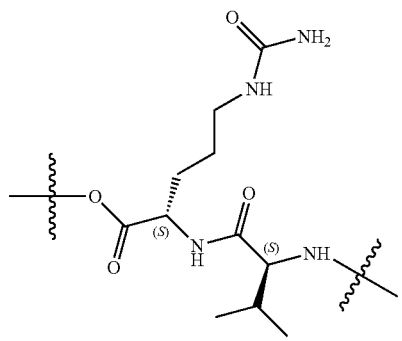

The wavy lines indicate the covalent attachment sites to an oxygen atom of the phosphonate group at the distal end (left) and the functional reactive group on the proximal end (right), or optionally, a spacer element.

In general, the spacer element is to allow for distance control away from the cell-targeting ligand. In some embodiments, this distance may have an impact on the stability/cleavability of the linker. The spacer element may be selected from a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group. In particular aspects, the spacer element may be a straight polyethylglycol (PEG) chain (of a defined length, for example 1, 2, 3, 4, 5, 6, 7, 8, 9, 10, or more polyethylene groups) and straight carbon chains of C1-30 hysdrocarbons with or without solubilizing groups attached thereto.

In general, the linker comprising the second arm is to allow for distance control away from the phosphonate group. In some embodiments, this distance may have an impact on the efficacy of the payload or drug. The linker may be selected from a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group. In particular aspects, the linker may be a straight polyethylglycol (PEG) chain (of a defined length, for example 1, 2, 3, 4, 5, 6, 7, 8, 9, 10, or more polyethylene groups) and straight carbon chains of C1-30 hysdrocarbons with or without solubilizing groups attached thereto.

In general, the spacer element is to allow for distance control away from the cell-targeting ligand. In some embodiments, this distance may have an impact on the stability/cleavability of the linker. Examples of spacer elements include straight polyethylglycol (PEG) chains (of a defined length), straight carbon chains with or without solubilizing groups attached thereto, a dipeptide, a tripeptide, a tetrapeptide, an enzyme cleavage site, for example a cathepsin cleavage site having the structure wherein the wavy line on the left marks the covalent bond to an atom in the tuning element and the wavy line on the right marks the covalent bond to an atom of a reactive group Z.

Targeting Ligand

The phosphonate linker and payload may be linked to a targeting ligand that selectively delivers a pay load to a cell, organ, or region of the body. Exemplary targeting ligands such as antibodies (e.g., chimeric, humanized and human), ligands for receptors, lectins, saccharides, and the like are recognized in the art and are useful without limitation in practicing the present invention. Other targeting ligands include a class of compounds that do not include specific molecular recognition motifs include macromolecules such as poly(ethylene glycol), polysaccharide, polyamino acids and the like, which add molecular mass to the cytotoxin. The additional molecular mass affects the pharmacokinetics of the payload, e.g., serum half-life.

In an exemplary embodiment, the invention provides a payload, linker or payload-linker conjugate with a targeting ligand that is a biomolecule, e.g., an antibody, receptor, peptide, lectin, saccharide, nucleic acid or a combination thereof. Biomolecules useful in practicing the present invention may be derived from any source. The biomolecules may be isolated from natural sources or may be produced by synthetic methods. Proteins may be natural proteins or mutated proteins. Mutations may be effected by chemical mutagenesis, site-directed mutagenesis or other means of inducing mutations known to those of skill in the art. Proteins useful in practicing the instant invention include, for example, enzymes, antigens, antibodies and receptors. Antibodies may be either polyclonal or monoclonal, but most preferably are monoclonal and may be human, humanized, or human chimeric antibodies. Peptides and nucleic acids may be isolated from natural sources or can be wholly or partially synthetic in origin.

In a particular embodiment, the targeting ligand is an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies that are known in the art may be used in the conjugates of the invention, in particular for the treatment of the disease with which the target antigen is associated. Non-limiting examples of target antigens (and their associated diseases) to which a conjugate of the invention may be targeted include: Her2 (breast cancer), CD4 (lymphomas, autoimmune diseases, including rheumatoid arthritis), CD20 (lymphomas), EGFR (solid tumors), CD22 (lymphomas, including non-Hodgkin's lymphoma), CD23 (asthma), CD25, CD52 (chronic lymphocytic leukemia), CD30 (lymphomas, including non-Hodgkin's lymphoma), CD33 (acute myelogenous leukemia), CD40L (immune thrombocytopenic purpura), CD70, CD74, CD80 (psoriasis), CD163, Mucl8 (melanoma), integrins (solid tumors), PSMA (prostate cancer, benign prostatic hyperplasia), CEA (colorectal cancer), CD1 Ia (psoriasis), CTLA4 (T cell lymphomas) and BLys (autoimmune diseases, including systemic lupus erythematosus).

Targeting ligands may be attached to the linker arm by any available reactive group that can react with the reactive functional group on the proximal end of the linker arm. For example, peptides and proteins may be attached through an amine, carboxyl, sulfhydryl, or hydroxyl group. Such a group may reside at a peptide terminus or at a site internal to the peptide chain. Nucleic acids may be attached through a reactive group on a base (e.g., exocyclic amine) or an available hydroxyl group on a sugar moiety (e.g., 3'- or 5'-hydroxyl). The peptide or protein may be further derivatized at one or more sites to allow for the attachment of appropriate reactive groups onto the peptide or protein. See, Chrisey et al. Nucleic Acids Res. 24:3031-3039 (1996). In addition, the protein or peptide may be synthesized to contain one or more nonnatural amino acids which may then serve as a site for attachment of the linker arm comprising the payload-phosphonate-based linker. Antibodies comprising nonnatural amino acids for conjugation and methods for making such antibodies have been disclosed in U.S. Pat. No. 7,632,924.

In particular aspects, an anti-inflammatory therapeutic agent may be linked by the phophonate linker disclosed herein to an antibody that selectively delivers the therapeutic agent to a cell, organ, or region of the body that expresses the human CD25 protein, human CD74 protein, human CD74 protein, or human CD163 protein. Antibodies may be either polyclonal or monoclonal, but most preferably are monoclonal and may be human, humanized, or human chimeric antibodies. The antibody may be of any type or class (e.g., IgG, IgE, IgM, IgD, and IgA) or subclass (e.g., IgG1, IgG2, IgG3, IgG4, IgA1 and IgA2). The term "CD" refers to "cluster of differentiation".

In one embodiment, the IgG4 constant domain can differ from the native human IgG4 constant domain (Swiss-Prot Accession No. P01861.1) at a position corresponding to position 228 in the EU system and position 241 in the KABAT system, wherein the native serine at position 108 (Ser108) of the HC constant domain is replaced with proline (Pro), in order to prevent a potential inter-chain disulfide bond between the cysteine at position 106 (Cys106) and the cysteine at position 109 (Cys109), which correspond to to positions Cys226 and Cys229 in the EU system and positions Cys239 and Cys242 in the KABAT system) that could interfere with proper intra-chain disulfide bond formation. See Angal et al. Mol. Imunol. 30:105 (1993); see also (Schuurman et. al., Mol. Immunol. 38: 1-8, (2001); SEQ ID NOs:14 and 41). In other instances, a modified IgG1 constant domain which has been modified to reduce effector function can be used, for example, the IgG1 isotype may include substitutions of IgG2 residues at positions 233-236 and IgG4 residues at positions 327, 330 and 331 to greatly reduce ADCC and CDC (Armour et al., Eur J Immunol. 29(8):2613-24 (1999); Shields et al., J Biol Chem. 276(9): 6591-604 (2001)). In another embodiment, the IgG HC is modified genetically to lack N-glycosylation of the asparagine (Asn) residue at around position 297. The consensus sequence for N-glycosylation is Asn-Xaa-Ser/Thr (wherein Xaa is any amino acid except Pro); in IgG1 the N-glycosylation consensus sequence is Asn-Ser-Thr. The modification may be achieved by replacing the codon for the Asn at position 297 in the nucleic acid molecule encoding the HC with a codon for another amino acid, for example Gln. Alternatively, the codon for Ser may be replaced with the codon for Pro or the codon for Thr may be replaced with any codon except the codon for Ser. Such modified IgG1 molecules have little or no detectable effector function. Alternatively, all three codons are modified.

The antibody may be attached to the first linker arm by any available reactive group that can react with the reactive functional group on the proximal end of the first linker arm. For example, the antibody may be attached through an amine, carboxyl, sulfhydryl, or hydroxyl group. Such a group may reside at N-terminus or at a site internal to the protein chain, for example, the side chain of an amino acid. The antibody may be further derivatized at one or more sites to allow for the attachment of appropriate reactive groups onto the peptide or protein. See, Chrisey et al. Nucleic Acids Res. 24:3031-3039 (1996). In addition, the antibody may be synthesized to contain one or more non-natural amino acids, the side chain thereof which may then serve as a site for attachment of the linker arm comprising the payload-phosphate-based linker. Antibodies comprising non-natural amino acids for conjugation and methods for making such antibodies have been disclosed in U.S. Pat. No. 7,632,924, which is incorporated herein by reference. As exemplified herein the antibody may comprise a substitution of an amino acid residue in the heavy chain or light chain with the non-natural amino acid para-azidophenylalanine (pAzF). The azido group on the side chain of the pAzF residue may be conjugated to a reactive functional group of the therapeutic agent-linker such as a strained cycloalkyne, for example, cyclooctyne.

In particular aspects, the antibody is a chimeric, humanized, or fully human anti-CD25 antibody comprising the light chain CDR sequences CDR1 (RASQSVSSSYLA; SEQ ID NO: 1), CDR2 (GASSRAT; SEQ ID NO: 2), and CDR3 (QQYSSSPLT; SEQ ID NO: 3) and the heavy chain complementarity-determining region (CDR) sequences CDR1 (RYIIN; SEQ ID NO: 4), CDR2 (RIIPILGVENYAQKFQG; SEQ ID NO: 5), and CDR3 (KDWFDY; SEQ ID NO: 6). In particular aspects, the antibody is a chimeric, humanized, or fully human anti-CD25 antibody comprising the light chain CDR sequences CDR1 (RASQSVSSSFLA; SEQ ID NO: 1), CDR2 (GASSRAT; SEQ ID NO: 2), and CDR3 (QQYSSSPLT; SEQ ID NO: 3) and the heavy chain complementarity-determining region (CDR) sequences CDR1 (RYPIN; SEQ ID NO: 7), CDR2 (RIIPILGIADYAQRFQG; SEQ ID NO: 8), and CDR3 (RDWGDY; SEQ ID NO: 9). In particular aspects, the antibody is a chimeric, humanized, or fully human anti-CD25 antibody comprising the light chain CDR sequences CDR1 (RASQSGSSSYLA; SEQ ID NO: 1), CDR2 (GASSRAT; SEQ ID NO: 2), and CDR3 (QQYGSSPIT; SEQ ID NO:10) and the heavy chain complementarity-determining region (CDR) sequences CDR1 (RYAIN; SEQ ID NO:11), CDR2 (RIIPILDIADYAQKFQD; SEQ ID NO:12), and CDR3 (KDWFDP; SEQ ID NO:13). In particular aspects, the antibody is a chimeric, humanized, or fully human anti-CD25 antibody comprising the light chain CDR sequences CDR1 (RASQSVSSSFLA; SEQ ID NO:1), CDR2 (GASSRAT; SEQ ID NO:2), and CDR3 (QQYSSSPLT; SEQ ID NO:3) and the heavy chain complementarity-determining region (CDR) sequences CDR1 (RYPIN; SEQ ID NO:14), CDR2 (RIIPILGIADYAQRFQG; SEQ ID NO:8), and CDR3 (RDWGDY; SEQ ID NO:9). In particular aspects, the antibody is a chimeric, humanized, or fully human anti-CD25 antibody comprising at least one, two, three, four, five, or six CDR(s) having an amino acid sequence selected from SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14. In particular aspects the antibody is a chimeric, humanized, or fully human anti-CD25 antibody that competes with any one of the aforementioned antibodies for binding to the CD25. The aforementioned anti-CD70 antibodies comprising said CDR sequences have been disclosed in U.S. Pat. No. 7,438,907, which is incorporated herein by reference.

In particular aspects, the antibody is a chimeric, humanized, or fully human anti-CD70 antibody comprising the light chain CDR sequences CDR1 (RASQSVSSYLA; SEQ ID NO:15), CDR2 (YDASNRAT; SEQ ID NO:16), and CDR3 (QQRTNWPLT; SEQ ID NO:17) and the heavy chain complementarity-determining region (CDR) sequences CDR1 (SYIMH; SEQ ID NO:18), CDR2 (VISYDGRNKYYADSVK; SEQ ID NO:19), and CDR3 (DTDGYDFDY; SEQ ID NO:20). In particular aspects, the antibody is a chimeric, humanized, or fully human anti-CD70 antibody comprising the light chain CDR sequences CDR1 (RASQGISSALA; SEQ ID NO:21), CDR2 (DASSLES; SEQ ID NO:22), and CDR3 (QQFNSYPFT; SEQ ID NO:23) and the heavy chain complementarity-determining region (CDR) sequences CDR1 (YYAMH; SEQ ID NO:24), CDR2 (VISYDGSIKYYADSVK; SEQ ID NO:25), and CDR3 (EGPYSNYLDY; SEQ ID NO:26). In particular aspects, the antibody is a chimeric, humanized, or fully human anti-CD70 antibody comprising the light chain CDR sequences CDR1 (RASQGISSWLA; SEQ ID NO:27), CDR2 (AASSLQS; SEQ ID NO:28), and CDR3 (QQYNSYPLT; SEQ ID NO:29) and the heavy chain complementarity-determining region (CDR) sequences CDR1 (DYGMH; SEQ ID NO:30), CDR2 (VIWYDGSNKYYADSVK; SEQ ID NO:31), and CDR3 (DSIVMVRGDY; SEQ ID NO:32). In particular aspects, the antibody is a chimeric, humanized, or fully human anti-CD70 antibody comprising the light chain CDR sequences CDR1 (RASQGISSWLA; SEQ ID NO:33), CDR2 (AASSLQS; SEQ ID NO:34), and CDR3 (QQYNSYPLT; SEQ ID NO:35) and the heavy chain complementarity-determining region (CDR) sequences CDR1 (DHGMH; SEQ ID NO:36), CDR2 (VIWYDGSNKYYADSVK; SEQ ID NO:37), and CDR3 (DSIMVRGDY; SEQ ID NO:38). In particular aspects, the antibody is a chimeric, humanized, or fully human anti-CD70 antibody comprising the light chain CDR sequences CDR1 (RASQSVSSYLA; SEQ ID NO:15), CDR2 (DASNRAT; SEQ ID NO:39), and CDR3 (QQRSNWPLT; SEQ ID NO:40) and the heavy chain complementarity-determining region (CDR) sequences CDR1 (SDYYYWS; SEQ ID NO:41), CDR2 (YIYYSGSTNYDPSLKS; SEQ ID NO:42), and CDR3 (GDGDYGGNCFDY; SEQ ID NO:43). In particular aspects, the antibody is a chimeric, humanized, or fully human anti-CD74 antibody comprising at least one, two, three, four, five, or six CDR(s) having an amino acid sequence selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43. In particular aspects the antibody is a chimeric, humanized, or fully human anti-CD70 antibody that competes with any one of the aforementioned antibodies for binding to the CD70. The aforementioned anti-CD70 antibodies comprising said CDR sequences have been disclosed in U.S. Pat. No. 8,124,738, which is incorporated herein by reference.

In particular aspects, the antibody is a chimeric, humanized, or fully human anti-CD74 antibody comprising the light chain complementarity-determining region (CDR) sequences CDR1 (RSSQSLVHRNGNTYLH; SEQ ID NO:44), CDR2 (TVSNRFS; SEQ ID NO:45), and CDR3 (SQSSHVPPT; SEQ ID NO:46) and the heavy chain CDR sequences CDR1 (NYGVN; SEQ ID NO:47), CDR2 (WINPNTGEPTFDDDFKG; SEQ ID NO:48), and CDR3 (SRGKNEAWFAY; SEQ ID NO:49). In particular aspects, the antibody is a chimeric, humanized, or fully human anti-CD74 antibody comprising at least one, two, three, four, five, or six CDR(s) selected from SEQ ID NO:44, SEQ ID NO: 45, SEQ ID NO:46, SEQ ID NO:47, SEQ ID NO:48, and SEQ ID NO:49. In particular aspects the antibody is a chimeric, humanized, or fully human anti-CD74 antibody that competes with any one of the aforementioned antibodies for binding to the CD74. Antibodies comprising said CDR sequences have been disclosed in U.S. Pat. No. 7,772,373, which is incorporated herein by reference. In a particular aspect, the anti-CD74 antibody comprises a heavy chain (HC) comprising an amino acid sequence selected from SEQ ID NO:69, 70, 71, and 72 and a light chain (LC) comprising the amino acid sequence of SEQ ID NO:73.

In particular aspects, the antibody is a chimeric, humanized, or fully human anti-CD74 antibody comprising the light chain complementarity-determining region (CDR) sequences CDR1 (QGISSW; SEQ ID NO:50), CDR2 (AAS), and CDR3 (QQYNSYPLT; SEQ ID NO:51) and the heavy chain CDR sequences CDR1 (GFTFSSYA; SEQ ID NO:52), CDR2 (ISYDGSNK; SEQ ID NO:53), and CDR3 (ASGRYYGSGSYSSYFD; SEQ ID NO:54); or the heavy chain CDR sequences CDR1 (GFTFSSYA; SEQ ID NO:52), CDR2 (ISYDGSIK; SEQ ID NO:55), and CDR3 (ARGREYTSQNIVILLD; SEQ ID NO:56); or the heavy chain CDR sequences CDR1 (GFTFSSYA; SEQ ID NO:52), CDR2 (ISYDGSNK; SEQ ID NO:53), and CDR3 (ARGREITSQNIVILLD; SEQ ID NO:57); or the heavy chain CDR sequences CDR1 (GFTFSSYA; SEQ ID NO:52), CDR2 (IWYDGSNK; SEQ ID NO:58), and CDR3 (ARGGTLVRGAMYGTDV; SEQ ID NO:59). In particular aspects, the antibody is a chimeric, humanized, or fully human anti-CD74 antibody comprising at least one, two, three, four, five, or six CDR(s) having an amino acid sequence selected from AAS, SEQ ID NO:50, SEQ ID NO: 51, SEQ ID NO:52, SEQ ID NO:53, SEQ ID NO:54, SEQ ID NO:55, SEQ ID NO:56, SEQ ID NO:57, SEQ ID NO:58, and SEQ ID NO:59. In particular aspects the antibody is a chimeric, humanized, or fully human anti-CD74 antibody that competes with any one of the aforementioned antibodies for binding to the CD74. Antibodies comprising said CDR sequences have been disclosed in U.S. Patent Application Publication No. 20140030273, which is incorporated herein by reference. In a particular aspect, the anti-CD74 antibody comprises a heavy chain (HC) comprising an amino acid sequence selected from SEQ ID NO:74, 75, 76, and 77 and a light chain (LC) comprising the amino acid sequence of SEQ ID NO:78.

In particular aspects, the antibody is a chimeric, humanized, or fully human anti-CD163 antibody comprising the light chain CDR sequences CDR1 (ASQSVSSDV; SEQ ID NO:60), CDR2 (YAS), and CDR3 (QDYTSPRT; SEQ ID NO:61) and the heavy chain complementarity-determining region (CDR) sequences CDR1 (GYSITSDY; SEQ ID NO:62), CDR2 (YSG), and CDR3 (CVSGTYYFDYWG; SEQ ID NO:63); or the light chain CDR sequences CDR1 (ASQSVSHDV; SEQ ID NO:54), CDR2 (YTS), and CDR3 (QDYSSPRT; SEQ ID NO:65) and the heavy chain CDR sequences CDR1 (GYSITSDY; SEQ ID NO:62), CDR2 (YSG), and CDR3 (CVSGTYYFDYWG; SEQ ID NO:63). In particular aspects, the antibody is a chimeric, humanized, or fully human anti-CD163 antibody comprising at least one, two, three, four, five, or six CDR(s) having an amino acid sequence selected from YYAS, YSG, YTS, SEQ ID NO:60, SEQ ID NO: 61, SEQ ID NO:62, SEQ ID NO:63, SEQ ID NO:64, and SEQ ID NO:65. In particular aspects the antibody is a chimeric, humanized, or fully human anti-CD163 antibody that competes with any one of the aforementioned antibodies for binding to the CD163. Antibodies comprising said CDR sequences have been disclosed in U.S. Patent Application Publication No. 20120258107 and 20120276193, which are incorporated herein by reference.

In particular embodiments, the antibody has reduced effector function or lacks effector function compared to a wild-type or native IgG1 antibody. Reducing or eliminating effector function may be achieved by providing an antibody with an IgG4 framework or constant domain. In one embodiment, the IgG4 constant domain may differ from the native human IgG4 constant domain (Swiss-Prot Accession No. P01861.1) at a position corresponding to position 228 in the EU system and position 241 as determined in the KABAT numbering scheme (See, e.g., Elvin A. Kabat ((1991) Sequences of Proteins of Immunological Interest, 5th Ed. Public Health Service, National Institutes of Health, Bethesda, Md.)), where the native Ser108 is replaced with Pro, in order to prevent a potential inter-chain disulfide bond between Cys106 and Cys109 (corresponding to positions Cys226 and Cys229 in the EU system and positions Cys239 and Cys 242 in the KABAT system) that could interfere with proper intra-chain disulfide bond formation (See Angal et al. Mol. Imunol. 30:105 (1993)). In other instances, a modified IgG1 constant domain which has been modified to increase half-life or reduce effector function can be used.

In particular aspects, the antibody that has reduced or lacks effector function is an aglycosylated antibody that lacks the N-glycan at position 297 of the heavy chain (as determined using the KABAT Numbering scheme). Aglycosylated antibodies may be produced in a prokaryote expression system, for example, *E. coli*. The antibody may be encoded by a nucleic acid molecule that introduces an amino acid substitution in any of positions 297-299 of the heavy chain such that the antibody is substantially aglycosylated when the nucleic acid molecule is expressed in a mammalian cell. In IgG1, the glycosylation site is Asn297 within the amino acid sequence QYNS (SEQ ID NO:66). In other immunoglobulin isotypes, the glycosylation site corresponds to Asn297 of IgG1. For example, in IgG2 and IgG4, the glycosylation site is the asparagine within the amino acid sequence QFNS (SEQ ID NO:67). Accordingly, a mutation of Asn297 of IgG1 removes the glycosylation site in an Fc portion derived from IgG1. In one embodiment, Asn297 is replaced with Gln. In other embodiments, the tyrosine within the amino acid sequence QYNS (SEQ ID NO:66) is further mutated to eliminate a potential non-self T-cell epitope resulting from asparagine mutation. As used herein, a T-cell epitope is a polypeptide sequence in a protein that interacts with or binds an MHC class II molecule. For example, the amino acid sequence QYNS (SEQ ID NO:66) within an IgG1 heavy chain can be replaced with a QAQS (SEQ ID NO:68) amino acid sequence. Similarly, in IgG2 or IgG4, a mutation of asparagine within the amino acid sequence QFNS (SEQ ID NO:67) removes the glycosylation site in an Fc portion derived from IgG2 or IgG4 heavy chain. In one embodiment, the asparagine is replaced with a glutamine. In other embodiments, the phenylalanine within the amino acid sequence QFNS (SEQ ID NO:67) is further mutated to eliminate a potential non-self T-cell epitope resulting from asparagine mutation. For example, the amino acid sequence QFNS (SEQ ID NO:67) within an IgG2 or IgG4 heavy chain can be replaced with a QAQS (SEQ ID NO:68) amino acid sequence.

In particular aspects, the antibody comprises a substitution of one or more of the amino acids at position 318, 320, 322, 234, 235, 236, 237, or 297 of the antibody wherein the antibody with the substitution has a reduced effector function compared to an antibody comprising the native or wild-type amino acid at the position. The effector function may be binding affinity for C1q and/or binding affinity for the Fc receptor. These amino acid substitutions and their effect on reducing effector function have been disclosed in U.S. Pat. No. 5,648,260, which is incorporated herein by reference.

In particular aspects, the Fc region is modified to decrease the ability of the antibody to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

Pharmaceutical Formulations and Administration

The conjugates disclosed herein are useful for the manufacture of medicaments for the treatment of diseases or disorders such as an inflammatory disease or cancer. The conjugates disclosed herein may be formulated into pharmaceutical formulations for use in treating diseases or disorders such as an inflammatory disease or cancer.

The present invention provides a pharmaceutical formulation comprising a compound of the invention and a pharmaceutically acceptable carrier. The compounds described herein including pharmaceutically acceptable carriers such as addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

In particular embodiments, the conjugates of the invention comprising an antibody or antibody fragment as the targeting moiety are administered parenterally, more preferably intravenously. As used herein, the terms "administering" or "administration" are intended to encompass all means for directly and indirectly delivering a compound to its intended site of action. The compounds described herein, or pharmaceutically acceptable salts and/or hydrates thereof, may be administered singly, in combination with other compounds of the invention, and/or in cocktails combined with other therapeutic agents. The choice of therapeutic agents that can be co-administered with the compounds of the invention will depend, in part, on the condition being treated.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxyniethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt. The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The following examples are intended to promote a further understanding of the present invention.

Example 1

This example shows the synthesis of the C21 Analogs.

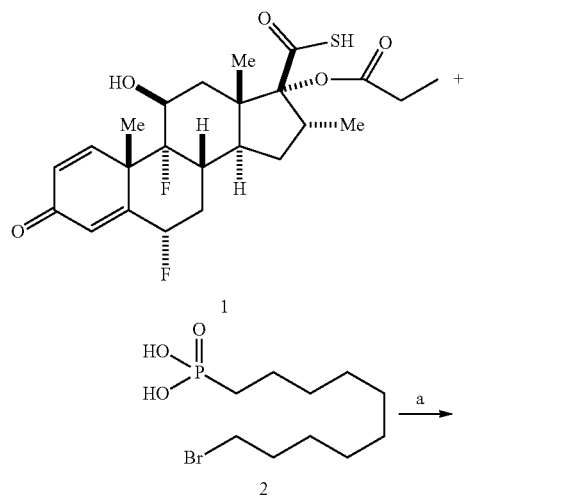

Preparation of C21 Analog (10-(((6S,8S,9R,10S,11S,13S,14S,16R,17R)-6,9-difluoro-11-hydroxy-10,13,16-trimethyl-3-oxo-17-(propionyloxy)-6,7,8,9,10,11,12,13,14,15,16,17-dodecahydro-3H-cyclopenta[a]phenanthrene-17-carbonyl)thio)decyl)phosphonic acid (3) was as follows.

In a dry round bottom flask equipped with a stir bar under nitrogen, (6S,8S,9R,10S,11S,13S,14S,16R,17R)-6,9-difluoro-11-hydroxy-10,13,16-trimethyl-3-oxo-17-(propionyloxy)-6,7,8,9,10,11,12,13,14,15,16,17-dodecahydro-3H cyclopenta[a]phenanthrene-17-carbothioic S-acid (1, 200 mg, 0.427 mmol) and (10-bromodecyl)phosphonic acid (2, 141 mg, 0.470 mmol, 1.10 eq.) were dissolved in anhydrous DMF (2.1 mL, 0.2M). After 10 minutes of stirring, diisopropylethylamine (176 µL, 1.07 mmol, 2.50 eq.) was added and the reaction stirred overnight at ambient temperature. Upon completion as determined by LCMS, the reaction was concentrated, diluted in DMSO and directly injected on a reverse phase acidic prep HPLC (Sunfire C18 30×150) with 5 to 95 gradient of organic (0.1% TFA/acetonitrile)/aqueous (0.1% TFA/water). The isolated fractions containing product were evaporated using a Genevac and isolated (10-(((6S,8S,9R,10S,11S,13S,14S,16R,17R)-6,9-difluoro-11-hydroxy-10,13,16-trimethyl-3-oxo-17-(propionyloxy)-6,7,8,9,10,11,12,13,14,15,16,17-dodecahydro-3H-cyclopenta[a]phenanthrene-17-carbonyl)thio)decyl)phosphonic acid (3, 185 mg, 63% yield) as a white, foamy solid. LRMS (ES) (M+H)$^+$: observed=689.6, calculated=689.8. $^1$H NMR (DMSO-d$_6$, 500 MHz): $\delta_H$ 7.26 (1H, d, J=10.2 Hz), 6.29 (1H, d, J=10.2 Hz), 6.11 (1H, s), 5.63 (1H, ddd, J=48.7, 11.1, 6.7 Hz), 4.20 (1H, d, J=9.3 Hz), 2.86 (2H, dddd, J=20.9, 18.9, 13.5, 7.4 Hz), 2.31 (2H, q, J=7.7 Hz), 2.24 (1H, br s), 2.05-2.11 (2H, m), 1.80-1.87 (2H, m), 1.47 (8H, d, J=12.3 Hz), 1.31 (5H, br s), 1.25 (9H, s), 0.98-1.02 (6H, m), 0.89 (3H, d, J=7.1 Hz). The following C21 analogs were made by a similar experimental procedure:

| Compound number | Structure | Mass Spectrometry Data |
|---|---|---|
| 4 | 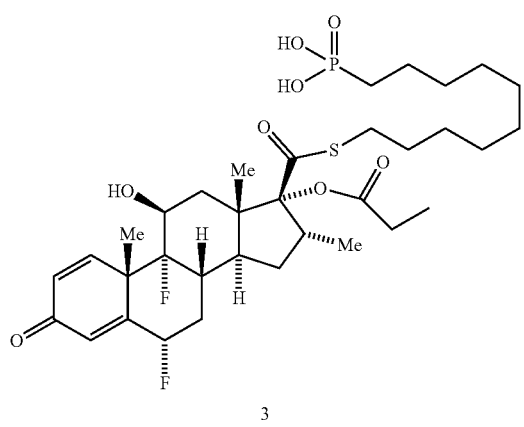 | $C_{28}H_{39}F_2O_8PS$<br>LRMS (ES) (M + H)$^+$:<br>observed 605.2,<br>calculated = 605.2. |

| Compound number | Structure | Mass Spectrometry Data |
|---|---|---|
| 5 | 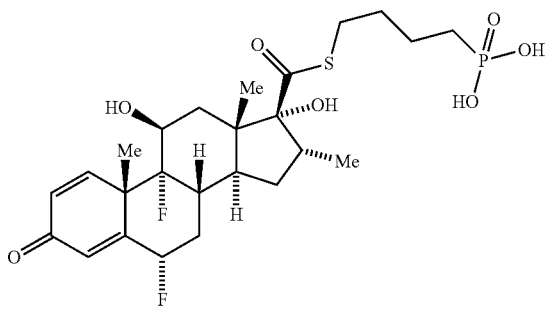 | $C_{25}H_{35}F_2O_7PS$<br>LRMS (ES) (M + H)$^+$:<br>observed 549.2,<br>calculated = 549.2. |
| 6 | 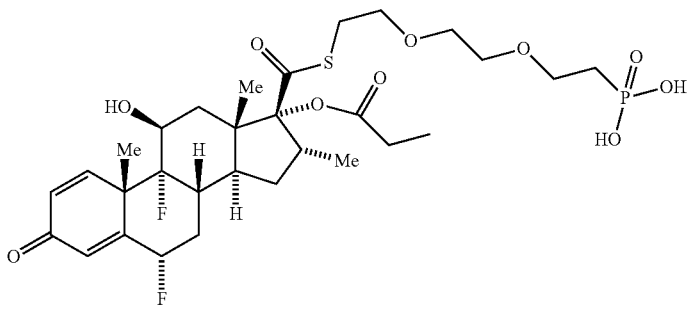 | $C_{30}H_{43}F_2O_{10}PS$<br>LRMS (ES) (M + H)$^+$:<br>observed 665.4,<br>calculated = 665.2. |
| 7 | 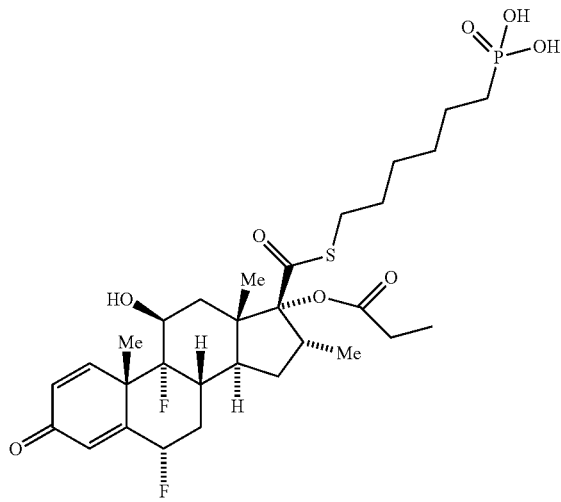 | $C_{30}H_{43}F_2O_8PS$<br>LRMS (ES) (M + H)$^+$:<br>observed 633.4,<br>calculated = 633.2. |
| 8 | 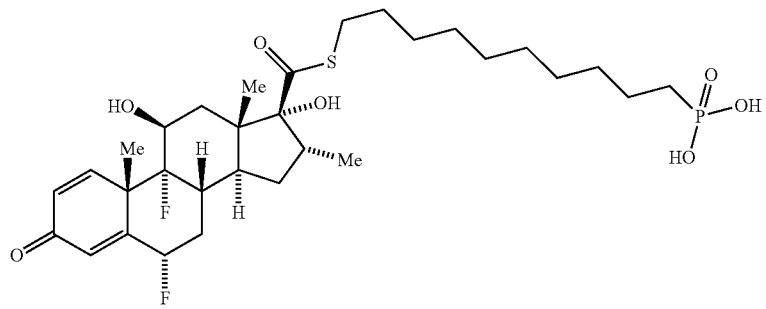 | $C_{31}H_{47}F_2O_7PS$<br>LRMS (ES) (M + H)$^+$:<br>observed 633.4,<br>calculated = 633.3. |

-continued
| Compound number | Structure | Mass Spectrometry Data |
|---|---|---|
| 9 | 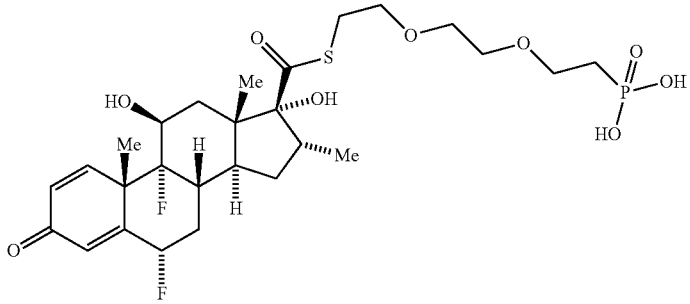 | C$_{27}$H$_{39}$F$_2$O$_9$PS<br>LRMS (ES) (M + H)$^+$:<br>observed 609.3,<br>calculated = 609.2. |
| 10 | 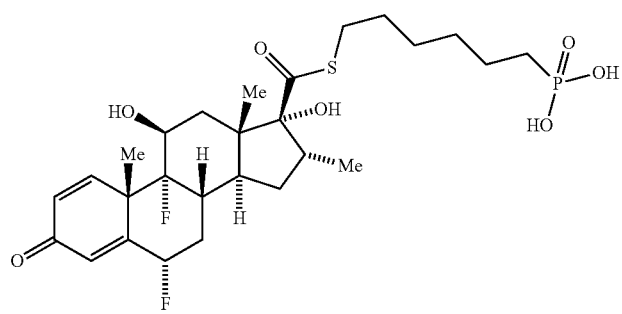 | C$_{27}$H$_{39}$F$_2$O$_7$PS<br>LRMS (ES) (M + H)$^+$:<br>observed 577.5,<br>calculated = 577.2. |
| 11 | 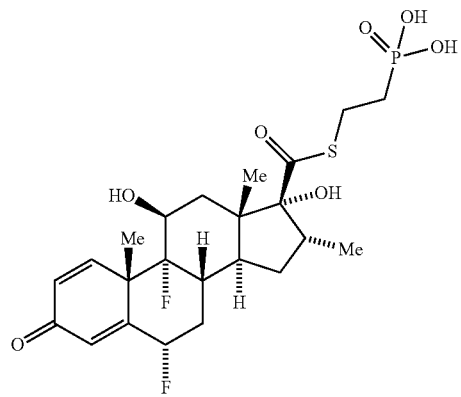 | C$_{23}$H$_{31}$F$_2$O$_7$PS<br>LRMS (ES) (M + H)$^+$:<br>observed 521.3,<br>calculaled = 521.2. |
| 12 | 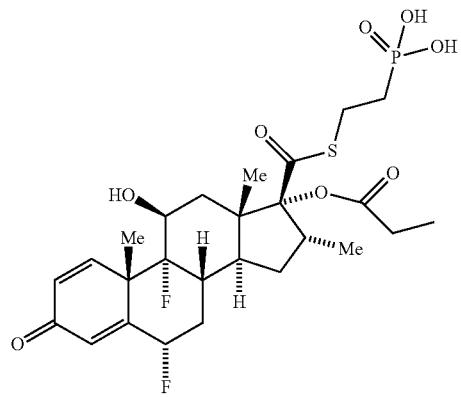 | C$_{26}$H$_{35}$F$_2$O$_8$PS<br>LRMS (ES) (M+H)$^+$:<br>observed 577.2,<br>calculaled = 577.2. |

-continued

| Compound number | Structure | Mass Spectrometry Data |
|---|---|---|
| 13 | 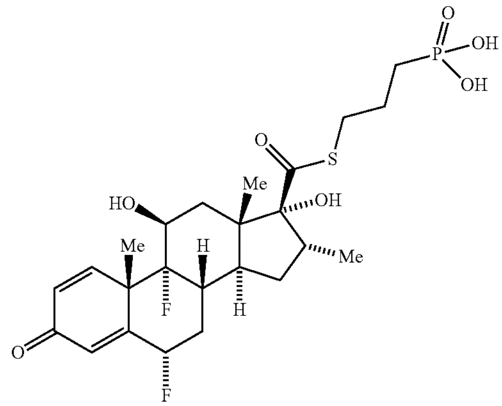 | $C_{24}H_{33}F_2O_7PS$<br>LRMS (ES) $(M + H)^+$:<br>observed 535.2,<br>calculated = 535.2. |
| 14 | 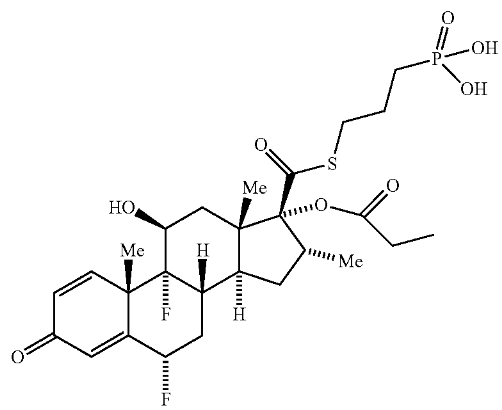 | $C_{27}H_{37}F_2O_8PS$<br>LRMS (ES) $(M + H)^+$:<br>observed 591.2,<br>calculated = 591.2. |

Example 2

This example shows the synthesis of the C17 Analogs.

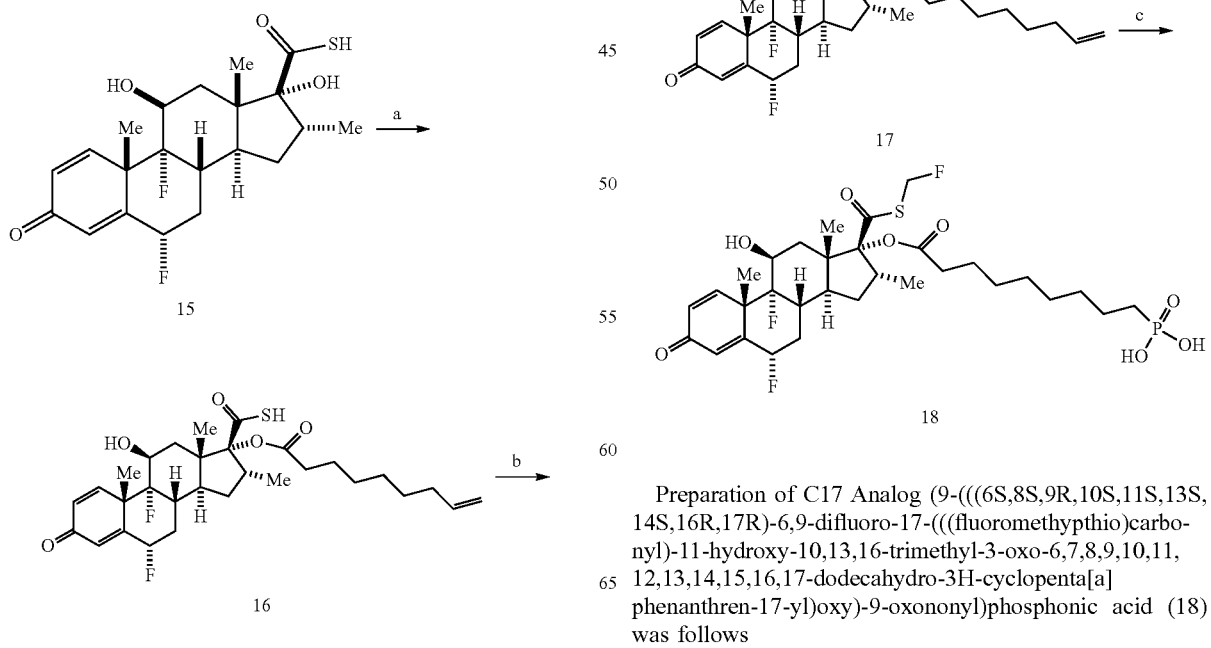

Preparation of C17 Analog (9-((((6S,8S,9R,10S,11S,13S,14S,16R,17R)-6,9-difluoro-17-(((fluoromethylthio)carbonyl)-11-hydroxy-10,13,16-trimethyl-3-oxo-6,7,8,9,10,11,12,13,14,15,16,17-dodecahydro-3H-cyclopenta[a]phenanthren-17-yl)oxy)-9-oxononyl)phosphonic acid (18) was follows Step A: Preparation of (6S,8S,9R,10S,11S,13S,14S, 16R,17R)-6,9-difluoro-11-hydroxy-10,13,16-trimethyl-17-(non-8-enoyloxy)-3-oxo-6,7,8,9,10,11,12, 13,14,15,16,17-dodecahydro-3H-cyclopenta[a] phenanthrene-17-carbothioic S-Acid (16)

In a dry round bottom flask equipped with a stir bar under nitrogen, (6S,8S,9R,10S,11S,13S,14S,16R,17R)-6,9-difluoro-11,17-dihydroxy-10,13,16-trimethyl-3-oxo-6,7,8,9, 10,11,12,13,14,15,16,17-dodecahydro-3H-cyclopenta[a] phenanthrene-17-carbothioic S-acid (15, 100 mg, 0.242 mmol) and triethylamine (84 µL, 0.606 mmol, 2.50 eq.) were dissolved in anhydrous DCM (12.0 mL, 0.02M). To this was added non-8-enoyl chloride (93 mg, 0.533 mmol, 2.20 eq.) and the reaction stirred 20 minutes at ambient temperature. To this was then added N,N-dimethylethylenediamine (64 mg, 0.727 mmol, 3.00 eq.) and stirred at ambient temperature for 1 hour. Upon completion as determined by LCMS, the reaction was washed with 1N HCl twice and concentrated. The crude (6S,8S,9R,10S,11S,13S,14S,16R,17R)-6, 9-difluoro-11-hydroxy-10,13,16-trimethyl-17-(non-8-enoyloxy)-3-oxo-6,7,8,9,10,11,12,13,14,15,16,17-dodecahydro-3H-cyclopenta[a]phenanthrene-17-carbothioic S-acid 16 was carried on directly without further purification. LRMS (ES) (M+H)⁺: observed=551.1, calculated=550.7.

Step B: Preparation of (6S,8S,9R,10S,11S,13S,14S, 16R,17R)-6,9-difluoro-17-(((fluoromethypthio)carbonyl)-11-hydroxy-10,13,16-trimethyl-3-oxo-6,7,8, 9,10,11,12,13,14,15,16,17-dodecahydro-3H-cyclopenta[a]phenanthren-17-yl non-8-enoate (17)

To a round bottom flask containing the crude 16 from step A under nitrogen, was added dioxane (8.0 mL, 0.03M), diisopropylethylamine (118 µL, 0.678 mmol, 2.80 eq.) and bromofluoromethane 2M in DMF (230 µL, 0.460 mmol, 1.90 eq.). The resulting reaction was stirred at ambient temperature for 30 minutes. To this was added additional diisopropylethylamine (480 µL, 2.71 mmol, 11.20 eq.) and bromofluoromethane 2M in DMF (920 µL, 1.84 mmol, 7.6 eq.) and the resulting reaction as stirred at ambient temperature for 3 days. The reaction was concentrated and the residue was dissolved in ethyl acetate and washed several times with 1H HCl solution. The crude material was flash column purified using a 0-50% ethyl aceate/hexane gradient to give (6S,8S,9R,10S,11S,13S,14S,16R,17R)-6,9-difluoro-17-(((fluoromethypthio)carbonyl)-11-hydroxy-10,13,16-trimethyl-3-oxo-6,7,8,9,10,11,12,13,14,15,16,17-dodecahydro-3H-cyclopenta[a]phenanthren-17-yl non-8-enoate (17, 37 mg, 26.5% for 2 steps) LRMS (ES) (M+H)⁺: observed=583.2, calculated=582.7.

Step C: Preparation of (9-(((6S,8S,9R,10S,11S,13S, 14S,16R,17R)-6,9-difluoro-17-(((fluoromethypthio) carbonyl)-11-hydroxy-10,13,16-trimethyl-3-oxo-6,7, 8,9,10,11,12,13,14,15,16,17-dodecahydro-3H-cyclopenta[a]phenanthren-17-yl)oxy)-9-oxononyl) phosphonic acid (18)

To a vial containing 17 (37 mg, 0.063 mmol) under nitrogen, was added 4,4,5,5-tetramethyl-1,3,2-dioxaphospholane 2-oxide (10.42 mg, 0.063 mmol, 1.00 eq.), tris (triphenylphosphine)rhodium(I) chloride (11.75 mg, 0.013 mmol, 0.20 eq.), and 1,4-bis(diphenylphosphino)butane (10.83 mg, 0.025 mmol, 0.40 eq.). Dioxane (0.25 mL, 0.25M) was added and the resulting mixture was heated at 100 C for 23 hours. The mixture was allowed to cool and concentrated to dryness. The residue was dissolved in a mixture of 4N HCl dioxane (100 µL) and water (100 µL) and BHT (4.16 mg, 0.019 mmol, 0.30 eq.) was added. The resulting mixture was heated to 50 C overnight. The reaction was concentrated, dissolved in methanol and directly injected on a reverse phase acidic prep HPLC (Sunfire C18 30×150) with 20 to 80 gradient of organic (0.1% TFA/ acetonitrile)/aqueous (0.1% TFA/water to give (9-(((6S,8S, 9R,10S,11S,13S,14S,16R,17R)-6,9-difluoro-17-(((fluoromethyl)thio)carbonyl)-11-hydroxy-10,13,16-trimethyl-3-oxo-6,7,8,9,10,11,12,13,14,15,16,17-dodecahydro-3H-cyclopenta[a]phenanthren-17-yl)oxy)-9-oxononyl) phosphonic acid (18, 20.3 mg, 48.5% yield). LRMS (ES) (M+H)⁺: observed=665.2, calculated=664.7.

The following C17 Analog was made by a similar experimental procedure:

| Compound number | Structure | Mass Spectrometry Data |
|---|---|---|
| 19 | 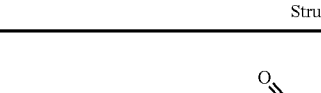 | $C_{28}H_{38}F_3O_8PS$ LRMS (ES) (M + H)⁺: observed 623.2, calculated = 622.6. |

Example 3

This example shows the synthesis of intermediate 25 for constructing A-Ring Analogs.

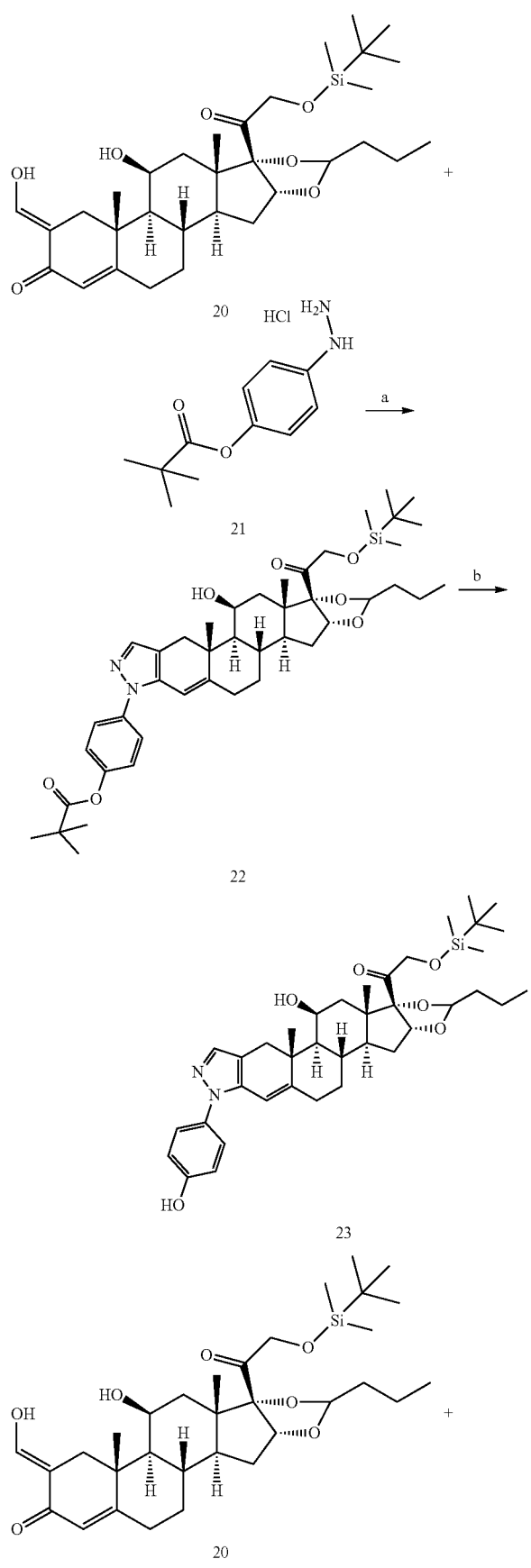
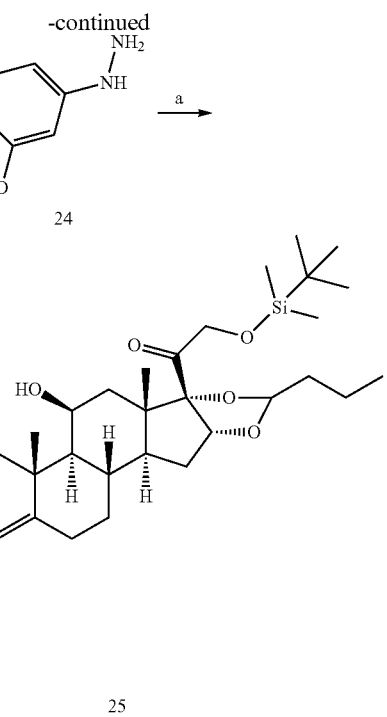

Preparation of intermediate 2-((tert-butyldimethylsilyl)oxy)-1-((3aR,4aS,4bS,11aR,11bS,12S,13aS,13bS)-12-hydroxy-8-(4-hydroxyphenyl)-11a,13a-dimethyl-2-propyl-3a,4,4a,4b,5,6,8,11,11a,11b,12,13,13a,13b-tetradecahydro-[1,3]dioxolo[4",5":3',4']cyclopenta[1',2':5,6]naphtho[1,2-f]indazol-13b-yl)ethanone (23) was as follows.

Step A: Preparation of 4-((3aR,4aS,4bS,11aR,11bS,12S,13aS,13bS)-13b-(2-((tert-butyldimethylsilyl)oxy)acetyl)-12-hydroxy-11a,13a-dimethyl-2-propyl-4,4a,5,6,11,11a,11b,12,13,13a-decahydro-[1,3]dioxolo[4",5":3',4']cyclopenta[1',2':5,6]naphtho[1,2-f]indazol-8(3aH,4bH,13bH)-yl)phenyl pivalate (22)

In a dry 20 mL microwave vial equipped with a stir bar under nitrogen, (20, 500 mg, 0.870 mmol, synthesis described in WO 2009082342) and 4-hydrazinylphenyl pivalate HCl (21, 234 mg, 0.957 mmol, 1.10 eq.) were dissolved in ethanol (5.1 mL, 0.17M). To this was added potassium acetate (128 mg, 1.305 mmol, 1.50 eq.) and the vial was microwave irradiated to 90 C for 15 minutes. The crude reaction was concentrated and flash column purified using a 0-30% ethyl acetate/hexane gradient to gave 4-((3aR,4aS,4bS,11aR,11bS,12S,13aS,13bS)-13b-(2-((tert-butyldimethylsilypoxy)acetyl)-12-hydroxy-11a,13a-dimethyl-2-propyl-4,4a,5,6,11,11a,11b,12,13,13a-decahydro-[1,3]dioxolo[4",5":3',4']cyclopenta[1',2':5,6]naphtho[1,2-f]indazol-8(3aH,4bH,13bH)-yl)phenyl pivalate. (22, 497 mg, 76% yield). LRMS (ES) (M+H)$^+$: observed=747.6, calculated=747.0.

Step B: Preparation of 2-((tert-butyldimethylsilyl)oxy)-1-((3aR,4aS,4bS,11aR,11bS,12S,13aS,13bS)-12-hydroxy-8-(4-hydroxyphenyl)-11a,13a-dimethyl-2-propyl-3a,4,4a,4b,5,6,8,11,11a,11b,12,13,13a,13b-tetradecahydro-[1,3]oxolo[4",5":3',4']cyclopenta[1',2':5,6]naphtho[1,2-f]indazol-13b-yl)ethanone (Intermediate 23)

In a round bottom flask equipped with a stir bar 4-((3aR,4aS,4bS,11aR,11bS,12S,13aS,13bS)-13b-(2-((tert-butyldimethylsilypoxy)acetyl)-12-hydroxy-11a,13a-dimethyl-2-propyl-4,4a,5,6,11,11a,11b,12,13,13a-decahydro-[1,3]dioxolo[4",5":3',4']cyclopenta[1',2':5,6]naphtho[1,2-f]indazol-8(3aH,4bH,13bH)-yl)phenyl pivalate. (22, 850 mg, 1.138 mmol) was dissolved in THF (7.1 mL, 0.16M). To this was added 1M aq lithium hydroxide (2276 µL, 2.276 mmol, 2.00 eq.) and stirred at ambient temperature overnight. The reaction was poured into saturated aq ammonium chloride solution and extracted several times with ethyl acetate. The combined organic layers were concentrated and flash column purified using a 0-50% ethyl aceate/hexane gradient to gave 2-((tert-butyldimethylsilypoxy)-1-((3aR,4aS,4bS,11aR,11bS,12S,13aS,13bS)-12-hydroxy-8-(4-hydroxyphenyl)-11a,13a-dimethyl-2-propyl-3a,4,4a,4b,5,6,8,11,11a,11b,12,13,13a,13b-tetradecahydro-[1,3]dioxolo[4",5": 3',4'] cyclopenta[1',2':5,6]naphtho[1,2-f]indazol-13b-yl) ethanone. (23, 560 mg, 74.2% yield). LRMS (ES) (M+H)+: observed=663.5, calculated=662.9.

Preparation of 2-((tert-butyldimethylsilypoxy)-1-((3aR,4aS,4bS,11aR,11bS,12S,13aS,13bS)-12-hydroxy-8-(3-hydroxyphenyl)-11a,13a-dimethyl-2-propyl-3a,4,4a,4b,5,6,8,11,11a,11b,12,13,13a,13b-tetradecahydro-[1,3]dioxolo[4",5":3',4']cyclopenta[1',2':5,6]naphtho[1,2-f]indazol-13b-yl) ethanone (25) was as follows.

In a dry 20 mL microwave vial equipped with a stir bar under nitrogen, (20, 450 mg, 0.783 mmol, synthesis described in WO 2009082342) and 3-hydrazinylphenol, HCl (24, 143 mg, 0.892 mmol, 1.14 eq.) were dissolved in ethanol (4.6 mL, 0.17M). To this was added potassium acetate (115 mg, 1.174 mmol, 1.50 eq.) and the vial was microwave irradiated to 90 C for 15 minutes. The crude reaction was concentrated and flash column purified using a 0-50% ethyl aceate/hexane gradient to gave 2-((tert-butyldimethylsilyl)oxy)-1-((3aR,4aS,4bS,11aR,11bS,12S,13aS,13bS)-12-hydroxy-8-(3-hydroxyphenyl)-11a,13a-dimethyl-2-propyl-3a,4,4a,4b,5,6,8,11,11a,11b,12,13,13a,13b-tetradecahydro-[1,3]dioxolo[4",5":3',4']cyclopenta[1',2':5,6]naphtho[1,2-f]indazol-13b-yl)ethanone. (25, 380 mg, 73.2% yield). LRMS (ES) (M+H)+: observed=663.4, calculated=662.9.

Example 4

This example shows the synthesis of A-Ring Analogs.

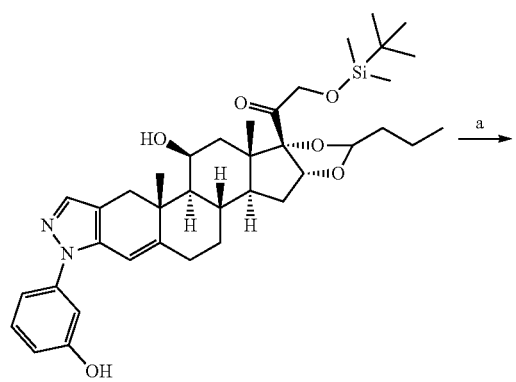

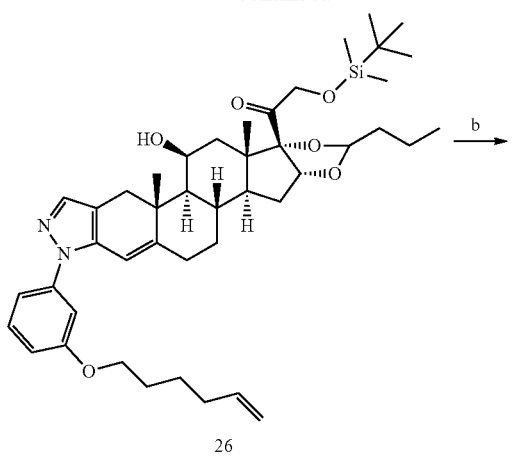

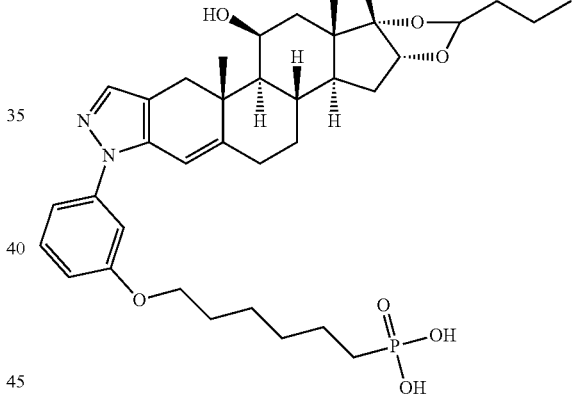

Preparation of A-Ring Analog (6-(3-((3aR,4aS,4bS,11aR,11bS,12S,13aS,13bS)-12-hydroxy-13b-(2-hydroxyacetyl)-11a,13a-dimethyl-2-propyl-4,4a,5,6,11,11a,11b,12,13,13a-decahydro-[1,3]dioxolo[4",5": 3',4']cyclopenta[1',2': 5,6]naphtho[1,2-f]indazol-8(3aH,4bH,13bH)-yl)phenoxy)hexyl)phosphonic acid (27) was follows.

Step A: Preparation of 2-((tert-butyldimethylsilyl)oxy)-1-((3aR,4aS,4bS,11aR,11bS,12S,13aS,13bS)-8-(3-(hex-5-en-1-yloxy)phenyl)-12-hydroxy-11a,13a-dimethyl-2-propyl-3a,4,4a,4b,5,6,8,11,11a,11b,12,13,13a,13b-tetradecahydro-[1,3]dioxolo[4",5":3',4']cyclopenta[1',2':5,6]naphtho[1,2-f]indazol-13b-yl)ethanone (26)

In a vial equipped with a stir bar under nitrogen, 2-((tert-butyldimethylsilypoxy)-1-((3aR,4aS,4bS,11aR,11bS,12S, 13aS,13bS)-12-hydroxy-8-(3-hydroxyphenyl)-11a,13a-dimethyl-2-propyl-3a,4,4a,4b,5,6,8,11,11a,11b, 12,13,13a, 13b-tetradecahydro-[1,3]dioxolo[4″,5″:3′,4′]cyclopenta[1′, 2′: 5,6]naphtho[1,2-f]indazol-13b-yl)ethanone (25, 140 mg, 0.211 mmol) and 5-hexen-1-ol (21.15 mg, 0.211 mmol, 1.00 eq.) and triphenylphosphine (55.40 mg, 0.211 mmol, 1.00 eq.) were dissolved in dioxane (1.0 mL, 0.21M). To this was added Di-tert-butyl azodicarboxylate (58.4 mg, 0.253 mmol, 1.20 eq.) and the resulting mixture was stirred at ambient temperature until complete based upon LCMS. The crude reaction was concentrated and flash column purified using a 0-50% ethyl aceate/hexane gradient to gave 2-((tert-butyldimethylsilypoxy)-1-((3aR,4aS,4bS,11aR,11bS,12S,13aS, 13bS)-8-(3-(hex-5-en-1-yloxy)phenyl)-12-hydroxy-11a, 13a-dimethyl-2-propyl-3a,4,4a,4b,5,6,8,11,11a, 11b,12,13, 13a, 13b-tetradecahydro-[1,3]dioxolo[4″,5″:3′,4′]cyclopenta [1′,2′:5,6]naphtho[1,2-f]indazol-13b-yl)ethanone. (26, 119 mg, 76% yield). LRMS (ES) (M+H)⁺: observed=745.5, calculated=745.0.

Step B: Preparation of (6-(3-((3aR,4aS,4bS,11aR, 11bS,12S,13a5,13bS)-12-hydroxy-13b-(2-hydroxyacetyl)-11a,13a-dimethyl-2-propyl-4,4a,5,6,11,11a, 11b,12,13,13a-decahydro-[1,3]dioxolo[4″,5″:3′,4′] cyclopenta[1′,2′:5,6]naphtho[1,2-f]indazol-8(3aH, 4bH,13bH)-yl)phenoxy)hexyl)phosphonic acid (27)

In a similar manner to Step C of Example 2, 2-((tert-butyldimethylsilyl)oxy)-1-((3aR,4aS,4bS,11aR,11bS,12S, 13aS,13bS)-8-(3-(hex-5-en-1-yloxy)phenyl)-12-hydroxy-11a,13a-dimethyl-2-propyl-3a,4,4a,4b,5,6,8,11,11a,11b, 12,13,13a,13b-tetradecahydro-[1,3]dioxolo[4″,5″:3′4′]cyclopenta[1′,2′:5,6]naphtho[1,2-f]indazol-13b-yl)ethanone (26) and tetramethyl-1,3,2-dioxaphospholane 2-oxide were used to synthesize (6-(3-((3aR,4aS,4bS,11aR,11bS,12S, 13aS,13bS)-12-hydroxy-13b-(2-hydroxyacetyl)-11a,13a-dimethyl-2-propyl-4,4a,5,6,11,11a,11b,12,13,13a-decahydro-[1,3]dioxolo[4″,5″:3′,4′]cyclopenta[1′,2′:5,6]naphtho[1,2-f] indazol-8 (3aH,4bH,13bH)-yl)phenoxy)hexyl)phosphonic acid. (27). LRMS (ES) (M+H)⁺: observed=713.3, calculated=712.8.

The following A-Ring Analogs were made by a similar procedure:

| Compound number | Structure | Mass Spectrometry Data |
|---|---|---|
| 28 | 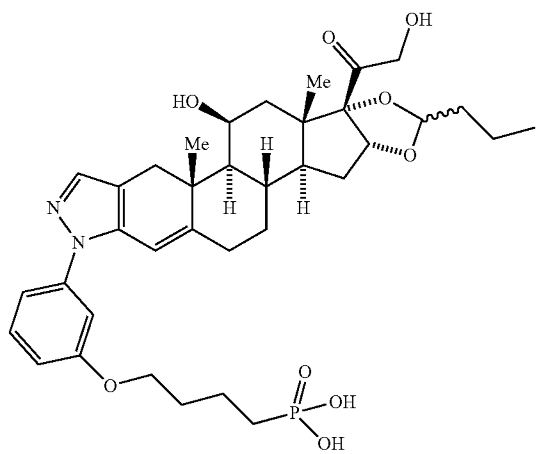 | $C_{36}H_{49}N_2O_9P$ LRMS (ES) (M + H)⁺: observed 685.4, calculated = 684.7. |
| 29 | 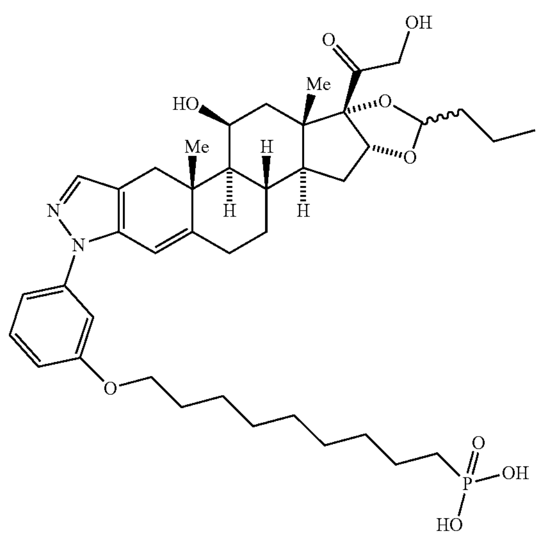 | $C_{41}H_{59}N_2O_9P$ LRMS (ES) (M + H)⁺: observed 755.4, calculated = 754.8. |

-continued

| Compound number | Structure | Mass Spectrometry Data |
|---|---|---|
| 30 | 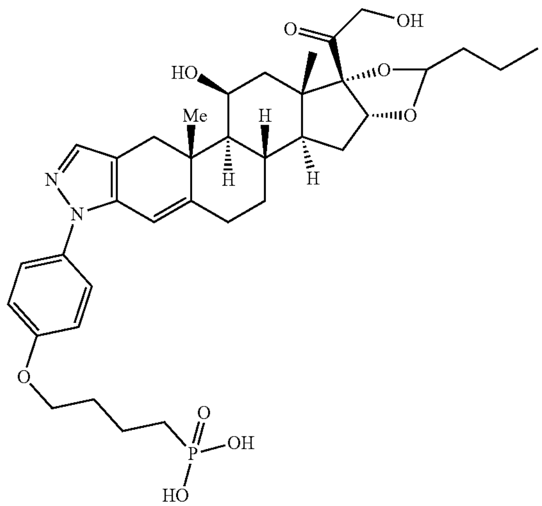 | $C_{36}H_{49}N_2O_9P$<br>LRMS (ES) (M + H)$^+$:<br>observed 685.3,<br>calculated = 684.7. |
| 31 | 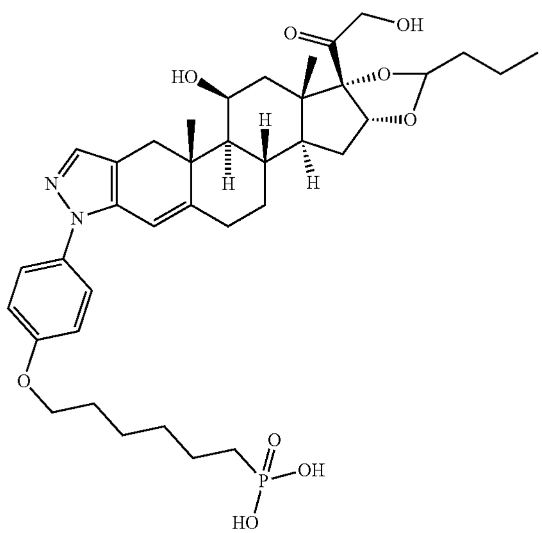 | $C_{38}H_{53}N_2O_9P$<br>LRMS (ES) (M + H)$^+$:<br>observed 713.4,<br>calculated = 712.8. |
| 32 | 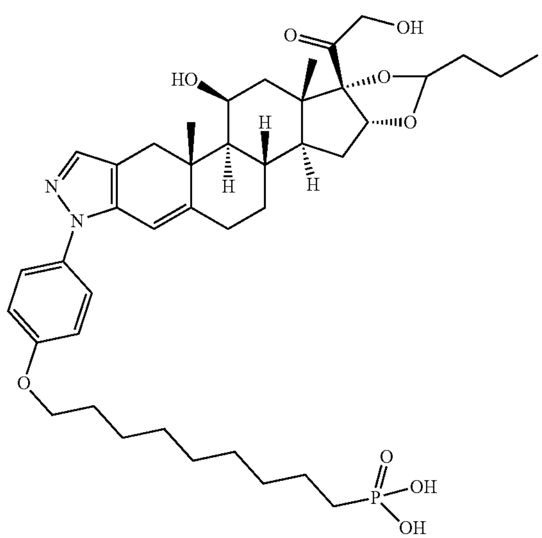 | $C_{41}H_{59}N_2O_9P$<br>LRMS (ES) (M + H)$^+$:<br>observed 755.4,<br>calculated = 754.8. |

Example 5

This example shows the synthesis of pyrophosphonate drug linkers.

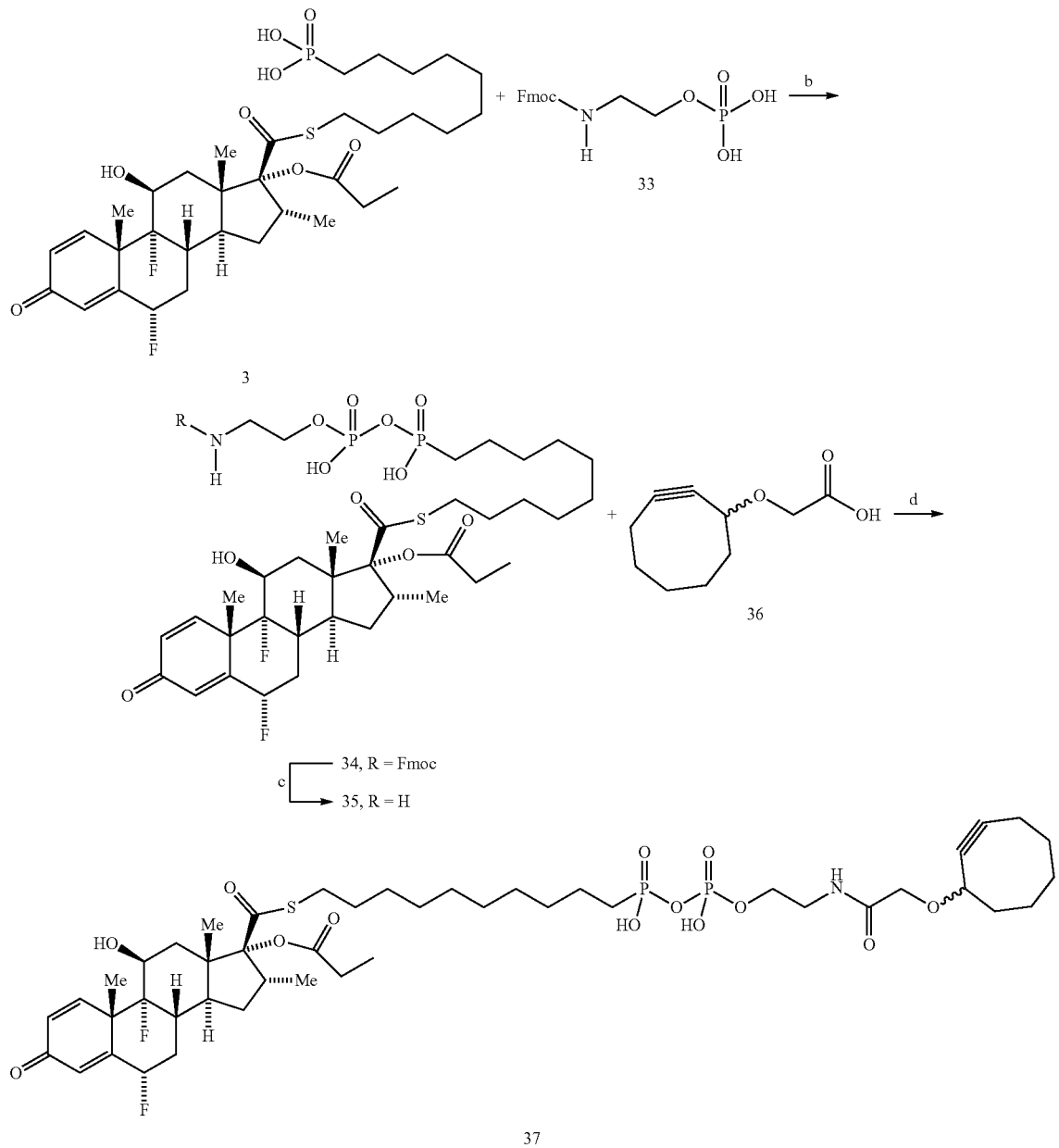

Step B: Preparation of ((9H-fluoren-9-yl)methylcarbamoyl)-2-aminoethyl phosphoric) (10-((((6S,8S, 9R,10S,11S,13S,14S,16R,17R)-6,9-difluoro-11-hydroxy-10,13,16-trimethyl-3-oxo-17-(propionyloxy)-6,7,8,9,10,11,12,13,14,15,16,17-dodecahydro-3H-cyclopenta[a]phenanthrene-17-carbonyl)thio) decyl) phosphonic anhydride (34)

In a dry glass vial equipped with a stir bar under nitrogen, (9H-fluoren-9-yl)methyl (2-(phosphonooxy)ethyl)carbamate (33, 95 mg, 0.261 mmol, 1 eq.) and carbonyldiimidazole (50.8 mg, 0.314 mmol, 1.2 eq.) were dissolved in anhydrous DMF (0.50 mL) and treated with triethylamine (36.4 µL, 0.261 mmol, 1 eq.). The reaction was stirred 20 min and found to be complete as measured by LCMS. In a separate dry glass vial (10-((((6S,8S,9R,10S,11S,13S,14S,16R,17R)-6,9-difluoro-11-hydroxy-10,13,16-trimethyl-3-oxo-17-(propionyloxy)-6,7,8,9,10,11,12,13,14,15,16,17-dodecahydro-3H-cyclopenta[a]phenanthrene-17-carbonyl)thio)decyl) phosphonic acid (3, 180 mg, 0.261 mmol, 1 eq.) and zinc (II) chloride (214 mg, 1.57 mmol, 6 eq.) were combined and dissolved in anhydrous DMF (0.80 mL, 0.2M final concentration of reaction). To this latter solution was added the solution of activated 33 and the resulting mixture was stirred overnight at ambient temperature. The reaction was judged to be complete by LCMS (basic conditions) after 12 h and diluted with 1N HCl (5 mL). The mixture was extracted with DCM (5×5 mL) and the combined extracts were concentrated. The resulting crude was dissolved in 1 mL of methanol and injected onto a on a reverse phase basic prep HPLC (Phenomenex Gemini-NX C18 OBD 5 uM 30×100 mm; 30-90% MeCN/water w/0.1% NH₄OH modifier over 20 min). The isolated fractions containing product were evaporated using a lyophilizer and isolated ((9H-fluoren-9-yl) methyl-carbamoyl)-2-aminoethyl phosphoric) (10-(((6S,8S, 9R,10S,11S,13S,14S,16R,17R)-6,9-difluoro-11-hydroxy-10,13,16-trimethyl-3-oxo-17-(propionyloxy)-6,7,8,9,10,11, 12,13,14,15,16,17-dodecahydro-3H-cyclopenta[a] phenanthrene-17-carbonyl)thio)decyl) phosphonic anhydride (34, 88.0 mg, 32% yield) as a white solid. LRMS (ES) (M+H)⁺: observed=1034.6, calculated=1034.0.

Step C: Preparation of (2-aminoethyl phosphoric) (10-(((6S,8S,9R,10S,11S,13S,14S,16R,17R)-6,9-difluoro-11-hydroxy-10,13,16-trimethyl-3-oxo-17-(propionyloxy)-6,7,8,9,10,11,12,13,14,15,16,17-dodecahydro-3H-cyclopenta[a]phenanthrene-17-carbonyl)thio) decyl) phosphonic anhydride (35)

In a dry round bottom flask equipped with a stir bar under nitrogen, ((9H-fluoren-9-yl)methyl-carbamoyl)-2-aminoethyl phosphoric) (10-(((6S,8S,9R,10S,11S,13S,14S,16R, 17R)-6,9-difluoro-11-hydroxy-10,13,16-trimethyl-3-oxo-17-(propionyloxy)-6,7,8,9,10,11,12,13,14,15,16,17-dodecahydro-3H-cyclopenta[a]phenanthrene-17-carbonyl) thio)decyl) phosphonic anhydride (34, 88.0 mg, 0.085 mmol) was dissolved in anhydrous dichloromethane (0.42 mL, 0.2M) and treated with DBU (65 mL, 0.425 mmol, 5 eq). The resulting solution was stirred at ambient temperature for 1 h and determined to be complete as judged by LCMS. The reaction was concentrated and taken up in methanol and injected onto a on a reverse phase basic prep HPLC (Phenomenex Gemini-NX C18 OBD 5 uM 30×100 mm; 10-70% MeCN/water w/0.1% NH₄OH modifier over 20 min, 235 nM wavelength). The isolated fractions containing product were evaporated using a lyophilizer and isolated (2-aminoethyl phosphoric) (10-(((6S,8S,9R,10S, 11S,13S,14S,16R,17R)-6,9-difluoro-11-hydroxy-10,13,16-trimethyl-3-oxo-17-(propionyloxy)-6,7,8,9,10,11,12,13,14, 15,16,17-dodecahydro-3H-cyclopenta[a]phenanthrene-17-carbonyl)thio) decyl)phosphonic anhydride (35, 27.0 mg, 39% yield) as a white solid. LRMS (ES) (M+H)⁺: observed=812.4, calculated=812.8.

Step D: Preparation (2-(2-(cyclooct-2-yn-1-yloxy) acetamido)ethyl phosphoric) (10-(((6S,8S,9R,10S, 11S,13S,14S,16R,17R)-6,9-difluoro-11-hydroxy-10, 13,16-trimethyl-3-oxo-17-(propionyloxy)-6,7,8,9,10, 11,12,13,14,15,16,17-dodecahydro-3H-cyclopenta[a] phenanthrene-17-carbonyl)thio)decyl)phosphonic anhydride (37)

In a dry round bottom flask equipped with a stir bar under nitrogen, (2-aminoethyl phosphoric) (10-(((6S,8S,9R,10S, 11S,13S,14S,16R,17R)-6,9-difluoro-11-hydroxy-10,13,16-trimethyl-3-oxo-17-(propionyloxy)-6,7,8,9,10,11,12,13,14, 15,16,17-dodeca-hydro-3H-cyclopenta[a]phenanthrene-17-carbonyl)thio)decyl)phosphonic anhydride (35, 9.0 mg, 11 mmol, 1.0 eq) and 2-(cyclooct-2-yn-1-yloxy)acetic acid (36, 3.0 mg, 17 mmol, 1.5 eq) were dissolved in anhydrous DMF (0.37 mL, 0.03M). To the resulting solution was added HATU (6.3 mg, 17 mmol, 1.5 eq) and triethylamine (6.2 μL, 44 mmol, 4 eq.). The reaction became yellow immediately and stirred 20 min before completion as judged by basic LCMS. The reaction was injected onto a on a reverse phase basic prep HPLC (Phenomenex Gemini-NX C18 OBD 5 uM 30×100 mm; 10-70% MeCN/water w/0.1% NH₄OH modifier over 20 min, 235 nM wavelength). The isolated fractions containing product were evaporated using a lyophilizer and isolated (2-(2-(cyclooct-2-yn-1-yloxy)acetamido)ethyl phosphoric) (10-(((6S,8S,9R,10S,11S,13S,14S,16R,17R)-6, 9-difluoro-11-hydroxy-10,13,16-trimethyl-3-oxo-17-(propionyloxy)-6,7,8,9,10,11,12,13,14,15,16,17-dodecahydro-3H-cyclopenta[a]phenanthrene-17-carbonyl)thio)decyl) phos-phonic anhydride (37, 6.0 mg, 55% yield) as a white solid. LRMS (ES) (M+H)⁺: observed=976.6, calculated=977.0. ¹H NMR (DMSO-d₆, 500 MHz): δ_H 8.33 (1H, s), 7.35 (1H, d, J=10.1 Hz), 6.27 (1H, dd, J=10.0, 2.0 Hz), 6.10 (1H, d, J=2.1 Hz), 5.63 (1H, ddd, J=48.7, 10.7, 6.4 Hz), 4.29 (1H, t, J=5.2 Hz), 4.20 (1H, d, J=9.0 Hz), 3.89 (1H, d, J=14.6 Hz), 3.73-3.76 (3H, m), 3.22-3.27 (3H, m), 2.86 (2H, dddd, J=19.8, 13.9, 12.7, 7.0 Hz), 2.31 (2H, ddd, J=8.4, 8.2, 6.5 Hz), 2.21-2.25 (3H, m), 2.15 (1H, t, J=6.8 Hz), 2.05-2.11 (4H, m), 1.70-1.93 (7H, m), 1.45-1.58 (10H, m), 1.24-1.31 (15H, m), 0.98-1.01 (6H, m), 0.86-0.90 (4H, m).

Example 6

This example shows the synthesis of pyrophosphonate drug linkers.

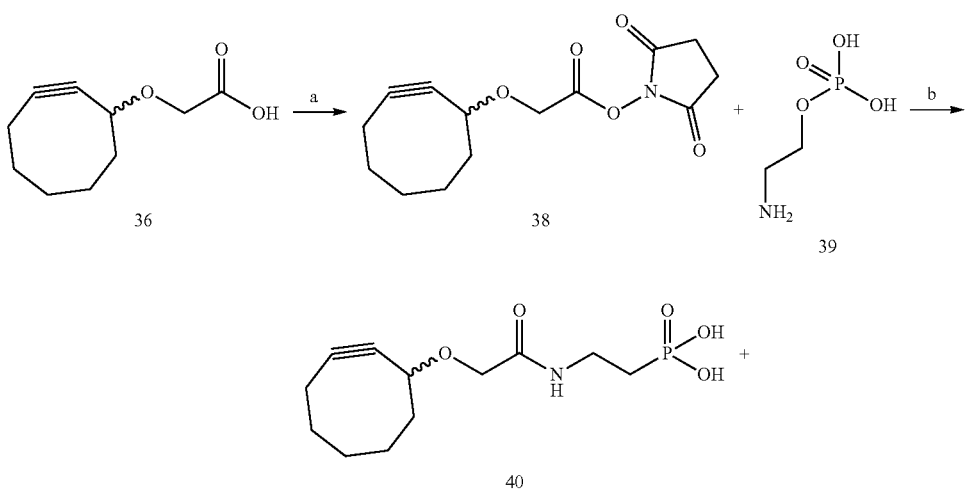

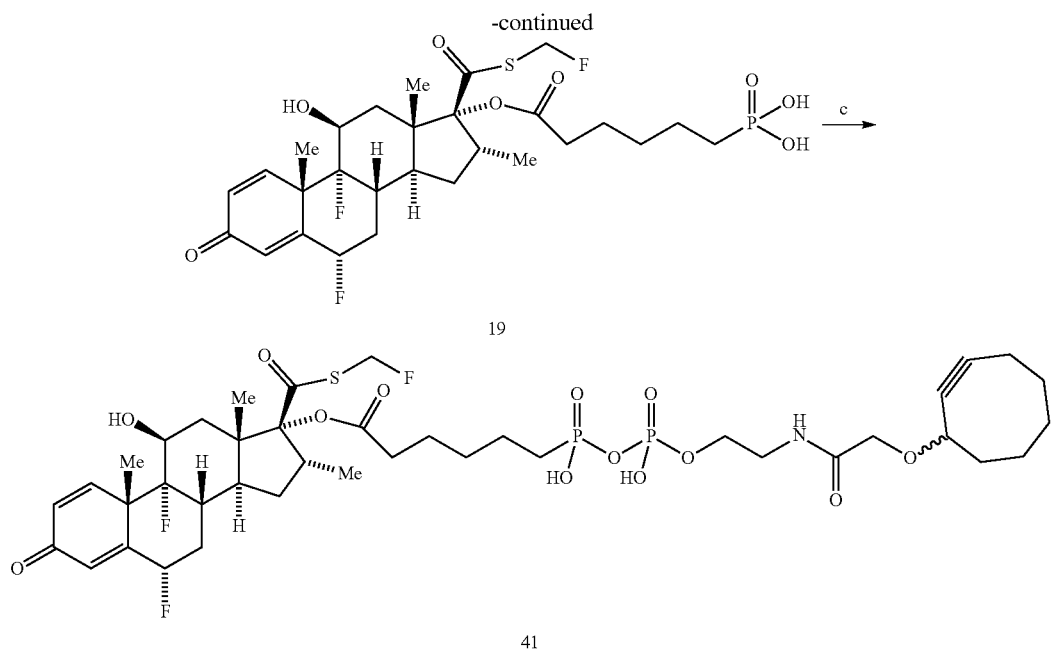

Step A: 1,3-dioxoisoindolin-2-yl 2-(cyclooct-2-yn-1-yloxy)acetate(38)

To a stirred solution of 2-(cyclooct-2-yn-1-yloxy)acetic acid (36, 0.10 g, 0.55 mmol) in DCM (2 mL) was added 2-hydroxyisoindoline-1,3-dione (0.18 g, 1.10 mmol) and EDC (0.21 g 1.10 mmol) and the resulting mixture was stirred at room temperature for 1.5 hrs. The solution was directly purified by flash column separation using a 0-50% ethyl acetate/hexane gradient gave the title compound (38, 163 mg, 91%).

Step B: (2-(2-(cyclooct-2-yn-1-yloxy)acetamido)ethyl)phosphonic acid (40)

To a stirred mixture of 1,3-dioxoisoindolin-2-yl 2-(cyclooct-2-yn-1-yloxy)acetate (38, 79.0 mg, 0.29 mmol) and 2-aminoethyl dihydrogen phosphate (39, 59.9 mg, 0.42 mmol, 1.5 eq) in 1:1 DMF/H$_2$O (1.0 mL) was added triethylamine (59.1 uL, 0.42 mmol, 1.5 eq) and the mixture became a solution. The resulting solution stirred 2 h before being injected directly onto reverse phase acidic prep HPLC (Sunfire C18 30×150) with 5 to 95 gradient of organic (0.1% TFA/acetonitrile)/aqueous (0.1% TFA/water). The isolated fractions containing product were evaporated using a Genevac and isolated (2-(2-(cyclooct-2-yn-1-yloxy)acetamido)ethyl)phosphonic acid (40, 45.0 mg, 54% yield) as a white solid. LRMS (ES) (M+H)$^+$: observed=306.3, calculated=306.3.

Step C: (2-(2-(cyclooct-2-yn-1-yloxy)acetamido)ethyl phosphoric) (6-(((6S,8S,9R,10S,11S,13S,14S,16R,17R)-6,9-difluoro-17-(((fluoromethyl)thio)carbonyl)-11-hydroxy-10,13,16-trimethyl-3-oxo-6,7,8,9,10,11,12,13,14,15,16,17-dodecahydro-3H-cyclopenta[a]phenanthren-17-yl)oxy)-6-oxohexyl) phosphonic anhydride (41)

In a dry glass vial equipped with a stir bar under nitrogen, (2-(2-(cyclooct-2-yn-1-yloxy)acetamido)ethyl)phosphonic acid (40, 14.7 mg, 0.048 mmol, 1 eq.) and carbonyldiimidazole (9.4 mg, 0.058 mmol, 1.2 eq.) were dissolved in anhydrous DMF (0.19 mL) and treated with triethylamine (6.7 µL, 0.048 mmol, 1 eq.). The reaction was stirred 15 min and found to be complete as measured by LCMS. In a separate dry glass vial (6-(((6S,8S,9R,10S,11S,13S,14S,16R,17R)-6,9-difluoro-17-(((fluoromethyl)thio) carbonyl)-11-hydroxy-10,13,16-trimethyl-3-oxo-6,7,8,9,10,11,12,13,14,15,16,17-dodecahydro-3H-cyclopenta[a]phenanthren-17-yl)oxy)-6-oxohexyl)phosphonic acid (19, 30 mg, 0.048 mmol, 1 eq.) and zinc (II) chloride (39.4 mg, 0.289 mmol, 6 eq.) were combined and dissolved in anhydrous DMF (0.05 mL, 0.2M final concentration of reaction). To this latter solution was added the solution of activated 40 and the resulting mixture was stirred 2 days at ambient temperature. The reaction was judged to be complete by LCMS (basic conditions) and diluted with 1N HCl. The mixture was extracted with DCM several times and the combined extracts were concentrated. The resulting crude was dissolved in DMF and injected onto a reverse phase basic prep HPLC (Phenomenex Gemini-NX C18 OBD 5 uM 30×100 mm; 10-60% MeCN/water w/0.1% NH$_4$OH modifier over 20 min to give (2-(2-(cyclooct-2-yn-1-yloxy)acetamido) ethyl phosphoric) (6-(((6S,8S,9R,10S,11S,13S,14S,16R,17R)-6,9-difluoro-17-(((fluoromethyl)thio)carbonyl)-11-hydroxy-10,13,16-trimethyl-3-oxo-6,7,8,9,10,11,12,13,14,15,16,17-dodecahydro-3H-cyclopenta[a]phenanthren-17-yl)oxy)-6-oxohexyl)phosphonic anhydride (41, 13.0 mg, 30% yield) as a white solid. LRMS (ES) (M+H)$^+$: observed=910.4, calculated=909.8.

The following compounds were made by a similar procedure:

| Compound number | Structure | Mass Spectrometry Data |
|---|---|---|
| 42 | 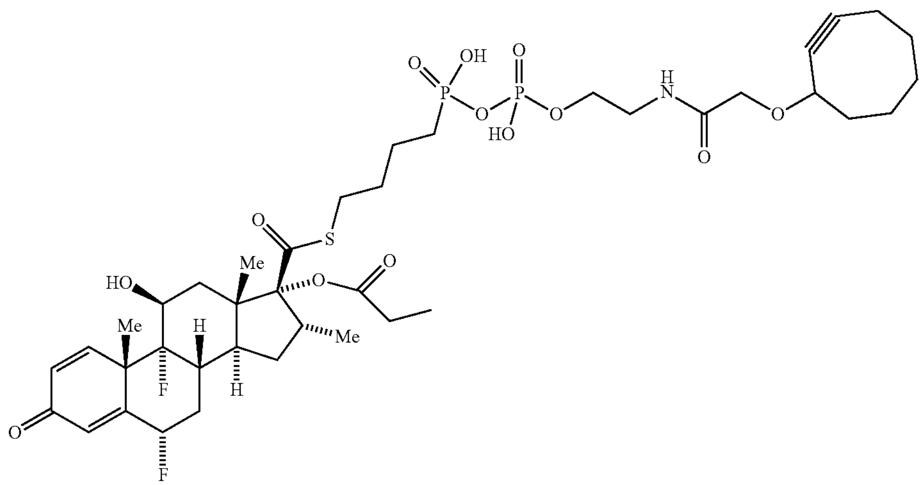 | $C_{40}H_{57}F_2NO_{13}P_2S$ LRMS (ES) $(M + H)^+$: observed 892.4, calculated = 891.8. |
| 43 | 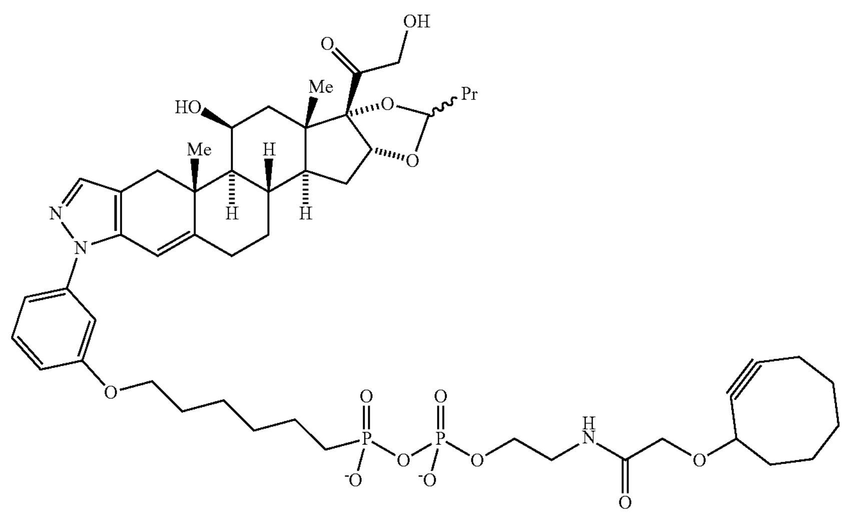 | $C_{50}H_{71}N_3O_{14}P_2$ LRMS (ES) $(M + H)^+$: observed 1000.6, calculated = 1000.0. |
| 44 | 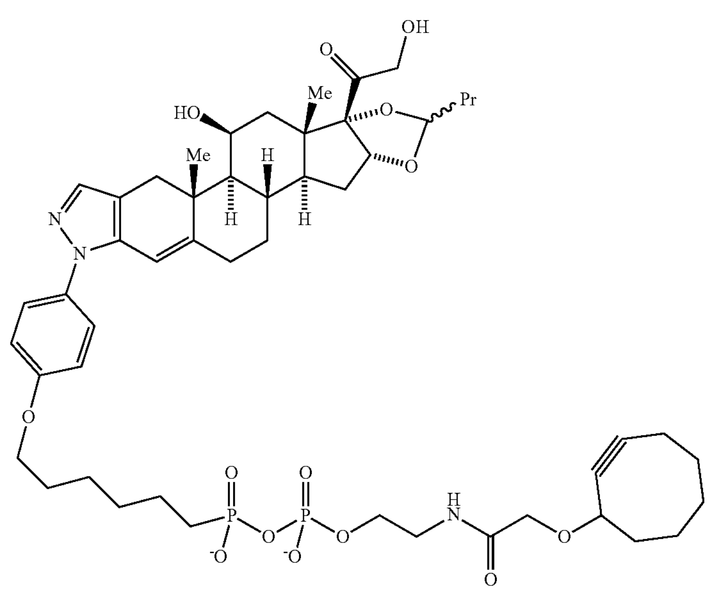 | $C_{50}H_{71}N_3O_{14}P_2$ LRMS (ES) $(M + H)^+$: observed 1000.6, calculated = 1000.0. |

Example 7
This example shows the synthesis of cathepsin phosphonate drug linkers
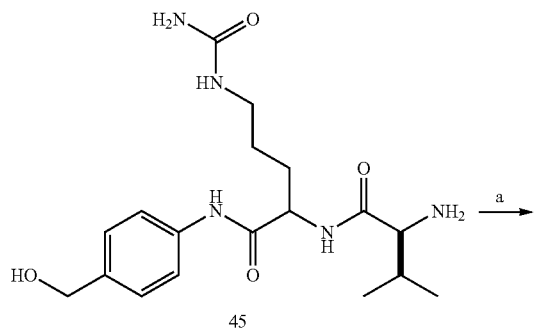
45
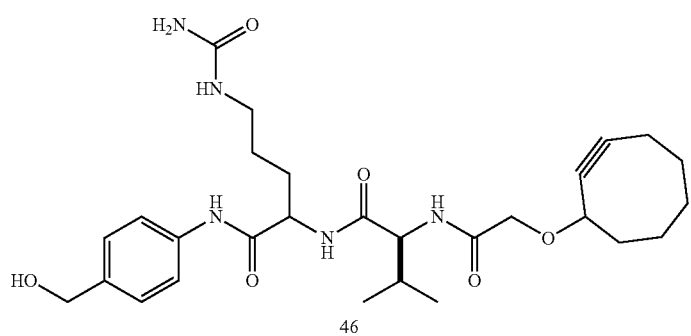
46
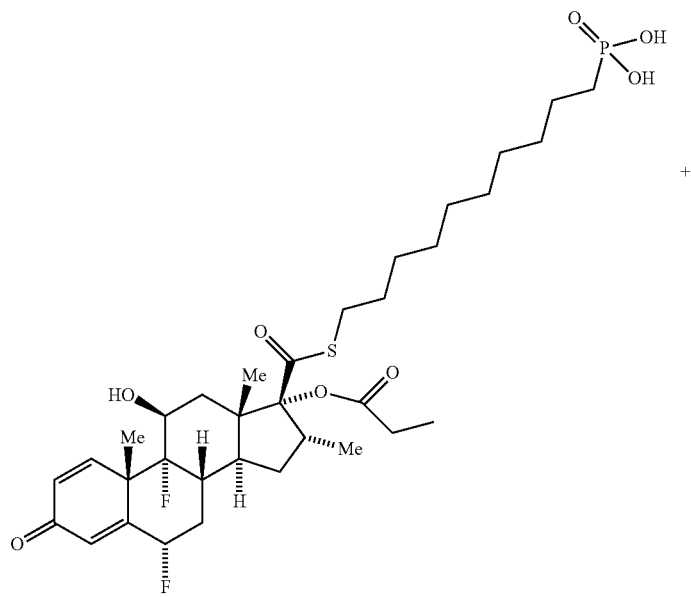
3

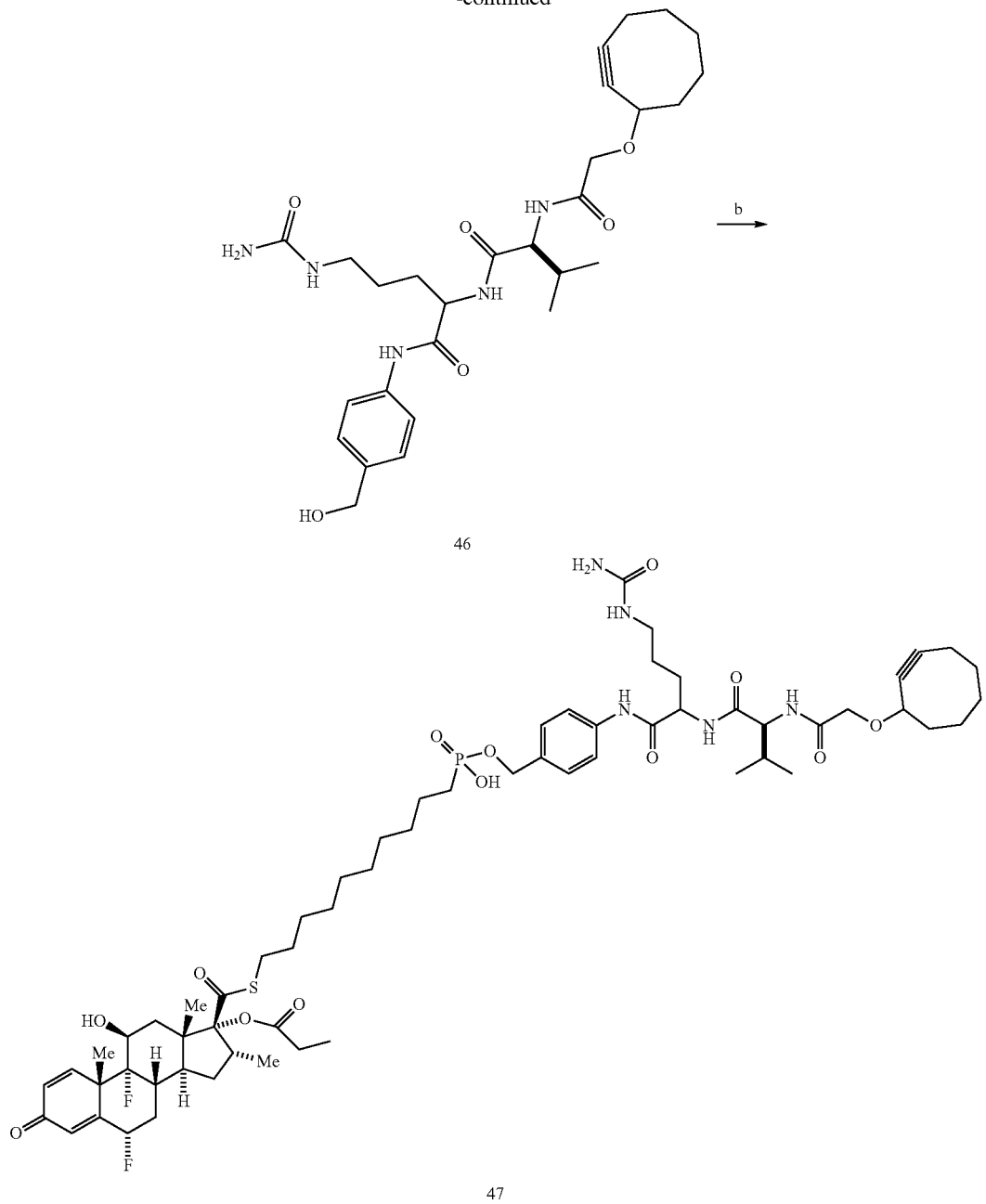

Preparation of (6S,8S,9R,10S,11S,13S,14S,16R, 17R)-17-(((10-(((4-(2-((2 S)-2-(2-(cyclooct-2-yn-1-yloxy)acetamido)-3-methylbutanamido)-5-ureidopentanamido)benzyl)oxy)(hydroxy)phosphoryl) decyl)thio)carbonyl)-6,9-difluoro-11-hydroxy-10,13, 16-trimethyl-3-oxo-6,7,8,9,10,11,12,13,14,15,16,17-dodecahydro-3H-cyclopenta[a]phenanthren-17-yl propionate (47)

Step A: Preparation of 2-((2S)-2-(2-(cyclooct-2-yn-1-yloxy)acetamido)-3-methylbutanamido)-N-(4-(hydroxymethyl)phenyl)-5-ureidopentanamide (46)

In a dry vial equipped with a stir bar, was dissolved 2-((S)-2-amino-3-methylbutanamido)-N-(4-(hydroxymethyl)phenyl)-5-ureidopentanamide (45, 100 mg, 0.264 mmol) in anhydrous DMF (0.6 mL, 0.44 M). To this was added 2,5-dioxopyrrolidin-1-yl 2-(cyclooct-2-yn-1-yloxy) acetate (81 mg, 0.290 mmol, 1.10 eq.) and the reaction stirred 40 minutes at ambient temperature. Additional 2,5-dioxopyrrolidin-1-yl 2-(cyclooct-2-yn-1-yloxy)acetate was added as necessary to complete reaction by LCMS. This crude reaction was directly injected on a reverse phase basic prep HPLC (Phenomenex Gemini-NX C18 OBD 5 um 30×100 mm) with 10 to 60 gradient of organic (0.1% NH$_4$OH/acetonitrile)/aqueous (0.1% NH$_4$OH/water) to give 2-((2S)-2-(2-(cyclooct-2-yn-1-yloxy)acetamido)-3-methylbutanamido)-N-(4-(hydroxymethyl)phenyl)-5-ureidopentanamide. (46, 54 mg, 37.7% yield) LRMS (ES) (M+H)⁺: observed=544.4, calculated=543.6.

Step B: Preparation of (6S,8S,9R,10S,11S,13S,14S, 16R,17R)-17-(((10-(((4-(2-((2S)-2-(2-(cyclooct-2-yn-1-yloxy)acetamido)-3-methylbutanamido)-5-ureidopentanamido)benzyl)oxy)(hydroxy) phosphoryl)decyl)thio)carbonyl)-6,9-difluoro-11-hydroxy-10,13,16-trimethyl-3-oxo-6,7,8,9,10,11,12, 13,14,15,16,17-dodecahydro-3H-cyclopenta[a] phenanthren-17-yl propionate (47)

In a dry vial equipped with a stir bar, was added 3 (50 mg, 0.074 mmol), 46 (40 mg, 0.074 mmol, 1.00 eq.) and DCC (33 mg, 0.162 mmol, 2.20 eq.). To this was added anhydrous pyridine (1.22 mL, 0.06 M) and the resulting mixture was stirred for 3 days at ambient temperature. The pyridine was removed and the residue was dissolved in methanol and directly injected on a reverse phase acidic prep HPLC (Sunfire C18 30×150) with 20 to 90 gradient of organic (0.1% TFA/acetonitrile)/aqueous (0.1% TFA/water to give (6S,8S,9R,10S,11S; 13S,14S,16R,17R)-17-(((10-(((4-(2-((2S)-2-(2-(cyclooct-2-yn-1-yloxy)acetamido)-3-methylbutanamido)-5-ureidopentanamido)benzyl)oxy)(hydroxy) phosphoryl)decyl)thio)carbonyl)-6,9-difluoro-11-hydroxy-10,13,16-trimethyl-3-oxo-6,7,8,9,10,11,12,13,14,15,16,17-dodecahydro-3H-cyclopenta[a]phenanthren-17-yl propionate (47, 30 mg, 33.6% yield). LRMS (ES) (M+H)⁺: observed=1214.6, calculated=1214.4.

The following compounds were made by a similar procedure:

| Compound number | Structure | Mass Spectrometry Data |
|---|---|---|
| 48 | 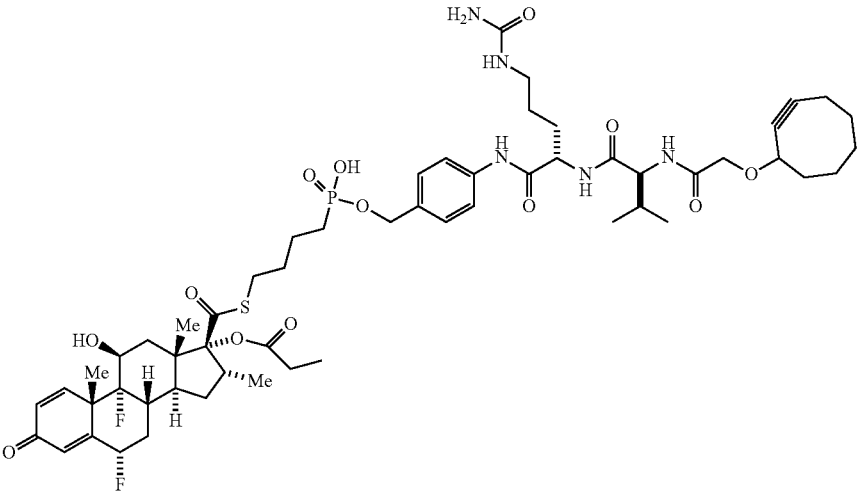 | $C_{56}H_{78}F_2N_5O_{13}PS$ LRMS (ES) (M + H)⁺: observed 1129.5, calculated = 1130.3. |
| 49 | 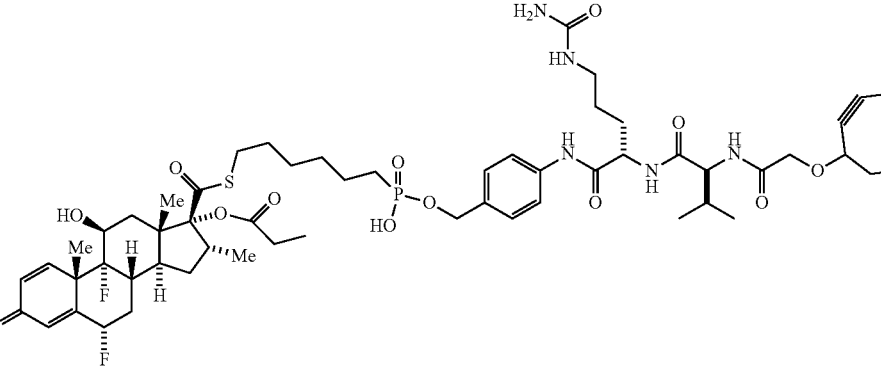 | $C_{58}H_{82}F_2N_5O_{13}PS$ LRMS (ES) (M + H)⁺: observed 1158.5, calculated = 1158.3. |

| Compound number | Structure | Mass Spectrometry Data |
|---|---|---|
| 50 | 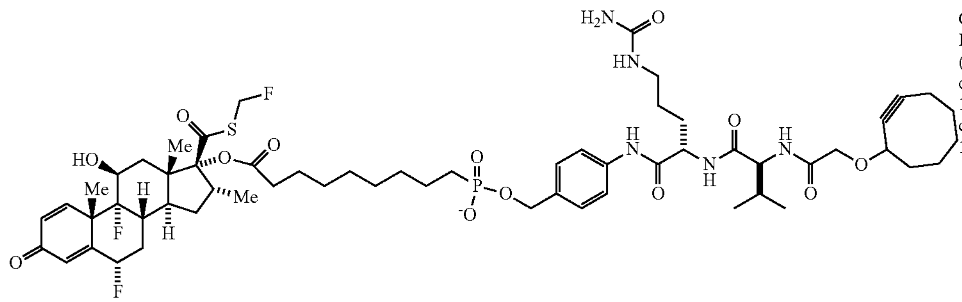 | $C_{59}H_{82}F_3N_5O_{13}PS$ LRMS (ES) $(M + H)^+$: observed 1191.3, calculated = 1190.3. |

Example 8

This example shows the synthesis of various antibody drug conjugates (ADCs).

Site specific conjugation using click (2+3) chemistry. Para-azido phenylalanine containing anti-CD74 antibodies were buffer exchanged into 50 mM Histidine; 100 mM NaCl; 2.5% Trehalose; 0-20% Dimethylamine, pH 6.0 and concentrated to 1-20 mg/mL. 10-15 molar equivalents of cyclooctyne drug-linker were added and reacted for 16-72 hours at 28-30° C. The antibody conjugates were purified over a SP 650S column (Tosoh Biosciences) to remove excess reagents. The conjugates were buffer exchanged into 50 mM Histidine; 100 mM NaCl; 2.5% Trehalose; pH 6.0, 0.22 μm filtered, and stored at 4° C.

| ADC number | Structure |
|---|---|
| αCD74-47 | 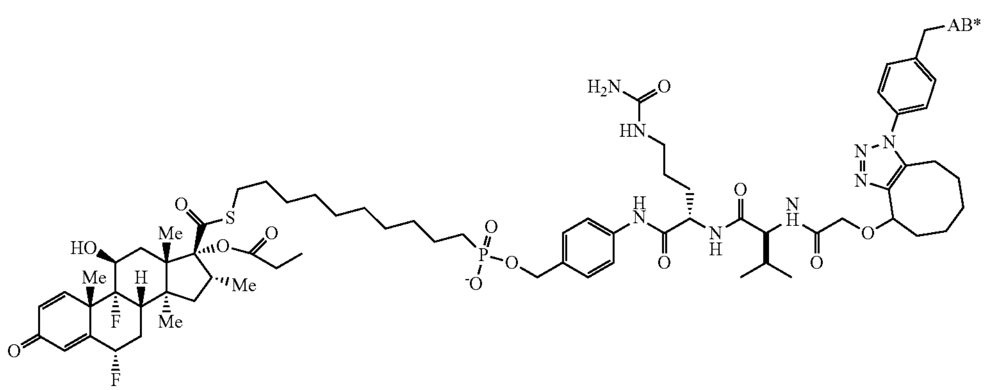 |
| αCD74-50 | 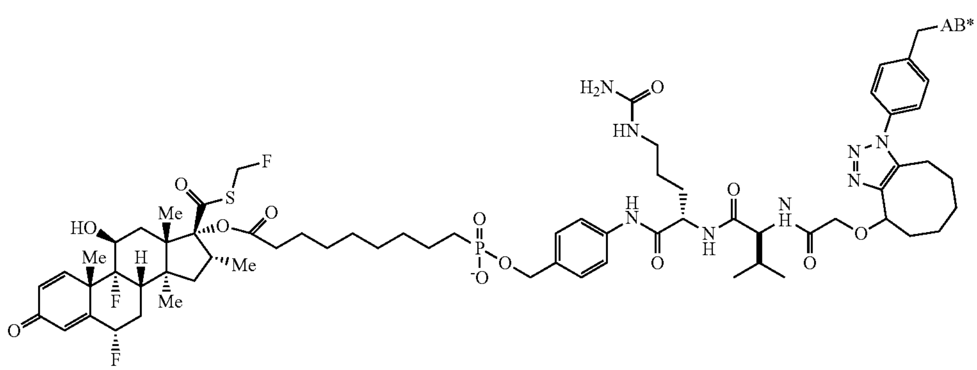 |

| ADC number | Structure |
|---|---|
| αCD74-41 | [Structure: glucocorticoid-linker-triazole-AB* conjugate] |

*AB = antibody

Example 9

The potency of binding to glucocorticoid receptor by small molecule compounds was measured with the Polar-Screen™ Glucocorticoid Receptor Competitor Assay Kit, Red (Life Technology, Catalog #A15898) according to the procedure in the kit. In brief, after compounds were diluted and transferred into assay plates, the fluormone GS red and GR full length protein were subsequently added into the assay plates, along with the positive and negative controls. The samples were mixed on a shaker for 1 minute and then the plates were incubated at room temperature for 2-4 hours with minimal light exposure. The plates were read with an Envision and the relative fluorescent signals were calculated. The data were plotted in GraphPad Prism and the EC50 values were calculated with non-linear regression curve fit of the data in GraphPad Prism.

GILZ gene assays were conducted as follows. HUT78 cells were cultured in IMEM plus 20% heat inactivated FBS and cell density was maintained between 0.1 to 1.2 million/mL. 786-O cells were cultured in RPMI plus 10% heat inactivated FBS. Actively growing cells were harvested and resuspended in HBSS with 2% FBS at 1.1 million cells per mL then dispensed to 384-well V-bottom plates at 45 µL per well. Serially diluted ADC solution was added to the cell plate (5 µL per well) and mixed for 2 min. Cells were then cultured at 37° C., at 5% $CO_2$ for a designated time before supernatant was removed. Cells were harvested in lysis buffer from the Cells-to-Ct kit (40 µL, Life Technologies, 4391851C) following the supplier's protocol and mixed for 10 min followed by addition of 5 µL per well of stop solution from the kit. cDNA was synthesized with a reverse transcription kit (Life Technologies, 4391852C) follow by qPCR using the TaqMan gene expression master mix (Life Technologies, 4369016) with GILZ gene assay (Life Technologies, Hs00608272_m1) and GAPDH assay (Hs2758991_g1) in a duplex format with 3-4 technical replicates.

Determination of apparent permeability was as follows. MDCKII cells (kindly provided by the Netherlands Cancer Institute, under a licensing agreement) were seeded on to 96-well transwell culture plates (Millipore Corp, Billerica, Mass.) and used in experiments after five days in culture. Test compound (1 µM) was prepared in Hank's Balanced Salt Solution (HBSS), 10 mM (4-(2-hydroxyethyl)-1-piperazineethanesulfonic acid) (HEPES, pH 7.4), with 10 µM cyclosporine A (to inhibit endogenous transport) and 1.2 µM dextran Texas red (to confirm monolayer integrity). Substrate solution (150 µL) was added to either the apical (A) or the basolateral (B) compartment of the culture plate, and buffer (150 µL; HBSS, 10 mM HEPES, pH 7.4) with 10 µM cyclosporine A was added to the compartment opposite to that containing the substrate. At t=3 hr, 50 µL samples were removed from both sides of monolayers dosed with test compound and placed in 96 well plates, 50 µL internal standard (1 µM labetolol) and 100 µL HBSS was added to the samples. Samples were analyzed by LC/MS/MS using an Applied Biosystems SCIEX API 5000 triple quadruple mass spectrometer (Concord, ON, Canada) with a Turbo-IonSpray ion source in the positive ion mode. A Thermo Scientific Transcend LX-2 system (Franklin, Mass.) was coupled to the API 5000 with a flow rate of 800 µL/min to direct sample into the mass spectrometer. The apparent permeability ($P_{app}$) was calculated by the following formula for samples taken at t=3 hr:

$$P_{app} = \frac{\text{volume of receptor chamber (mL)}}{[\text{area of membrane (cm}^2\text{)}] \times [\text{initial concentration (µm)}]} \times \frac{\Delta \text{ concentration (µM)}}{\Delta \text{ time }(s)}$$

Where: Volume of Receiver Chamber is 0.15 mL; Area of membrane is 0.11 cm$^2$; the initial concentration is the sum of the concentration measured in the donor plus concentration measured in receiver compartments at t=3 hr; Δ in concentration is concentration in the receiver compartment at 3 hr; and Δ in Time is the incubation time (3×60× 60=10800 s). $P_{app}$ was expressed as $10^{-6}$ cm/s. The $P_{app}$ reported is the average of the A to B and B to A $P_{app}$ values control MDCKII cells at t=3 hr:

$$P_{app} = \frac{P_{app}(a \to B) + P_{app}(B \to A)}{2}$$

The B-A/A-B ratio was calculated by dividing the $P_{app}$ from B to A by the $P_{app}$ from A to B at t=3 hr.

The results of the aforementioned assays with compounds 3, 4, 5, 6, 7, 8, 9, 10, 11, 12, 13, 14, 18, 19, 27, 28, 29, 30, 31, and 32 compared to dexamehtsone, budesonide, anf fluticasone proprionate are shown in Table 1 below.

TABLE 1

| Compound Number | GR Bind IC50 (nM) | GILZ EC50 | GILZ Max | MDCK Permeability (cm × 10−6/sec) |
|---|---|---|---|---|
| Dexamethasone | 2.1 | 3.7 | 100% | 12.9 |
| Budesonide | 0.9 | 1 | 100% | 31.6 |
| Fluticasone Propionate | 0.15 | 0.2 | 100% | 21.5 |
| 3 | 0.44 | 649 | 71% (at 10 uM) | 1.04 |
| 4 | 0.71 | >100 | <10% (at 100 nM) | 1.72 |
| 5 | 160.4 | >10000 | 24% (at 100 nM) | 1.84 |
| 6 | 0.32 | >10000 | 40% (at 10 uM) | n/a |
| 7 | 0.45 | 6450 | 64% (at 10 uM) | 2 |
| 8 | 0.25 | 970 | 66% (at 10 uM) | 2.8 |
| 9 | 1.67 | >10000 | 14.5% (at 10 uM) | n/a |
| 10 | 1.99 | >10000 | 17.3% (at 10 uM) | 1.9 |
| 11 | n/a | 2865 | 81% (at 10 uM) | n/a |
| 12 | 162 | 6777 | 36% (at 10 uM) | n/a |
| 13 | 1225 | >10,000 | 24% (at 10 uM) | n/a |
| 14 | 18.1 | >10,000 | 15% (at 10 uM) | n/a |
| 18 | 0.1 | 3038 | 65% (at 10 uM) | <0.9 |
| 19 | 0.14 | 1289 | 88% (at 10 uM) | n/a |
| 27 | 2 | 2759 | 80% (at 10 uM) | 1.8 |
| 28 | 4.1 | 1267 | 101% (at 10 uM) | 1.6 |
| 29 | 24.2 | 558 | 96% (at 10 uM) | n/a |
| 30 | 2.4 | 3008 | 61% (at 10 uM) | 1.9 |
| 31 | 3.9 | 4175 | 47% (at 10 uM) | 4.1 |
| 32 | 114.8 | 4154 | 86% (at 10 uM) | n/a |

Example 10

The Analogs were conjugated to the antibodies as follows. To initiate conjugation, 10% v/v DMSO was added to the antibody solution, followed by a 15-fold molar excess of cyclooctyne-functionalized drug-linker. The solution was gently mixed and allowed to react at 28° C. for 48 hours. Removal of unreacted drug-linker and aggregates was performed via cation exchange as previously described. The final cation exchange pool was then concentrated and formulated into 50 mM histidine, 100 mM NaCl, 2.5% trehalose, pH 6.0 and 0.22 μm filtered.

Analytical Data for ADCs

UV: The concentration of conjugates was determined by absorbance at 280 nm with a background correction of 320 nm using Agilent U.V spectrometer (Model #8453).

SEC: The ADCs were analyzed by SEC-HPLC (G3000SWXL Tosoh Column 7.8×300 mm (Serial #Y02322), Mobile Phase −200 mM KPO4, 250 mM KCl, pH 6.0+10% IPA; at flow rate 0.5 ml/min, isocratic gradient for 40 min, 10 μg load) on an Agilent 1100 HPLC. The data was processed using the software Agilent Chemstation and the percent monomer was reported.

MS and DAR: The sample was denatured with 3M guanidine HCl, reduced with 150 mM DTT and analyzed by LC-MS (Agilent PLRP-S,4000° A, 8 um, 2.1×150 mm (Serial #0001023345-118) Mobile Phase A—0.05% TFA in Water and Mobile Phase B—0.05% TFA in Acetonitrile, at flow rate 0.3 ml/min, 80° C. for 23 min, 3 μg load) on Agilent Q-TOF LC/MS (Model #6510). Data was acquired and deconvoluted to monoisotopic and singly charged species using the software Agilent Mass Hunter Qualitative Analysis. The identity was confirmed from the mass of the light chain, the unconjugated and conjugated heavy chains. DAR was calculated from the DAD signal.

Residual Drug Linker: Residual Drug Linker was extracted from Antibody Drug Conjugate by precipitating out the antibody with ACN:MeOH (50:50). The supernatant was analyzed by RP-HPLC (Waters X Bridge BEH C18 2.1×150 mm (PN 186003110), Mobile Phase A—4% NH$_4$OH, 1.5% FA in water and Mobile Phase B—Acetonitrile; flow rate 0.3 ml/min, 60° C. for 28 min, 10 μl load) on Agilent Q TOF LC-MS (Model #6510). The data was processed using Agilent Mass Hunter Qualitative Analysis. The Extracted Ion chromatogram (EIC) was integrated and the molarity of the residual drug linker was extrapolated from linear regression analysis of the standard curve.

| Antibody | Drug Linker No. | ADC No. | DAR | % Monomer |
|---|---|---|---|---|
| anti-hCD74 (IgG4) | 47 | 1-474 | 1.6 | 90.6 |
|  | 50 | 1-477 | 1.7 | 98.5 |
|  | 41 | 1-496 | 1.5 | 94.6 |
| anti-RSV (IgG4) | 47 | 2-474 | 1.8 | 96.1 |
|  | 50 | 2-477 | 1.8 | 98.9 |
|  | 41 | 2-496 | 1.5 | 94.3 |

B-Cell Analysis

The carrier solution for all ADCs and naked antibodies was 50 mM histidine pH 6.0, 100 mM NaCl and 5% trehelose. To assure consistency across experiments, ADCs were thawed on ice, dispensed to small aliquots, frozen to −80° C., and those aliquots were then used for experiments with unused material discarded at the end of the day. For all in vitro studies in this report, none of the read outs were measurably different in the presence or absence of the carrier solution. Nevertheless, the final concentration of antibody carrier solution was maintained constant at 1% v/v by serially diluting antibody solution prior to addition to the assay mixture and adding carrier solution to control wells. The same practice was observed for DMSO as the solvent for small molecules, with the final concentration being 0.1% v/v.

For the studies of ADCs bearing reduced permeability payloads frozen human CD19+ B cells purchased from Precision Biosciences (catalog #84400, donor #13108) were thawed and re-suspended in RPMI1640 plus 10% heat-inactivated FBS (cell culture medium) at 1 million cells/mL. ADC or fluticasone was serially diluted to 100× the intended final concentrations. B cells were bulk treated in a 96-well block and subsequently dispensed to 96 well plates (100 μL and 1 million cells per well) and incubated at 37° C., 5% $CO_2$ for 18 or 40 hr. Control wells containing equal percentages of DMSO (0.1%) and ADC buffer (1%) as sample wells were included. Cells were transferred to a 96 well v-bottom plate and spun at 500×g for 5 min. Medium was removed and cells were lysed in 150 μL RLT buffer containing beta-mercaptoethanol. RNA was isolated (RNeasy 96 kit, Qiagen, Cat #74181) and cDNA was synthesized (iScript cDNA Synthesis Kit, BioRad, Cat #170-8891) according to the supplier's protocol. Quantitative PCR was performed on Applied Biosystem's 7900 HT Real-Time PCR System to measure expression of ZBTB16 (Life Technologies, Hs00957433_m1) and GAPDH (Life Technologies, Hs02758991_g1) in duplex format.

The ΔΔCt method was used to calculate fold change of expression of ZBTB16 relative to control sample, using 3 replicates per treatment condition. For free cell impermeable compounds, B cells were seeded at 100,000 cells/well in 90 μL in a 96-well flat bottom plate. Three fold serial dilutions were performed in DMSO, subsequent intermediate 10× stocks were made in tissue-culture medium and then added to the cell plate (10 μL/well). Cells were incubated at 37° C., 5% $CO_2$ for 18 hr, harvested and processed for PCR as described above. EC50 curves were calculated using Graph Pad Prism 6 software using nonlinear fit (agonist) vs. response-variable slope (four parameters) calculation.

The results are shown in Table 2. Potency and maximum activity of reduced permeability glucocorticoids (free payload) and the corresponding anti-CD74-drug conjugates on up-regulation of ZBTB16 mRNA levels in primary human B cells in vitro. Corresponding anti-RSV conjugates with 41, 47 and 50 were inactive at all doses tested.

TABLE 2

| Compound | ZBTB16 mRNA EC50 | ZBTB16 mRNA Max relative to free fluticasone |
|---|---|---|
| Fluticasone propionate | 0.019 nM | 100% |
| 3 | 1100 nM | 75% |
| 18 | 3200 nM | >77% |
| αCD74-41 (DAR = 1.5) | 0.70 ug/mL (7.1 nM in payload) | 22% |
| αCD74-47 (DAR = 1.6) | 0.91 ug/mL (9.8 nM in payload) | 23% |
| αCD74-50 (DAR = 1.7) | 0.13 ug/mL (1.5 nM in payload) | 16% |

Table of Sequences

| SEQ ID NO: | Description | Amino Acid Sequence |
|---|---|---|
| 1 | Anti-CD25 LC CDR1 | RASQSVSSSYLA |
| 2 | Anti-CD25 LC CDR2 | GASSRAT |
| 3 | Anti-CD25 LC CDR3 | QQYSSSPLT |
| 4 | Anti-CD25 HC CDR1 | RYIIN |
| 5 | Anti-CD25 HC CDR2 | RIIPILGVENYAQKFQG |
| 6 | Anti-CD25 HC CDR3 | KDWFDY |
| 7 | Anti-CD25 HC CDR1 | RYPIN |
| 8 | Anti-CD25 HC CDR2 | RIIPILGIADYAQRFQG |
| 9 | Anti-CD25 HC CDR3 | RDWGDY |
| 10 | Anti-CD25 LC CDR3 | QQYGSSPIT |
| 11 | Anti-CD25 HC CDR1 | RYAIN |
| 12 | Anti-CD25 HC CDR2 | RIIPILDIADYAQKFQD |
| 13 | Anti-CD25 HC CDR3 | KDWFDP |
| 14 | Anti-CD25 HC CDR1 | RYPIN |
| 15 | Anti-CD70 LC CDR1 | RASQSVSSYLA |
| 16 | Anti-CD70 LC CDR2 | YDASNRAT |
| 17 | Anti-CD70 LC CDR3 | QQRTNWPLT |
| 18 | Anti-CD70 HC CDR1 | SYIMH |
| 19 | Anti-CD70 HC CDR2 | VISYDGRNKYYADSVK |
| 20 | Anti-CD70 HC CDR3 | DTDGYDFDY |
| 21 | Anti-CD70 LC CDR1 | RASQGISSALA |
| 22 | Anti-CD70 LC CDR2 | DASSLES |
| 23 | Anti-CD70 LC CDR3 | QQFNSYPFT |
| 24 | Anti-CD70 HC CDR1 | YYAMH |
| 25 | Anti-CD70 HC CDR2 | VISYDGSIKYYADSVK |
| 26 | Anti-CD70 HC CDR3 | EGPYSNYLDY |
| 27 | Anti-CD70 LC CDR1 | RASQGISSWLA |
| 28 | Anti-CD70 LC CDR2 | AASSLQS |
| 29 | Anti-CD70 LC CDR3 | QQYNSYPLT |
| 30 | Anti-CD70 HC CDR1 | DYGMH |
| 31 | Anti-CD70 HC CDR2 | VIWYDGSNKYYADSVK |
| 32 | Anti-CD70 HC CDR3 | DSIVMVRGDY |
| 33 | Anti-CD70 LC CDR1 | RASQGISSWLA |
| 34 | Anti-CD70 LC CDR2 | AASSLQS |
| 35 | Anti-CD70 LC CDR3 | QQYNSYPLT |
| 36 | Anti-CD70 HC CDR1 | DHGMH |
| 37 | Anti-CD70 HC CDR2 | VIWYDGSNKYYADSVK |
| 38 | Anti-CD70 HC CDR3 | DSIMVRGDY |
| 39 | Anti-CD70 LC CDR2 | DASNRAT |
| 40 | Anti-CD70 LC CDR3 | QQRSNWPLT |
| 41 | Anti-CD70 HC CDR1 | SDYYWS |
| 42 | Anti-CD70 HC CDR2 | YIYYSGSTNYDPSLKS |
| 43 | Anti-CD70 HC CDR3 | GDGDYGGNCFDY |
| 44 | Anti-CD74 LC CDR1 | RSSQSLVHRNGNTYLH |
| 45 | Anti-CD74 LC CDR2 | TVSNRFS |
| 46 | Anti-CD74 LC CDR3 | SQSSHVPPT |

Table of Sequences

| SEQ ID NO: | Description | Amino Acid Sequence |
|---|---|---|
| 47 | Anti-CD74 HC CDR1 | NYGVN |
| 48 | Anti-CD74 HC CDR2 | WINPNTGEPTFDDDFKG |
| 49 | Anti-CD74 HC CDR3 | SRGKNEAWFAY |
| 50 | Anti-CD74 LC CDR1 | QGISSW |
| 51 | Anti-CD74 LC CDR3 | QQYNSYPLT |
| 52 | Anti-CD74 HC CDR1 | GFTFSSYA |
| 53 | Anti-CD74 HC CDR2 | ISYDGSNK |
| 54 | Anti-CD74 HC CDR3 | ASGRYYGSGSYSSYFD |
| 55 | Anti-CD74 HC CDR2 | ISYDGSIK |
| 56 | Anti-CD74 HC CDR3 | ARGREYTSQNIVILLD |
| 57 | Anti-CD74 HC CDR3 | ARGREITSQNIVILLD |
| 58 | Anti-CD74 HC CDR2 | IWYDGSNK |
| 59 | Anti-CD74 HC CDR3 | ARGGTLVRGAMYGTDV |
| 60 | Anti-CD163 LC CDR1 | ASQSVSSDV |
| 61 | Anti-CD163 LC CDR3 | QDYTSPRT |
| 62 | Anti-CD163 HC CDR1 | GYSITSDY |
| 63 | Anti-CD163 HC CDR3 | CVSGTYYFDYWG |
| 64 | Anti-CD163 LC CDR1 | ASQSVSHDV |
| 65 | Anti-CD163 LC CDR3 | QDYSSPRT |
| 66 | Glycosylation site atN297 of IgG1 | QYNS |
| 67 | Glycosylation site atN297 of IgG4 | QFNS |
| 68 | Mutated glycosylation site of IgG1 or IgG4 | QAQS |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

---

What is claimed:

1. A compound of the formula

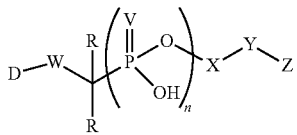

wherein
- V is selected from O and S;
- W is selected from a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group;
- X is selected from a covalent bond; a carbon atom; a heteroatom; an optionally substituted group selected from the group consisting of acyl, aliphatic, heteroaliphatic, aryl, heteroaryl, and heterocyclic; or nucleoside;
- Y is selected from a covalent bond or a bivalent, straight or branched, saturated or unsaturated, optionally substituted C1-30 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group;
- Z is a reactive functional group selected from the group consisting of N-hydroxysuccinimide, para-nitrophenyl carbonate, para-nitrophenyl carbamate, azide, hydrazine, pentafluorophenyl, haloacetamide, maleimide, hydroxylamine, cycloalkyne, heterocycloalkyne, alkyne, diene, and heterocyclic azadiene, wherein halo is iodine (I), bromine (Br), fluorine (F), or chlorine (Cl) and hetero is N, O, or S;
- D is a therapeutic agent linked to W via a covalent linkage formed via a reaction with a primary amine, a secondary amine, a hydroxyl, a sulfhydryl, a carboxyl, an aldehyde, or a ketone group of the therapeutic agent;
- Each occurrence of R is independently hydrogen, an acyl, arylalkyl, aliphatic, aryl, heteroaryl, or heteroaliphatic group; and
- n is 1, 2, 3, or 4.

2. The compound of claim 1, wherein the therapeutic agent is an anti-inflammatory agent.

3. The compound of claim 2, wherein the anti-inflammatory agent is a glucocorticoid receptor agonist.

4. The compound of claim 2 wherein the anti-inflammatory agent is Cortisol, cortisone acetate, beclometasone, prednisone, prednisolone, methylprednisolone, betamethasone, trimcinolone, budesonide, dexamethasone, fluticasone, or mometasone.

5. The compound of claim 1, wherein the therapeutic agent is a cytotoxic agent.

* * * * *